(12) United States Patent
Booth et al.

(10) Patent No.: US 9,965,595 B2
(45) Date of Patent: *May 8, 2018

(54) INSULIN MANAGEMENT

(71) Applicant: Aseko, Inc., Greenville, SC (US)

(72) Inventors: Robert C. Booth, Columbus, NC (US); Harry Hebblewhite, Atlanta, GA (US)

(73) Assignee: Aseko, Inc., Greenville, SC (US)

( * ) Notice: Subject to any disclaimer, the term of this patent is extended or adjusted under 35 U.S.C. 154(b) by 64 days.

This patent is subject to a terminal disclaimer.

(21) Appl. No.: 15/342,606

(22) Filed: Nov. 3, 2016

(65) Prior Publication Data

US 2017/0068802 A1    Mar. 9, 2017

Related U.S. Application Data

(60) Continuation of application No. 14/938,997, filed on Nov. 12, 2015, now Pat. No. 9,504,789, which is a
(Continued)

(51) Int. Cl.
*G01N 33/48* (2006.01)
*G06F 19/00* (2018.01)
(Continued)

(52) U.S. Cl.
CPC ...... *G06F 19/3468* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

| 561,422 A | 6/1896 | Minnis |
|---|---|---|
| 4,055,175 A | 10/1977 | Clemens et al. |

(Continued)

FOREIGN PATENT DOCUMENTS

| AU | 199460325 A | 8/1994 |
|---|---|---|
| AU | 2009283013 A1 | 2/2010 |

(Continued)

OTHER PUBLICATIONS

Kaufman et al. (Diabetes Metab. Res. Rev. 1999, vol. 15, p. 338-352).*

(Continued)

*Primary Examiner* — Larry D Riggs, II
(74) *Attorney, Agent, or Firm* — Honigman Miller Schwartz and Cohn LLP

(57) ABSTRACT

A method of administering insulin includes receiving blood glucose measurements of a patient at a data processing device from a glucometer. The blood glucose measurements are separated by a time interval. The method also includes receiving patient information at the data processing device and selecting a subcutaneous insulin treatment from a collection of subcutaneous insulin treatments. The selection is based on the blood glucose measurements and the patient information. The selection includes one or more of a subcutaneous standard program, a subcutaneous program without meal boluses, a meal-by-meal subcutaneous program without carbohydrate counting, a meal-by-meal subcutaneous program with carbohydrate counting, and a subcutaneous program for non-diabetic patients. The method also includes executing, using the data processing device, the selected subcutaneous insulin treatment.

24 Claims, 34 Drawing Sheets

Related U.S. Application Data division of application No. 14/524,918, filed on Oct. 27, 2014, now Pat. No. 9,233,204.

(60) Provisional application No. 62/009,575, filed on Jun. 9, 2014, provisional application No. 61/934,300, filed on Jan. 31, 2014.

(51) Int. Cl.

| | | |
|---|---|---|
| *A61M 5/172* | (2006.01) | |
| *A61B 5/145* | (2006.01) | |
| *A61B 5/00* | (2006.01) | |
| *A61M 5/14* | (2006.01) | |
| *A61M 5/142* | (2006.01) | |

(52) U.S. Cl.
CPC ............ *A61M 5/14* (2013.01); *A61M 5/1723* (2013.01); *G06F 19/345* (2013.01); *G06F 19/3418* (2013.01); *A61B 5/4848* (2013.01); *A61M 2005/14208* (2013.01); *A61M 2005/14296* (2013.01); *A61M 2005/1726* (2013.01); *A61M 2205/18* (2013.01); *A61M 2205/3327* (2013.01); *A61M 2205/35* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/507* (2013.01); *A61M 2205/52* (2013.01); *A61M 2205/581* (2013.01); *A61M 2230/201* (2013.01)

(56) References Cited

U.S. PATENT DOCUMENTS

| | | |
|---|---|---|
| 4,151,845 A | 5/1979 | Clemens |
| 4,206,755 A | 6/1980 | Klein |
| 4,403,984 A | 9/1983 | Ash et al. |
| 4,464,170 A | 8/1984 | Clemens et al. |
| 4,731,726 A | 3/1988 | Allen, III |
| 4,850,959 A | 7/1989 | Findl |
| 4,911,168 A | 3/1990 | Davis |
| 4,947,845 A | 8/1990 | Davis |
| 4,981,779 A | 1/1991 | Wagner |
| 5,091,190 A | 2/1992 | Kuczynski et al. |
| 5,216,597 A | 6/1993 | Beckers |
| 5,251,126 A | 10/1993 | Kahn et al. |
| 5,614,224 A | 3/1997 | Womack |
| 5,822,715 A | 10/1998 | Worthington et al. |
| 5,956,501 A | 9/1999 | Brown |
| 5,998,363 A | 12/1999 | Forse et al. |
| 6,024,699 A | 2/2000 | Surwit et al. |
| 6,186,145 B1 | 2/2001 | Brown |
| 6,233,539 B1 | 5/2001 | Brown |
| 6,379,301 B1 | 4/2002 | Worthington et al. |
| 6,428,825 B2 | 8/2002 | Sharma et al. |
| 6,472,366 B2 | 10/2002 | Kishino et al. |
| 6,540,672 B1 | 4/2003 | Simonsen et al. |
| 6,544,212 B2 | 4/2003 | Galley et al. |
| 6,560,471 B1 | 5/2003 | Heller et al. |
| 6,572,542 B1 | 6/2003 | Houben et al. |
| 6,575,905 B2 | 6/2003 | Knobbe et al. |
| 6,605,039 B2 | 8/2003 | Houben et al. |
| 6,615,081 B1 | 9/2003 | Boveja |
| 6,669,663 B1 | 12/2003 | Thompson |
| 6,740,072 B2 | 5/2004 | Starkweather et al. |
| 6,808,703 B2 | 10/2004 | Park et al. |
| 6,890,568 B2 | 5/2005 | Pierce et al. |
| 6,927,246 B2 | 8/2005 | Noronha et al. |
| 7,025,425 B2 | 4/2006 | Kovatchev et al. |
| 7,039,560 B2 | 5/2006 | Kawatahara et al. |
| 7,060,059 B2 | 6/2006 | Keith et al. |
| 7,108,680 B2 | 9/2006 | Rohr et al. |
| 7,137,951 B2 | 11/2006 | Pilarski |
| 7,167,818 B2 | 1/2007 | Brown |
| 7,204,823 B2 | 4/2007 | Estes et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,404,796 B2 | 7/2008 | Ginsberg |
| 7,498,318 B1 | 3/2009 | Stahl et al. |
| 7,509,156 B2 | 3/2009 | Flanders |
| 7,553,281 B2 | 6/2009 | Hellwig et al. |
| 7,651,845 B2 | 1/2010 | Doyle, III et al. |
| 7,704,226 B2 | 4/2010 | Mueller, Jr. et al. |
| 7,734,323 B2 | 6/2010 | Blomquist et al. |
| 7,806,886 B2 | 10/2010 | Kanderian, Jr. et al. |
| 7,824,333 B2 | 11/2010 | Otto et al. |
| 7,837,622 B2 | 11/2010 | Itoh et al. |
| 7,853,455 B2 | 12/2010 | Brown |
| 7,877,271 B2 | 1/2011 | Brown |
| 7,901,625 B2 | 3/2011 | Brown |
| 7,904,310 B2 | 3/2011 | Brown |
| 7,912,688 B2 | 3/2011 | Brown |
| 7,920,998 B2 | 4/2011 | Brown |
| 7,949,507 B2 | 5/2011 | Brown |
| 7,985,848 B2 | 7/2011 | Woo et al. |
| 8,088,731 B2 | 1/2012 | Knudsen et al. |
| 8,117,020 B2 | 2/2012 | Abensour et al. |
| 8,185,412 B1 | 5/2012 | Harpale |
| 8,198,320 B2 | 6/2012 | Liang et al. |
| 8,204,729 B2 | 6/2012 | Sher |
| 8,206,340 B2 | 6/2012 | Arefieg |
| 8,257,300 B2 | 9/2012 | Budiman et al. |
| 8,257,735 B2 | 9/2012 | Lau et al. |
| 8,318,221 B2 | 11/2012 | Miller et al. |
| 8,329,232 B2 | 12/2012 | Cheng et al. |
| 8,333,752 B2 | 12/2012 | Veit et al. |
| 8,370,077 B2 | 2/2013 | Bashan et al. |
| 8,398,616 B2 | 3/2013 | Budiman |
| 8,420,125 B2 | 4/2013 | Webster et al. |
| 8,420,621 B2 | 4/2013 | Lai et al. |
| 8,457,901 B2 | 6/2013 | Beshan et al. |
| 8,527,208 B2 | 9/2013 | Prud'homme et al. |
| 8,532,933 B2 | 9/2013 | Duke et al. |
| 8,548,544 B2 | 10/2013 | Kircher, Jr. et al. |
| 8,571,801 B2 | 10/2013 | Anfinsen et al. |
| 8,579,879 B2 | 11/2013 | Palerm et al. |
| 8,600,682 B2 | 12/2013 | Bashan et al. |
| 8,635,054 B2 | 1/2014 | Brown |
| 8,679,016 B2 | 3/2014 | Mastrototaro et al. |
| 8,690,934 B2 | 4/2014 | Boyden et al. |
| 8,700,161 B2 | 4/2014 | Harel et al. |
| 8,703,183 B2 | 4/2014 | Lara |
| 8,718,949 B2 | 5/2014 | Blomquist et al. |
| 8,755,938 B2 | 6/2014 | Weinert et al. |
| 8,766,803 B2 | 7/2014 | Bousamra et al. |
| 8,828,390 B2 | 9/2014 | Herrera et al. |
| 8,834,367 B2 | 9/2014 | Laan et al. |
| 8,870,807 B2 | 10/2014 | Mantri et al. |
| 8,911,367 B2 | 12/2014 | Brister et al. |
| 8,919,180 B2 | 12/2014 | Gottlieb et al. |
| 8,992,464 B2 | 3/2015 | Bashan et al. |
| 2001/0002269 A1 | 5/2001 | Zhao |
| 2003/0028089 A1 | 2/2003 | Galley et al. |
| 2003/0050621 A1 | 3/2003 | Lebel et al. |
| 2003/0199445 A1 | 10/2003 | Knudsen et al. |
| 2003/0208110 A1 | 11/2003 | Mault et al. |
| 2004/0042272 A1 | 3/2004 | Kurata |
| 2004/0044272 A1 | 3/2004 | Moerman et al. |
| 2004/0054263 A1 | 3/2004 | Moerman et al. |
| 2005/0020681 A1 | 1/2005 | Takayama et al. |
| 2005/0049179 A1 | 3/2005 | Davidson et al. |
| 2005/0054818 A1 | 3/2005 | Brader et al. |
| 2005/0055010 A1 | 3/2005 | Pettis et al. |
| 2005/0096637 A1 | 5/2005 | Heruth |
| 2005/0171503 A1 | 8/2005 | Van Den Berghe et al. |
| 2005/0176621 A1 | 8/2005 | Brader et al. |
| 2005/0177398 A1 | 8/2005 | Watanabe et al. |
| 2005/0187749 A1 | 8/2005 | Singley |
| 2005/0192494 A1 | 9/2005 | Ginsberg |
| 2005/0192557 A1 | 9/2005 | Brauker et al. |
| 2005/0197621 A1 | 9/2005 | Poulsen et al. |

(56) References Cited

U.S. PATENT DOCUMENTS

| | | |
|---|---|---|
| 2005/0267195 A1 | 12/2005 | Mikoshiba et al. |
| 2005/0272640 A1 | 12/2005 | Doyle et al. |
| 2006/0040003 A1 | 2/2006 | Needleman et al. |
| 2006/0078593 A1 | 4/2006 | Strozier et al. |
| 2006/0160722 A1 | 7/2006 | Green et al. |
| 2006/0173260 A1 | 8/2006 | Gaoni et al. |
| 2006/0188995 A1 | 8/2006 | Ryan et al. |
| 2006/0224109 A1 | 10/2006 | Steil et al. |
| 2006/0264895 A1 | 11/2006 | Flanders |
| 2007/0036872 A1 | 2/2007 | Tsuboi et al. |
| 2007/0060796 A1 | 3/2007 | Kim |
| 2007/0078314 A1 | 4/2007 | Grounsell et al. |
| 2007/0078818 A1 | 4/2007 | Zivitz et al. |
| 2007/0160678 A1 | 7/2007 | Guimberteau et al. |
| 2007/0168224 A1 | 7/2007 | Letzt et al. |
| 2007/0249916 A1 | 10/2007 | Pesach et al. |
| 2007/0282186 A1 | 12/2007 | Gilmore |
| 2007/0293742 A1 | 12/2007 | Simonsen et al. |
| 2008/0097289 A1 | 4/2008 | Steil et al. |
| 2008/0119421 A1 | 5/2008 | Tuszynski et al. |
| 2008/0119705 A1 | 5/2008 | Patel et al. |
| 2008/0139511 A1 | 6/2008 | Friesen |
| 2008/0139907 A1 | 6/2008 | Rao et al. |
| 2008/0172030 A1 | 7/2008 | Blomquist |
| 2008/0188796 A1 | 8/2008 | Steil et al. |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0255707 A1 | 10/2008 | Hebblewhite et al. |
| 2008/0269585 A1 | 10/2008 | Ginsberg |
| 2008/0299079 A1 | 12/2008 | Meezan et al. |
| 2008/0306353 A1 | 12/2008 | Douglas et al. |
| 2009/0029933 A1 | 1/2009 | Velloso et al. |
| 2009/0036753 A1 | 2/2009 | King |
| 2009/0054753 A1 | 2/2009 | Robinson et al. |
| 2009/0069636 A1 | 3/2009 | Zivitz et al. |
| 2009/0099438 A1 | 4/2009 | Flanders |
| 2009/0110752 A1 | 4/2009 | Shang et al. |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0240127 A1 | 9/2009 | Ray |
| 2009/0242399 A1 | 10/2009 | Kamath et al. |
| 2009/0247982 A1 | 10/2009 | Krulevitch et al. |
| 2009/0253970 A1 | 10/2009 | Bashan et al. |
| 2009/0253973 A1 | 10/2009 | Bashan et al. |
| 2009/0281519 A1 | 11/2009 | Rao et al. |
| 2009/0299152 A1 | 12/2009 | Taub et al. |
| 2009/0312250 A1 | 12/2009 | Ryu et al. |
| 2010/0016700 A1 | 1/2010 | Sieh et al. |
| 2010/0035795 A1 | 2/2010 | Boss et al. |
| 2010/0137788 A1 | 6/2010 | Braithwaite et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0168660 A1 | 7/2010 | Galley et al. |
| 2010/0198142 A1 | 8/2010 | Sloan et al. |
| 2010/0256047 A1 | 10/2010 | Sieh et al. |
| 2010/0262434 A1 | 10/2010 | Shaya |
| 2010/0286601 A1 | 11/2010 | Yodfat et al. |
| 2010/0305545 A1 | 12/2010 | Kanderian, Jr. et al. |
| 2010/0324382 A1 | 12/2010 | Cantwell et al. |
| 2010/0331652 A1 | 12/2010 | Groll et al. |
| 2010/0331654 A1 | 12/2010 | Jerdonek et al. |
| 2010/0332142 A1 | 12/2010 | Shadforth et al. |
| 2011/0021894 A1 | 1/2011 | Mohanty et al. |
| 2011/0071365 A1 | 3/2011 | Lee et al. |
| 2011/0071464 A1 | 3/2011 | Palerm |
| 2011/0098548 A1 | 4/2011 | Budiman et al. |
| 2011/0115894 A1 | 5/2011 | Burnett |
| 2011/0119081 A1 | 5/2011 | Vespasiani |
| 2011/0152830 A1 | 6/2011 | Ruchti et al. |
| 2011/0178008 A1 | 7/2011 | Arai et al. |
| 2011/0213332 A1 | 9/2011 | Mozayeny |
| 2011/0217396 A1 | 9/2011 | Oldani |
| 2011/0218489 A1 | 9/2011 | Mastrototaro et al. |
| 2011/0229602 A1 | 9/2011 | Aymard et al. |
| 2011/0286984 A1 | 11/2011 | Huang |
| 2011/0305771 A1 | 12/2011 | Sampalis |
| 2011/0313674 A1 | 12/2011 | Duke et al. |
| 2011/0319322 A1 | 12/2011 | Bashan et al. |
| 2012/0003339 A1 | 1/2012 | Minacapelli |
| 2012/0022353 A1 | 1/2012 | Bashan et al. |
| 2012/0046606 A1 | 2/2012 | Arefieg |
| 2012/0053222 A1 | 3/2012 | Gorrell et al. |
| 2012/0058942 A1 | 3/2012 | Dupre |
| 2012/0065482 A1 | 3/2012 | Robinson et al. |
| 2012/0095311 A1 | 4/2012 | Ramey et al. |
| 2012/0123234 A1 | 5/2012 | Atlas et al. |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0232520 A1 | 9/2012 | Sloan et al. |
| 2012/0238853 A1 | 9/2012 | Arefieg |
| 2012/0244096 A1 | 9/2012 | Xie et al. |
| 2012/0295985 A1 | 11/2012 | Miller et al. |
| 2013/0022592 A1 | 1/2013 | Vaughn et al. |
| 2013/0030358 A1 | 1/2013 | Yodfat et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0158503 A1 | 6/2013 | Kanderian, Jr. et al. |
| 2013/0165901 A1 | 6/2013 | Ruchti et al. |
| 2013/0190583 A1 | 7/2013 | Grosman et al. |
| 2013/0225683 A1 | 8/2013 | Gagnon et al. |
| 2013/0233727 A1 | 9/2013 | Tsai et al. |
| 2013/0245547 A1 | 9/2013 | El-Khatib et al. |
| 2013/0267796 A1 | 10/2013 | Moreno |
| 2013/0281796 A1 | 10/2013 | Pan |
| 2013/0282301 A1 | 10/2013 | Rush |
| 2013/0289883 A1 | 10/2013 | Bashan et al. |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0024907 A1 | 1/2014 | Howell et al. |
| 2014/0037749 A1 | 2/2014 | Shea et al. |
| 2014/0057331 A1 | 2/2014 | Tajima et al. |
| 2014/0066735 A1 | 3/2014 | Engelhardt et al. |
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0296943 A1 | 10/2014 | Maxik et al. |
| 2014/0303466 A1 | 10/2014 | Fitzpatrick et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |
| 2014/0349256 A1 | 11/2014 | Connor |
| 2014/0349257 A1 | 11/2014 | Connor |
| 2014/0356420 A1 | 12/2014 | Huang |
| 2014/0363794 A1 | 12/2014 | Angelides |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |
| 2015/0025903 A1 | 1/2015 | Mueller-Wolf |
| 2015/0031053 A1 | 1/2015 | Moerman |
| 2015/0037406 A1 | 2/2015 | Bernabeu Martinez et al. |

FOREIGN PATENT DOCUMENTS

| | | |
|---|---|---|
| AU | 2010330746 A1 | 7/2012 |
| CA | 2519249 A1 | 10/2004 |

(56) References Cited

FOREIGN PATENT DOCUMENTS

| | | |
|---|---|---|
| CA | 2670512 A1 | 7/2008 |
| CA | 2720302 A1 | 12/2009 |
| CA | 2720304 A1 | 12/2009 |
| CA | 2733593 A1 | 2/2010 |
| CA | 2752637 A1 | 9/2010 |
| CA | 2761647 A1 | 12/2010 |
| CA | 2766944 A1 | 1/2011 |
| CA | 2784143 A1 | 6/2011 |
| CN | 102016855 A | 4/2011 |
| CN | 102016906 A | 4/2011 |
| CN | 102300501 A | 12/2011 |
| CN | 102395310 A | 3/2012 |
| CN | 102481101 A | 5/2012 |
| CN | 102946804 A | 2/2013 |
| DE | 1082412 T1 | 10/2001 |
| EP | 461207 A1 | 12/1991 |
| EP | 483595 A2 | 5/1992 |
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1082412 A2 | 3/2001 |
| EP | 1115389 A1 | 7/2001 |
| EP | 483595 | 12/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1610758 A2 | 1/2006 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 1921981 A2 | 5/2008 |
| EP | 2114491 A1 | 11/2009 |
| EP | 2129277 A2 | 12/2009 |
| EP | 2139393 A2 | 1/2010 |
| EP | 2170430 A2 | 4/2010 |
| EP | 2257218 A2 | 12/2010 |
| EP | 2260423 A2 | 12/2010 |
| EP | 2260462 A2 | 12/2010 |
| EP | 2276405 A1 | 1/2011 |
| EP | 2300046 A2 | 3/2011 |
| EP | 2328608 A2 | 6/2011 |
| EP | 2352456 A1 | 8/2011 |
| EP | 2355669 A2 | 8/2011 |
| EP | 2377465 A1 | 10/2011 |
| EP | 2384750 A1 | 11/2011 |
| EP | 2393419 A1 | 12/2011 |
| EP | 2400882 A1 | 1/2012 |
| EP | 2418972 A1 | 2/2012 |
| EP | 2442719 A2 | 4/2012 |
| EP | 2448432 A1 | 5/2012 |
| EP | 2448468 A1 | 5/2012 |
| EP | 2448469 A2 | 5/2012 |
| EP | 2482712 A1 | 8/2012 |
| EP | 2516671 A1 | 10/2012 |
| EP | 2518655 A2 | 10/2012 |
| EP | 2525863 A1 | 11/2012 |
| EP | 2535831 A1 | 12/2012 |
| EP | 2552313 A2 | 2/2013 |
| EP | 2582297 A1 | 4/2013 |
| EP | 2585133 A1 | 5/2013 |
| EP | 2590559 A2 | 5/2013 |
| EP | 2596448 A1 | 5/2013 |
| EP | 2603133 A1 | 6/2013 |
| EP | 2605819 A1 | 6/2013 |
| EP | 2640373 A1 | 9/2013 |
| EP | 2641084 A1 | 9/2013 |
| EP | 2644088 A1 | 10/2013 |
| EP | 2654777 A2 | 10/2013 |
| EP | 2659407 A1 | 11/2013 |
| EP | 2666369 A1 | 11/2013 |
| EP | 2685895 A1 | 1/2014 |
| EP | 2720713 A2 | 4/2014 |
| EP | 2736404 A1 | 6/2014 |
| EP | 2742447 A2 | 6/2014 |
| EP | 2742449 A2 | 6/2014 |
| EP | 2745225 A2 | 6/2014 |
| EP | 2760335 A1 | 8/2014 |
| EP | 2763722 A2 | 8/2014 |
| EP | 2798548 A1 | 11/2014 |
| EP | 2822647 A1 | 1/2015 |
| JP | 04800928 B2 | 10/2011 |
| KR | 2011052664 A | 5/2011 |
| KR | 2012047841 A | 5/2012 |
| RU | 2011109016 A | 9/2012 |
| WO | WO-1992019260 A1 | 11/1992 |
| WO | WO-1996009823 A1 | 4/1996 |
| WO | WO-1999044496 A1 | 9/1999 |
| WO | WO-1999063101 A2 | 12/1999 |
| WO | WO-2002036139 | 5/2002 |
| WO | WO-2003024468 | 3/2003 |
| WO | WO-2003077895 | 9/2003 |
| WO | WO-2003094927 | 11/2003 |
| WO | WO-2004084820 A2 | 10/2004 |
| WO | WO-2005041022 A1 | 5/2005 |
| WO | WO-2005081119 A2 | 9/2005 |
| WO | WO-2005081170 A2 | 9/2005 |
| WO | WO-2005081171 A2 | 9/2005 |
| WO | WO-2005081173 A1 | 9/2005 |
| WO | WO-2005110222 A1 | 11/2005 |
| WO | WO-2006022619 A2 | 3/2006 |
| WO | WO-2006022629 A1 | 3/2006 |
| WO | WO-2006022633 A1 | 3/2006 |
| WO | WO-2006022634 A1 | 3/2006 |
| WO | WO-2006022636 A1 | 3/2006 |
| WO | WO-2006022638 A1 | 3/2006 |
| WO | WO-2006044556 A2 | 4/2006 |
| WO | WO-2003101177 | 7/2006 |
| WO | WO-2006079124 A2 | 7/2006 |
| WO | WO-2006091918 A2 | 8/2006 |
| WO | WO-2006130901 A1 | 12/2006 |
| WO | WO-2007116226 A2 | 10/2007 |
| WO | WO-2007149533 A2 | 12/2007 |
| WO | WO-2008005761 A2 | 1/2008 |
| WO | WO-2008013324 A1 | 1/2008 |
| WO | WO-2008057213 A1 | 5/2008 |
| WO | WO-2008057384 A2 | 5/2008 |
| WO | WO-2008067245 A2 | 6/2008 |
| WO | WO-2008088490 A1 | 7/2008 |
| WO | WO-2008112078 A2 | 9/2008 |
| WO | WO-2008124478 A1 | 10/2008 |
| WO | WO-2009002455 A1 | 12/2008 |
| WO | WO-2009005960 A2 | 1/2009 |
| WO | WO-2009075925 A1 | 6/2009 |
| WO | WO-2009139846 A1 | 11/2009 |
| WO | WO-2009146119 A2 | 12/2009 |
| WO | WO-2009146121 A2 | 12/2009 |
| WO | WO-2010021879 A2 | 2/2010 |
| WO | WO-2010056718 A2 | 5/2010 |
| WO | WO-2010075350 A1 | 7/2010 |
| WO | WO-2010089304 A1 | 8/2010 |
| WO | WO-2010089305 A1 | 8/2010 |
| WO | WO-2010089306 A1 | 8/2010 |
| WO | WO-2010089307 A1 | 8/2010 |
| WO | WO-2010091102 A1 | 8/2010 |
| WO | WO-2010097796 A1 | 9/2010 |
| WO | WO-2010135646 A1 | 11/2010 |
| WO | WO-2010147659 A2 | 12/2010 |

(56) References Cited

FOREIGN PATENT DOCUMENTS

| | | |
|---|---|---|
| WO | WO-2011008520 A2 | 1/2011 |
| WO | WO-2011037607 A2 | 3/2011 |
| WO | WO-2011075687 A1 | 6/2011 |
| WO | WO-2011089600 A1 | 7/2011 |
| WO | WO-2011094352 A1 | 8/2011 |
| WO | WO-2011157402 A1 | 12/2011 |
| WO | WO-2012023964 A1 | 2/2012 |
| WO | WO-2012047800 A1 | 4/2012 |
| WO | WO-2012065556 A1 | 5/2012 |
| WO | WO-2012097064 A1 | 7/2012 |
| WO | WO-2012122520 A1 | 9/2012 |
| WO | WO-2012148252 A2 | 11/2012 |
| WO | WO-2012161670 A2 | 11/2012 |
| WO | WO-2012177963 A1 | 12/2012 |
| WO | WO-2013040712 A1 | 3/2013 |
| WO | WO-2013050309 A1 | 4/2013 |
| WO | WO-2013086372 A1 | 6/2013 |
| WO | WO-2013096769 A1 | 6/2013 |
| WO | WO-2013108262 A1 | 7/2013 |
| WO | WO-2013134548 A2 | 9/2013 |
| WO | WO-2013172833 A1 | 11/2013 |
| WO | WO-2013177565 A1 | 11/2013 |
| WO | WO-2014011488 A2 | 1/2014 |
| WO | WO-2014012084 A1 | 1/2014 |
| WO | WO-2014023834 A2 | 2/2014 |
| WO | WO-2014024201 A1 | 2/2014 |
| WO | WO-2014028607 A1 | 2/2014 |
| WO | WO-2014068007 A1 | 5/2014 |
| WO | WO-2014075135 | 5/2014 |
| WO | WO-2014075135 A1 | 5/2014 |
| WO | WO-2014099829 | 6/2014 |
| WO | WO-2014099829 A1 | 6/2014 |
| WO | WO-2014106263 A2 | 7/2014 |
| WO | WO-2014145049 A2 | 9/2014 |
| WO | WO-2014149535 | 9/2014 |
| WO | WO-2014149535 A1 | 9/2014 |
| WO | WO-2014149781 A1 | 9/2014 |
| WO | WO-2014152704 A1 | 9/2014 |
| WO | WO-2014162549 A1 | 10/2014 |
| WO | WO-2014162549 A1 | 10/2014 |
| WO | WO-2014164226 A2 | 10/2014 |
| WO | WO-2014179171 A1 | 11/2014 |
| WO | WO-2014187812 A1 | 11/2014 |
| WO | WO-2014190231 A1 | 11/2014 |
| WO | WO-2014202024 A1 | 12/2014 |
| WO | WO-2014209630 A2 | 12/2014 |
| WO | WO-2014209634 A1 | 12/2014 |

OTHER PUBLICATIONS

Kim, Sarah et al., Hyperglycemia control of the Nil per os patient in the intensive care unit: Introduction of a simple subcutaneous insulin algorithm, Journal of Diabetes Science and Technology, Nov. 2012, vol. 6, Issue 6, pp. 1413-1419.

Vaidya, Anand et al., "Improving the management of diabetes in hospitalized patients: The result of a computer-based house staff training program", Diabetes Technology & Therapeutics, 2012, vol. 14, No. 7, pp. 610-618.

Lee, Joshua et al., "Indication-based ordering: A new paradigm for glycemic control in hospitalized inpatients", Journal of Diabetes Science and Technology, May 2008, vol. 2, Issue 3, pp. 349-356.

Nau, Konrad C. et al, "Glycemic Control in hospitalized patients not in intensive care: Beyond sliding-scale insulin", American Family Physician, May 1, 2010, vol. 81, No. 9, pp. 1130-1133.

International Search Report and Written Opinion for Application No. PCT/US2015/011559 dated Apr. 29, 2015.

International Search Report and Written Opinion for Application No. PCT/US2015/011086 dated Apr. 29, 2015.

International Search Report and Written Opinion for Application No. PCT/US2015/011574 dated Apr. 24, 2015.

\* cited by examiner

New Patient Information

| Name: | John Doe |
| Height: | 5' 8" |
| Weight: | 210 |
| Date of Birth: | 4/10/1938 |
| Diabetes History | |
| Age: | 75 |
| Other: | |

IV   SubQ

| Current Patients List | | | |
|---|---|---|---|
| Patient Name | | Patient ID | Room |
| Adkins, Frankie (IV)(SubQ) | | 704563 | 502 |
| Anderson, Mike (IV)(SubQ) | | 705648 | 504 |
| Anton, Mike (IV)(SubQ) | | 712546 | 302 |
| Briggs, George (IV)(SubQ) | | 702589 | 308 |
| Brown, Dan (IV)(SubQ) | | 701112 | 506 |
| Brown, Paul (IV)(SubQ) | | 709895 | 404 |
| Burchfield, John (IV)(SubQ) | | 712544 | 412 |

FIG. 2C

Patient Details (IntraveNous) — 116,146

- Name: John Doe  Room: 302 (ER)
- Patient ID: 7045162  Date of Birth: 4/10/1938  — 208a 230, 230a:
- Last BG: 152 mg/dl (Jones, Sue)
- Last Insulin Rate: 5.4 units/hr
- Target Range: 90-120 mg/dl
- Next BG Due: 7/21/2013 at 15:16

Next BG Due: BG DUE! — 430

(3 Minutes Late) — 432

Alarm Off — 434

FIG. 4B

Patient Details (Subcutaneous) — 116,146

- Name: John Doe  Room: 302 (ER)
- Patient ID: 7045162  Date of Birth: 4/10/1938 — 208a 230, 230b:
- Basal Insulin: Lantus
- Insulin Type: Novolog
- Last BG: 151 mg/dl (Jones, Sue)
- BG Type: Dinner
- Basal Dose: 15 units (1 dose per day)
- Next Meal Dose: 5 units Next BG Due: Pre-Lunch — 430

Alarm On — 434

FIG. 4C

Intravenous: BG Entry — 116,146

Name: John Doe  Room: 302 (ER)
Patient ID: 7045162  Date of Birth: 4/10/1938  — 208a Please enter the current blood glucose value Enter BG Value: ☐ mg/dl
Re-Enter BG Value: ☐ mg/dl
Is this a pre-meal BG?  ● Yes  ○ No
Meal Plan-Number of Carbs Per Meal: 60

[Cancel] [Continue]

*Caution: Physician order required*

Patient Details (Intravenous) — 116,146

Name: John Doe  Room: 302 (ER)
Patient ID: 7045162  Date of Birth: 4/10/1938  — 208a

| Current Insulin | Last BG |
| 1.2 Units/hr | 119 mg/dl |

| Target Range | Insulin Concentration |
| 90-120 mg/dl | 90-120 mg/dl |

57:33 — 430
[Enter BG] — 436
[Start Meal] — 438

Intravenous Meal bolus: Meal Check ~116,146

Name: John Doe  Room: 302 (ER)
Patient ID: 7045162  Date of Birth: 4/10/1938 — 208a Did the Patient Eat?

○ Yes  ● No

[Cancel] [Continue]

FIG. 5C

Intravenous Meal bolus: Meal Check ~116,146

Name: John Doe  Room: 302 (ER)
Patient ID: 7045162  Date of Birth: 4/10/1938 — 208a Did the Patient Eat?

● Yes  ○ No

How much did the Patient eat?

○ 25% of Meal    ○ 50% of Meal
○ 75% of Meal    ○ 100% of Meal
○ Actual Number of Carbs: [    ]

[Cancel] [Continue]

FIG. 5D

Transition Guidance — 116, 146

Name: John Doe    Room: 302 (ER)
Patient ID: 7045162    Date of Birth: 4/10/1938 — 208a Transition Patient to SubQ

Warning:
The BG of the patient has not been in the Target Range for the required 2.5 hours.

Are you sure you want to continue?

[Cancel]  [Yes]

*Caution: Physician order required*

FIG. 6C

Post-Transition Plan — 116, 146

Name: John Doe    Room: 302 (ER)
Patient ID: 7045162    Date of Birth: 4/10/1938 — 208a After SubQ Transition:

○ Continue patient on Glucommander SubQ

○ Discontinue patient from Glucommander

[Cancel]  [Save]

*Caution: Physician order required*

FIG. 6D

Transition Dosing Plan — 116, 146

Name: John Doe   Room: 302 (ER)
Patient ID: 7045162   Date of Birth: 4/10/1938   — 208a After SubQ Transition:
○ Continue patient on SubQ
○ Discontinue

617 —

Orderset Type: [Basal/Bolus + Correction ▼]

Diabetes: [Yes ▼]   Basal Insulin: [Lantus ▼]

Basal % of TDD: [50% ▼]   Daily Basal Distribution: [1 Dose Per Day ▼]

Bolus % of TDD: [50% ▼]   Basal Time: [00:00 ▼]

Bolus Insulin: [Novolog ▼]   [Cancel] [Save]

*Caution: Physician order required*

Transition: Start Basal — 116, 146

Name: John Doe   Room: 302 (ER)
Patient ID: 7045162   Date of Birth: 4/10/1938   — 208a Transition Patient to SubQ Inject Patient With:   Give Now ○
5 Units of Lantus
Modify Dose   Give Later ○

WARNING:
Do Not D/C insulin. System will prompt for hourly blood glucose checks...

[Cancel] [Save]

*Caution: Physician order required*

FIG. 6F

Transition Patient to SUBQ  ⌒116,146

Name: John Doe       Room: 302 (ER)       — 208a
Patient ID: 7045162  Date of Birth: 4/10/1938

Transition Patient to SubQ

Discontinue IV Insulin    ○

WARNING:
Patient is stable. Discontinue IV insulin to prevent hypoglycemia.

Note: Make sure potassium (K) is greater than 4.0...

[ Cancel ]  [ Save ]

*Caution: Physician order required*

FIG. 6G

Accessory: Correction Boluses

Adjustment Factor (AF) Function

SubQ: Subcutaneous Insulin (standard program)

New SubQ Patient, Transitioned from IV

Name: John Doe  Room: 302 (ER)  Diabetes: Yes ▼
Patient ID: 7045162  Date of Birth: 4/10/1938

This patient has been Transitioned from Glucommander IV:
○ Continue patient on Glucommander SubQ
○ Discontinue patient.

Orderset Type: Basal/Bolus + Correction ▼   TDD: 54 units
Bolus Insulin: Novolog ▼   Basal Insulin: Lantus ▼
Meal Bolus % of TDD: 50% ▼   Basal % of TDD: 50% ▼
Daily Meal Bolus Distribution:   Daily Basal Distribution: 1 Dose Per Day ▼
  Breakfast Bolus: 9 units   Basal Dose: 27 units
  Lunch Bolus: 9 units   Basal Time: 21:00 ▼
  Dinner Bolus: 9 units
*Caution: Physician order required*   [Cancel] [Save]

FIG. 9C

New SubQ Patient, Custom Start

Name: John Doe  Room: 302 (ER)  Diabetes: Yes ▼
Patient ID: 7045162  Date of Birth: 4/10/1938

Custom start of patient on Glucommander SubQ:

Orderset Type: Basal/Bolus + Correction ▼   TDD: 54 units
Bolus Insulin: Novolog ▼   Basal Insulin: Lantus ▼
Meal Bolus % of TDD: 50% ▼   Basal % of TDD: 50% ▼
Daily Meal Bolus Distribution:   Daily Basal Distribution: 1 Dose Per Day ▼
  Breakfast Bolus: 9 units   Basal Dose: 27 units
  Lunch Bolus: 9 units   Basal Time: 21:00 ▼
  Dinner Bolus: 9 units
*Caution: Physician order required*   [Cancel] [Save]

FIG. 9D

SubQ Patient, Weight-based Start ~116, 146

208a
- Name: John Doe | Room: 302 (ER) | Diabetes: Yes
- Patient ID: 7045162 | Date of Birth: 4/10/1938

Weight-Based start: Weight(kg) 108

617
- Orderset Type: Basal/Bolus + Correction ▼ | TDD: 54 units
- Bolus Insulin: Novolog ▼ | Basal Insulin: Lantus ▼
- Meal Bolus % of TDD: 50% ▼ | Basal % of TDD: 50% ▼
- Daily Meal Bolus Distribution: | Daily Basal Distribution: 1 Dose Per Day ▼
- Breakfast Bolus: 9 units | Basal Dose: 27 units
- Lunch Bolus: 9 units | Basal Time: 21:00 ▼
- Dinner Bolus: 9 units

*Caution: Physician order required*

[Cancel] [Save]

FIG. 9E

SubQ for Tube-Fed

Meal-by-Meal Subcutaneous Program without Carb-counting

Meal-by-Meal Subcutaneous Program without Carb-counting

Meal-by-Meal Subcutaneous Program with Carbohydrate Counting

Meal-by-Meal Subcutaneous Program with Carbohydrate Counting

SubQ Non-Diabetic

SubQ Non-Diabetic

INSULIN MANAGEMENT

CROSS REFERENCE TO RELATED APPLICATIONS

This U.S. patent application is a continuation of, and claims priority under 35 U.S.C. § 120 from, U.S. patent application Ser. No. 14/938,997, filed on Nov. 12, 2015, which is a divisional under 35 U.S.C. § 121 of U.S. patent application Ser. No. 14/524,918, filed on Oct. 27, 2014, which claims priority under 35 U.S.C. § 119(e) to U.S. Provisional Application 61/934,300, filed on Jan. 31, 2014, and U.S. Provisional Application 62/009,575, filed on Jun. 9, 2014. The disclosures of these prior applications are considered part of the disclosure of this application and are hereby incorporated by reference in their entireties.

TECHNICAL FIELD

This disclosure relates to a system for managing insulin administration or insulin dosing.

BACKGROUND

Today, nearly 40% of patients admitted to acute care hospitals in the United States experience either hyperglycemia or hypoglycemia, both serious medical conditions. Many of these patients have diabetes while others have fluctuating blood sugars due to trauma, drug reactions, stress and other factors. Nurses and doctors managing these patients manually calculate insulin doses using complex paper protocols.

Manual calculation may not be accurate due to human error, which can lead to patient safety issues. Different institutions use multiple and sometimes conflicting protocols to manually calculate an insulin dosage. Moreover, the protocols may include extra paperwork that nurses and physicians have to manage, which in turn leads to workflow inefficiencies, additional operating costs, and employee satisfaction issues. SCIP (Surgical Care Improvement Project) scores, length of stay, readmission and even mortality rates adversely affect sub-optimal glycemic management.

The prevalent method of regulating continuous intravenous insulin infusion is by using a set of written instructions, known as a paper protocol. Paper protocols often involve a tree of conditional statements and some use of tables of numbers, for which a given blood glucose value dictates the use of a different column of insulin rates. The complexity of these paper protocols multiplies the probability of error by the nurses using them. These errors can lead to hypoglycemic events.

SUMMARY

One aspect of the disclosure provides a method of administering insulin. The method includes receiving blood glucose measurements of a patient at a data processing device from a glucometer. The blood glucose measurements are separated by a time interval. The method also includes receiving patient information at the data processing device. The method includes selecting, using the data processing device, a subcutaneous insulin treatment from a collection of subcutaneous insulin treatments. The selection is based on the blood glucose measurements and the patient information. The selected subcutaneous insulin treatment includes one or more of a subcutaneous standard program, a subcutaneous program without meal boluses, a meal-by-meal subcutaneous program without carbohydrate counting, a meal-by-meal subcutaneous program with carbohydrate counting, and a subcutaneous program for non-diabetic patients. The subcutaneous standard program includes determining a blood glucose type of the received blood glucose measurement using the data processing device and determining a correction insulin dose based on the blood glucose type using the data processing device. The method also includes executing, using the data processing device, the selected subcutaneous insulin treatment.

Implementations of the disclosure may include one or more of the following optional features. In some implementations, the method includes receiving a governing blood glucose value, and determining an adjustment factor based on the received governing blood glucose value. Determining the adjustment factor may include determining when the governing blood glucose value is within a threshold range of values, and setting the adjustment factor to a preconfigured adjustment factor based on the threshold range of values. In some implementations, the method includes determining a Carbohydrate-to-Insulin Ratio based on the adjustment factor. The blood glucose type is associated with a blood glucose time associated with a time of measuring the blood glucose measurement. The blood glucose type is selected from the group consisting of: a pre-breakfast blood glucose measurement, a pre-lunch blood glucose measurement, a pre-dinner blood glucose measurement, a bedtime blood glucose measurement, a midsleep blood glucose measurement and a miscellaneous blood glucose measurement.

In some examples, the method includes determining, using the data processing device, if a breakfast blood glucose measurement has been received at the data processing device from the glucometer. When the breakfast blood glucose measurement has been received, the method includes selecting, using the data processing device, a governing blood glucose as a lesser one of a previous midsleep blood glucose measurement or the breakfast blood glucose measurement. The method further includes determining, using the data processing device, an adjustment factor for adjusting a current day's recommended basal dose based on the selected governing blood glucose measurement and retrieving, by the data processing device, a previous day's bed time recommended basal dose. The method further includes determining, by the data processing device, the current day's recommended basal dose by multiplying the adjustment factor times the previous day's bed time recommended basal dose. The current day's recommended basal dose corresponds to an insulin dose of long-acting insulin to be administered to the patient at a configurable frequency of one, two, or three times per day. When the breakfast blood glucose measurement has not been received, the method includes blocking, using the data processing device, a basal dose recommendation and transmitting a warning from the data processing device to a display in communication with the data processing device. The warning indicates the blocked basal dose recommendation.

The method further includes receiving, at the data processing device, a breakfast blood glucose measurement from the glucometer and selecting, using the data processing device, a governing blood glucose as one of a previous midsleep blood glucose measurement and the received breakfast blood glucose measurement. The method also includes, determining, using the data processing device, and adjustment factor for adjusting a current day's recommended basal dose based on the selected governing blood glucose measurement and retrieving, by the data processing device, a previous day's bed time recommended basal dose.

The method further includes determining, by the data processing device, the current day's recommended basal dose by multiplying the adjustment factor times the previous day's bed time recommended basal dose. The current day's recommended basal dose corresponds to an insulin dose of long-acting insulin to be administered to the patient at a configurable frequency of one, two, or three times per day. The governing blood glucose is selected as the previous midsleep blood glucose measurement when the previous midsleep blood glucose measurement is less than the breakfast blood glucose measurement. The governing blood glucose is selected as the breakfast blood glucose measurement when the breakfast blood glucose measurement is less than the previous midsleep blood glucose measurement unless the previous midsleep blood glucose measurement was accompanied by a correction insulin dose exceeding three units of insulin, and an elapsed time between the correction insulin dose and the breakfast blood glucose measurement is less than three hours.

When the determined blood glucose type is one of a breakfast blood glucose measurement, a lunch blood glucose measurement, or a dinner blood glucose measurement, the method includes determining, using the data processing device, an adjustment factor for adjusting a next day's recommended meal bolus at a time of day associated with the determined blood glucose type based upon the subsequent blood glucose measurement, after a subsequent blood glucose measurement associated with a subsequent blood glucose type is received. The method also includes determining, by the data processing device, the next day's recommended meal bolus at the time of day associated with the determined blood glucose type by multiplying the current day's recommended meal bolus associated with the determined blood glucose type times the adjustment factor.

The subcutaneous program for non-diabetic patients includes, for each blood glucose measurement received by the data processing device from the glucometer that is less than or equal to a threshold value, determining, using the data processing device, new currently-recommended insulin doses by multiplying all currently-recommended insulin doses by a dose reduction factor including a value less than one. The method includes recalculating, using the data processing device, a total daily dose of insulin as a sum of all the new currently-recommended insulin doses. The subcutaneous meal-by-meal without carb-counting program includes determining, using the data processing device, a recommended bolus for use throughout the day. For each meal, the method includes adjusting the meal bolus, using the data processing device, by multiplying an immediately previous recommended meal bolus times an adjustment factor governed by a blood glucose measurement received after an immediately previous meal associated with the immediately previous recommended meal bolus. The subcutaneous meal-by-meal with carb-counting program includes determining, using the data processing device, a carbohydrate-insulin ratio for use throughout the day. For each meal, the method includes adjusting the carbohydrate-insulin ratio, using the data processing device, by dividing an immediately previous carbohydrate-insulin ratio associated with an immediately previous meal by an adjustment factor governed by a blood glucose measurement received after the immediately previous meal.

The method further includes transmitting the selected subcutaneous insulin treatment to an administration device in communication with the data processing device. The administration device includes a doser and an administration computing device in communication with the doser. The administration computing device, when executing the selected subcutaneous insulin treatment, causes the doser to administer insulin specified by the selected subcutaneous insulin treatment. The administration device includes at least one of an insulin injection pen or an insulin pump.

Another aspect of the disclosure provides a system for administering insulin. The system includes a glucometer measuring blood glucose measurements separated by a time interval and a dosing controller in communication with the glucometer. The dosing controller includes a data processing device and non-transitory memory in communication with the data processing device. The dosing controller receives blood glucose measurements of a patient from the glucometer and receives patient information. The dosing controller further selects a subcutaneous insulin treatment from a collection of subcutaneous insulin treatments based on the blood glucose measurements and the patient information. The selected subcutaneous insulin treatment includes one or more of a subcutaneous standard program, a subcutaneous program without meal boluses, a meal-by-meal subcutaneous program without carbohydrate counting, and a subcutaneous program for non-diabetic patients. During the standard subcutaneous program, the dosing controller determines a blood glucose type of the received blood glucose measurement and determines a correction insulin dose based on the blood glucose type. The dosing controller further includes executing the selected subcutaneous insulin treatment.

In some examples, the dosing controller receives a governing blood glucose value and determines an adjustment factor based on the received governing blood glucose value. The dosing controller determines the adjustment factor by determining when the governing blood glucose value is within a threshold range of values and sets the adjustment factor to a pre-configured adjustment factor based on the threshold range of values. The dosing controller further determines the adjustment factor by determining the governing blood glucose value is within one of multiple pre-configured ranges of values and sets the adjustment factor to a pre-configured adjustment factor associated with the pre-configured range of values that includes the governing blood glucose value. In some examples, the dosing controller determines a carbohydrate-to-insulin ratio.

The blood glucose type is associated with a blood glucose time associated with a time of measuring the blood glucose measurement. The blood glucose type is selected from the group consisting of: a pre-breakfast blood glucose measurement, a pre-lunch blood glucose measurement, a pre-dinner blood glucose measurement, a bedtime blood glucose measurement, a midsleep blood glucose measurement and a miscellaneous blood glucose measurement.

In some implementations, the dosing controller determines if a breakfast blood glucose measurement has been received at the data processing device from the glucometer. When the breakfast blood glucose measurement has been received, the dosing controller selects a governing blood glucose as a lesser one of a previous midsleep blood glucose measurement or the breakfast blood glucose measurement. The dosing controller further determines an adjustment factor for adjusting a current day's recommended basal dose based on the selected governing blood glucose measurement, retrieves a previous day's bed time recommended basal dose and determines the current day's recommended basal dose by multiplying the adjustment factor times the previous day's bed time recommended basal dose. The current day's recommended basal dose corresponds to an insulin dose of long-acting insulin to be administered to the patient at a configurable frequency of tone, two, or three times per day. When the breakfast blood glucose measurement has not been received, the dosing controller blocks a basal dose recommendation and transmits a warning to a display in communication with the dosing controller. The warning indicates the blocked basal dose recommendation.

In some examples, the dosing controller receives a breakfast blood glucose measurement from the glucometer and selects a governing blood glucose as one of a previous midsleep blood glucose measurement or the received breakfast blood glucose measurement. The dosing controller also determines an adjustment factor for adjusting a current day's recommended basal dose based on the selected governing blood glucose measurement and retrieves a previous day's bed time recommended basal dose. The dosing controller further determines the current day's recommended basal dose by multiplying the adjustment factor times the previous day's bed time recommended basal dose. The current day's recommended basal dose corresponds to an insulin dose of long-acting insulin to be administered to the patient at a configurable frequency of one, two, or three times per day. The governing blood glucose is selected as the previous midsleep blood glucose measurement when the previous midsleep blood glucose measurement is less than the breakfast blood glucose measurement. The governing blood glucose is selected as the breakfast blood glucose measurement when the breakfast blood glucose measurement is less than the previous midsleep blood glucose measurement unless the previous midsleep blood glucose measurement was accompanied by a correction insulin dose exceeding three units of insulin and an elapsed time between the correction insulin dose and the breakfast blood glucose measurement is less than three hours.

When the determined blood glucose type is one of a breakfast blood glucose measurement, a lunch blood glucose measurement, or a dinner blood glucose measurement, after a subsequent blood glucose measurement associated with a subsequent blood glucose type is received, the dosing controller determines an adjustment factor for adjusting a next day's recommended meal bolus at a time of day associated with the determined blood glucose type based upon the subsequent blood glucose measurement. The dosing controller further determines the next day's recommended meal bolus at the time of day associated with the determined blood glucose type by multiplying the current day's recommended meal bolus associated with the determined blood glucose type times the adjustment factor.

During the subcutaneous program for non-diabetic patients, the dosing controller determines a new currently-recommended insulin doses by multiplying all currently-recommended insulin doses by a dose reduction factor including a value less than one and recalculates a total daily dose of insulin as a sum of all the new currently-recommended insulin doses, for each blood glucose measurement received by the dosing controller from the glucometer that is less than or equal to a threshold value. During the subcutaneous meal-by-meal without carb-counting program, the dosing controller determines a recommended meal bolus for use throughout the day. For each meal, the system adjusts the meal bolus by multiplying an immediately previous recommended meal bolus times and adjustment factor governed by a blood glucose measurement received after an immediately previous meal associated with the immediately previous recommended meal bolus. During the subcutaneous meal-by-meal with carb-counting program, the dosing controller determines a carbohydrate-insulin ratio for use throughout the day. For each meal, the system adjust the carbohydrate-insulin ratio by dividing an immediately previous carbohydrate-insulin ratio associated with an immediately previous meal by an adjustment factor governed by a blood glucose measurement received after the immediately previous meal.

In some examples, the dosing controller transmits the selected subcutaneous insulin treatment to an administration device in communication with the dosing controller. The administration device includes a doser and an administration computing device in communication with the doser. The administration computing device, when executing the selected subcutaneous insulin treatment, causes the doser to administer insulin specified by the selected subcutaneous insulin treatment. The administration device includes at least one of an insulin injection pen or an insulin pump.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2B is a schematic view of an exemplary display for inputting patient information.

FIG. 2C is a schematic view of an exemplary display for selecting a patient from a list of patients.

FIGS. 4B and 4C are schematic views of an exemplary display showing the time a next blood glucose measurement is due.

FIG. 4D is a schematic view of an exemplary display for inputting patient information.

FIG. 4E is a schematic view of an exemplary display of patient information and a timer for a patient's next blood glucose measurement.

FIGS. 5C and 5D are schematic views of exemplary displays requesting information from the user.

FIG. 6C is a schematic view of an exemplary warning to the user relating to the patient.

FIG. 6D is a schematic view of an exemplary display inquiring whether the patient should continue treatment or stop.

FIG. 6E is a schematic view of an exemplary display requesting information from the user relating to the patient.

FIG. 6F is a schematic view of an exemplary display showing the recommended dose of insulin.

FIG. 6G is a schematic view of an exemplary view to the user relating to transitioning a patient to subcutaneous delivery.

FIGS. 9C-9E are schematic views of exemplary displays requesting information from the user relating to the patient.

Like reference symbols in the various drawings indicate like elements.

DETAILED DESCRIPTION

Diabetic hospital patients who eat meals often have poor appetites; consequently, co-ordination of meal boluses and meals is difficult. Meal boluses without meals cause hypoglycemia; meals without meal boluses cause hyperglycemia. Different providers may use different methods of adjusting doses: some may use formulas of their own; some may use paper protocols that are complex and difficult for the nurse to follow, leading to a high incidence of human error; and some may use heuristic methods. There is no guarantee of consistency. Moreover, for diabetic patients who do not eat meals, there is no currently no computerized method of tracking the patient's status. For non-diabetic patient who get include due to "stress hyperglycemia" when they are very sick or undergoing surgery, there is no current method of monitoring their recovery when the stress subsides and their need for insulin rapidly decreases. If the dose regimen does not decrease rapidly also, hypoglycemia may result. Therefore, it is desirable to have a clinical support system 100 (FIGS. 1A and 1B) that monitors patients' blood glucose level.

Figure 1A:
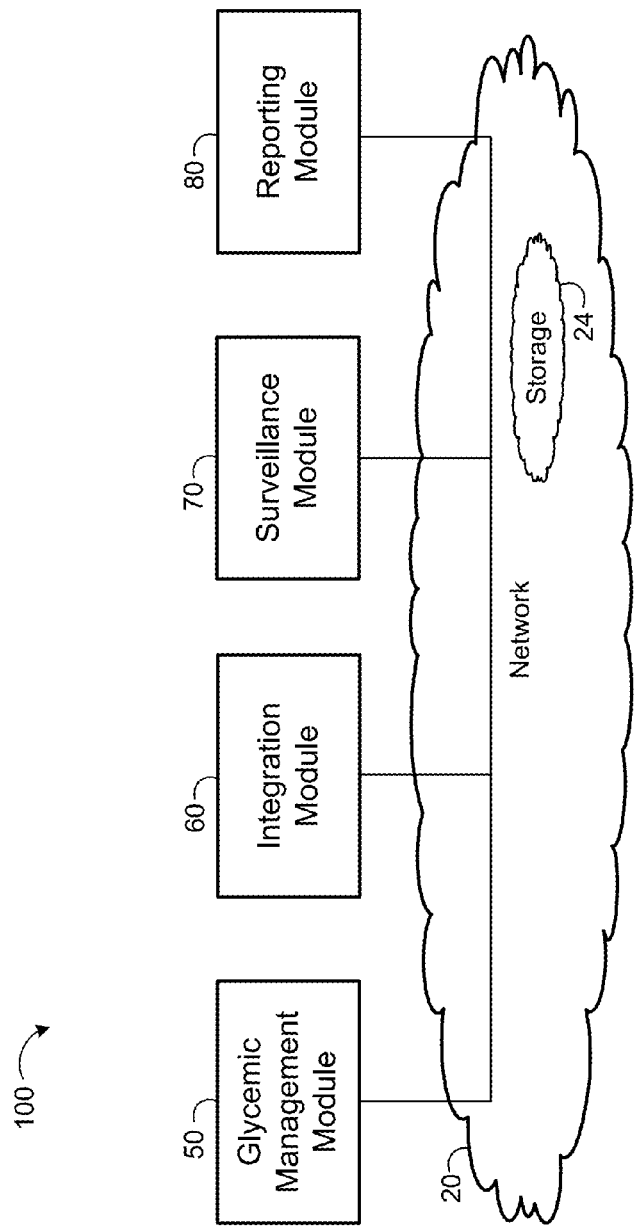
FIG. 1A is a schematic view of an exemplary system for monitoring blood glucose level of a patient.
Figure 1B:
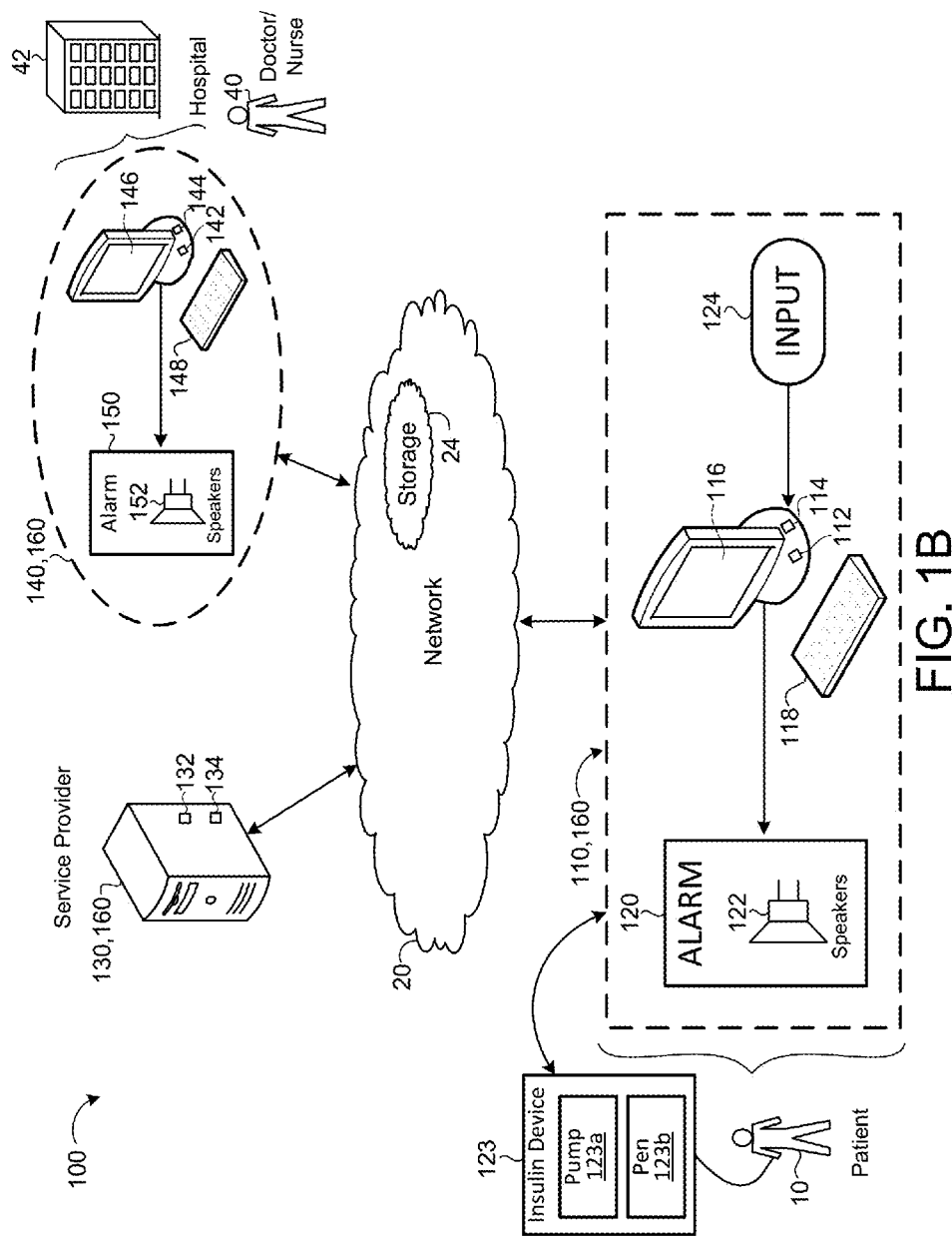
FIG. 1B is a schematic view of an exemplary system for monitoring blood glucose level of a patient.
Figure 1C:
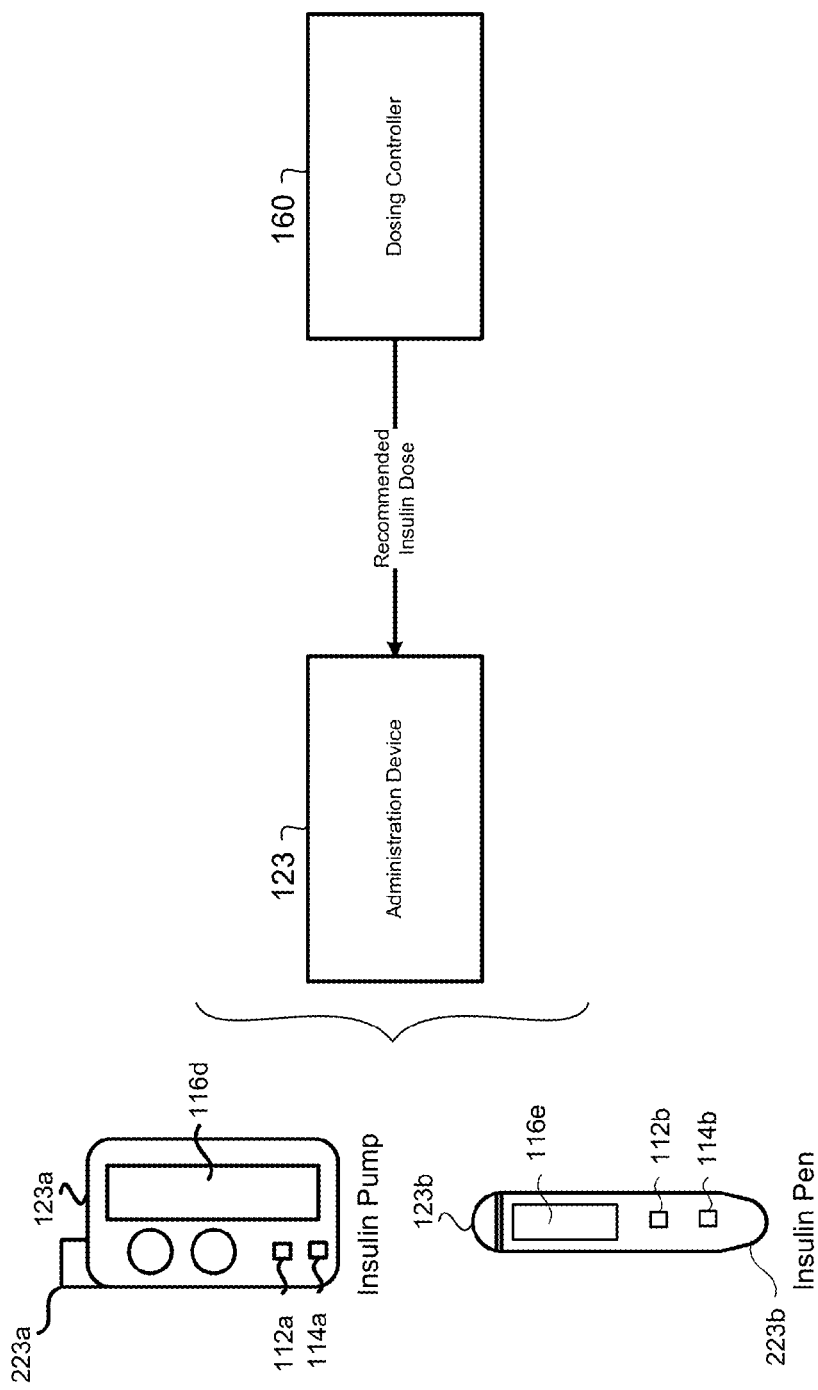
FIG. 1C is a schematic view of an exemplary administration device in communication with a dosing controller.

Referring to FIG. 1A-1C, in some implementations, a clinical decision support system 100 analyzes inputted patient condition parameters for a patient 10 and calculates a personalized dose of insulin to bring and maintain the patient's blood glucose level into a target range $BG_{TR}$. Moreover, the system 100 monitors the glucose levels of a patient 10 and calculates recommended intravenous or subcutaneous insulin dose to bring the patient's blood glucose into the preferred target range $BG_{TR}$ over a recommended period of time. A qualified and trained healthcare professional 40 may use the system 100 along with clinical reasoning to determine the proper dosing administered to a patient 10. Therefore, the system 100 is a glycemic management tool for evaluation a patient's current and cumulative blood glucose value BG while taking into consideration the patient's information such as age, weight, and height. The system 100 may also consider other information such as carbohydrate content of meals, insulin doses being administered to the patient 10, e.g., long-acting insulin doses for basal insulin and rapid-acting insulin doses for meal boluses and correction boluses. Based on those measurements (that may be stored in non-transitory memory 24, 114, 144), the system 100 recommends an intravenous dosage of insulin, glucose, or saline or a subcutaneous basal and bolus insulin dosing recommendation or prescribed dose to adjust and maintain the blood glucose level towards a configurable (based on the patient's information) physician's determined blood glucose target range $BG_{TR}$. The system 100 also considers a patient's insulin sensitivity or improved glycemic management and outcomes. The system 100 may take into account pertinent patient information such as demographics and previous results, leading to a more efficient use of healthcare resources. Finally, the system 100 provides a reporting platform for reporting the recommendations or prescribed dose(s) to the user 40 and the patient 10. In addition, for diabetic patients who eat meals, the system 100 provides faster, more reliable, and more efficient insulin administration than a human monitoring the insulin administration. The system 100 reduces the probability of human error and insures consistent treatment, due to the system's capability of storing and tracking the patient's blood glucose levels BG, which may be used for statistical studies. As for patients who are tube-fed or do not eat meals, the system 100 provides dedicated subprograms, which in turn provide basal insulin and correction boluses but no meal boluses. Patients who are tube-fed or who do not eat usually have a higher basal insulin level than patients who eat, because the carbohydrates in the nutritive formula are accounted-for in the basal insulin. The system 100 provides a meal-by-meal adjustment of Meal Boluses without carbohydrate counting, by providing a dedicated subprogram that adjusts meal boluses based on the immediately preceding meal bolus and the BG that followed it. The system 100 provides a meal-by-meal adjustment of Meal Boluses with carbohydrate counting by providing a dedicated subprogram that adjusts meal boluses based a Carbohydrate-to-Insulin Ratio (CIR) that is adjusted at each meal, based on the CIR used at the immediately preceding meal bolus and the BG that followed it.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's blood glucose level is below a preferred target. Appropriate management of blood glucose levels for critically ill patients reduces co-morbidities and is associated with a decrease in infection rates, length of hospital stay, and death. The treatment of hyperglycemia may differ depending on whether or not a patient has been diagnosed with Type 1 diabetes mellitus, Type 2 diabetes mellitus, gestational diabetes mellitus, or non-diabetic stress hyperglycemia. The blood glucose target range $BG_{TR}$ is defined by a lower limit, i.e., a low target $BG_{TRL}$ and an upper limit, i.e., a high target $BG_{TRH}$.

Stress-related hyperglycemia: Patients often get "stress hyperglycemia" if they are very sick or undergoing surgery. This condition requires insulin. In diabetic patients, the need for insulin is visibly increased. In non-diabetic patients, the stress accounts for the only need for insulin, and as the patients recover, the stress subsides, and their need for insulin rapidly decreases. For non-diabetic patients, the concern is that their need for insulin decreases faster than their dose regimen, leading to hypoglycemia.

Diabetes Mellitus has been treated for many years with insulin. Some recurring terms and phrases are described below:

Injection: Administering insulin by means of manual syringe or an insulin "pen," with a portable syringe named for its resemblance to the familiar writing implement.

Infusion: Administering insulin in a continuous manner by means of an insulin pump for subcutaneous insulin or an intravenous apparatus 123a, both of which are capable of continuous administration.

Intravenous Insulin Therapy: Intravenous infusion of insulin has been approved by the U.S. Food and Drug Administration as an acceptable indication for use. Intravenous infusion is the fastest of all insulin administration routes and, typically, only available in the hospital setting. For instance, in intensive care units, the patients may be fed by intravenous glucose infusion, by intravenous Total Parenteral Nutrition (TPN), or by a tube to the stomach. Patients are often given insulin in an intravenous infusion at an insulin infusion rate IIR. The IIR is regulated by the frequent testing of blood glucose, typically at intervals between about 20 minutes and 2 hours. This is combined with a protocol in which a new IIR is computed after each blood glucose test.

Basal-Bolus Therapy: Basal-bolus therapy is a term that collectively refers to any insulin regimen involving basal insulin and boluses of insulin.

Basal Insulin: Insulin that is intended to metabolize the glucose released by a patient's the liver during a fasting state. Basal insulin is administered in such a way that it maintains a background level of insulin in the patient's blood, which is generally steady but may be varied in a programmed manner by an insulin pump 123a. Basal insulin is a slow, relatively continuous supply of insulin throughout the day and night that provides the low, but present, insulin concentration necessary to balance glucose consumption (glucose uptake and oxidation) and glucose production (glucogenolysis and gluconeogenesis). A patient's Basal insulin needs are usually about 10 to 15 mU/kg/hr and account for 30% to 50% of the total daily insulin needs; however, considerable variation occurs based on the patient 10.

Bolus Insulin: Insulin that is administered in discrete doses. There are two main types of boluses, Meal Bolus and Correction Bolus.

Meal Bolus: Taken just before a meal in an amount which is proportional to the anticipated immediate effect of carbohydrates in the meal entering the blood directly from the digestive system. The amounts of the Meal Boluses may be determined and prescribed by a physician 40 for each meal during the day, i.e., breakfast, lunch, and dinner. Alternatively, the Meal Bolus may be calculated in an amount generally proportional to the number of grams of carbohydrates in the meal. The amount of the Meal Bolus is calculated using a proportionality constant, which is a personalized number called the Carbohydrate-to-Insulin Ratio (CIR) and calculated as follows:

$$\text{Meal Insulin Bolus} = \{\text{grams of carbohydrates in the meal}\}/\text{CIR} \quad (1)$$

Correction Bolus CB: Injected immediately after a blood glucose measurement; the amount of the correction bolus is proportional to the error in the BG (i.e., the bolus is proportional to the difference between the blood glucose measurement BG and the patient's personalized Target blood glucose $BG_{Target}$). The proportionality constant is a personalized number called the Correction Factor, CF, and is calculated as follows:

$$CB = (BG - BG_{Target})/CF \quad (2)$$

A Correction Bolus CB is generally administered in a fasting state, after the previously consumed meal has been digested. This often coincides with the time just before the next meal.

There are several kinds of Basal-Bolus insulin therapy including Insulin Pump therapy and Multiple Dose Injection therapy:

Insulin Pump Therapy: An insulin pump 123a is a medical device used for the administration of insulin in the treatment of diabetes mellitus, also known as continuous subcutaneous insulin infusion therapy. The device includes: a pump, a disposable reservoir for insulin, and a disposable infusion set. The pump 123a is an alternative to multiple daily injections of insulin by insulin syringe or an insulin pen and allows for intensive insulin therapy when used in conjunction with blood glucose monitoring and carbohydrate counting. The insulin pump 123a is a battery-powered device about the size of a pager. It contains a cartridge of insulin, and it pumps the insulin into the patient via an "infusion set", which is a small plastic needle or "canula" fitted with an adhesive patch. Only rapid-acting insulin is used.

Multiple Dose Injection (MDI): MDI involves the subcutaneous manual injection of insulin several times per day using syringes or insulin pens 123b. Meal insulin is supplied by injection of rapid-acting insulin before each meal in an amount proportional to the meal. Basal insulin is provided as a once, twice, or three time daily injection of a dose of long-acting insulin. Other dosage frequencies may be available. Advances continue to be made in developing different types of insulin, many of which are used to great advantage with MDI regimens:

Long-acting insulins are non-peaking and can be injected as infrequently as once per day. These insulins are widely used for Basal Insulin. They are administered in dosages that make them appropriate for the fasting state of the patient, in which the blood glucose is replenished by the liver to maintain a steady minimum blood glucose level.

Rapid-acting insulins act on a time scale shorter than natural insulin. They are appropriate for boluses.

In some examples, critically ill patients are ordered nil per os (NPO), which means that oral food and fluids are withheld from the patient 10. Typically these patients 10 are unconscious, have just completed an invasive surgical procedure, or generally have difficulty swallowing. Intravenous insulin infusion is typically the most effective method of managing blood glucose levels in these patients. A patient 10 may be NPO and receiving a steady infusion of intravenous glucose, Total Parenteral Nutrition, tube feeding, regular meals that include carbohydrates, or not receiving any nutrition at all. In cases where the patient 10 is not receiving any nutrition, blood glucose is typically replaced by endogenous production by the liver.

As a patient's condition improves, an NPO order may be lifted, allowing the patient 10 to commence an oral caloric intake. In patients 10 with glycemic abnormalities, additional insulin may be needed to cover the consumption of carbohydrates. These patients 10 generally receive one-time injections of insulin in the patient's subcutaneous tissue.

Subcutaneous administration of mealtime insulin in critically ill patients 10 can introduce a patient safety risk if, after receiving the insulin injection, the patient 10 decides not to eat, is unable to finish the meal, or experiences emesis.

Continuous intravenous infusion of mealtime insulin, over a predetermined time interval, allows for an incremental fulfillment of the patient's mealtime insulin requirement, while minimizing patient safety risks. If a patient 10 decides he/she is unable to eat, the continuous intravenous infusion may be stopped or, if a patient 10 is unable to finish the meal, the continuous intravenous infusion rate may be decreased to compensate for the reduction in caloric intake.

The pharmacokinetics (what the body does to a drug over a period of time, which includes the processes of absorption, distribution, localization in tissues, biotransformation, and excretion) and pharmacodynamics (what a drug does to the body) actions of insulin significantly improve when administering insulin via an intravenous route, which is a typical method of delivery for hospitalized patients 10. The management of prandial insulin requirements using an intravenous route can improve patient safety, insulin efficiency, and the accuracy of insulin dosing. The majority of patients who require continuous intravenous insulin infusion therapy may also need to be transitioned to a subcutaneous insulin regimen for ongoing control of blood glucose, regardless of diabetes mellitus (DM) diagnosis. Moreover, the timing, dosing, and process to transition patients 10 from a continuous intravenous route of insulin administration to a subcutaneous insulin regimen is complex and should be individualized based on various patient parameters. Failure to individualize this approach could increase the risk of severe hypoglycemia during the transition process. If not enough insulin is given, the patient 10 may experience acute post-transition hyperglycemia, requiring re-initiation of a continuous intravenous insulin infusion. Therefore, the clinical decision support system 100 calculates a personalized dose of insulin to bring and maintain the patient's blood glucose level into a target range $BG_{TR}$, while taking into consideration the condition of the patient 10.

The clinical decision support system 100 includes a glycemic management module 50, an integration module 60, a surveillance module 70, and a reporting module 80. Each module 50, 60, 70, 80 is in communication with the other modules 50, 60, 70, 80 via a network 20. In some examples, the network 24 (discussed below) provides access to cloud computing resources that allows for the performance of services on remote devices instead of the specific modules 50, 60, 70, 80. The glycemic management module 50 executes a process 200 (e.g., an executable instruction set) on a processor 112, 132, 142 or on the cloud computing resources. The integration module 60 allows for the interaction of users 40 with the system 100. The integration module 60 receives information inputted by a user 40 and allows the user 40 to retrieve previously inputted information stored on a storage system (e.g., one or more of cloud storage resources 24, a non-transitory memory 144 of a hospital's electronic medical system 140, a non-transitory memory 114 of the patient device 110, or other non-transitory storage media in communication with the integration module 60). Therefore, the integration module 60 allows for the interaction between the users 40 and the system 100 via a display 116, 146. The surveillance module 70 considers patient information 208a received from a user 40 via the integration module 60 and information received from a glucometer 124 that measures a patient's blood glucose value BG and determines if the patient 10 is within a threshold blood glucose value $BG_{TH}$. In some examples, the surveillance module 70 alerts the user 40 if a patient's blood glucose values BG are not within a threshold blood glucose value $BG_{TH}$. The surveillance module 70 may be preconfigured to alert the user 40 of other discrepancies between expected values and actual values based on pre-configured parameters (discussed below). For example, when a patient's blood glucose value BG drops below a lower limit of the threshold blood glucose value $BG_{THL}$. The reporting module 80 may be in communication with at least one display 116, 146 and provides information to the user 40 determined using the glycemic management module 50, the integration module 60, and/or the surveillance module 70. In some examples, the reporting module 80 provides a report that may be displayed on a display 116, 146 and/or is capable of being printed.

The system 100 is configured to evaluate a glucose level and nutritional intake of a patient 10. The system 100 also evaluates whether the patient 10 is transitioning to a subcutaneous insulin regime. Based on the evaluation and analysis of the data, the system 100 calculates an insulin dose, which is administered to the patient 10 to bring and maintain the blood glucose level of the patient 10 into the blood glucose target range $BG_{TR}$. The system 100 may be applied to various devices, including, but not limited to, intravenous infusion pumps 123a, subcutaneous insulin infusion pumps 123a, glucometers, continuous glucose monitoring systems, and glucose sensors. In some implementations, as the system 100 is monitoring the patient's blood glucose values BG and the patient's insulin intake, the system 100 notifies the user 40 if the patient 10 receives more than 500 units/hour of insulin because the system 100 considers these patients 10 to be insulin resistant.

In some examples the clinical decision support system 100 includes a network 20, a patient device 110, a dosing controller 160, and a service provider 130. The patient device 110 may include, but is not limited to, desktop computers or portable electronic device (e.g., cellular phone, smartphone, personal digital assistant, barcode reader, personal computer, or a wireless pad) or any other electronic device capable of sending and receiving information via the network 20.

The patient device 110 includes a data processor 112 (e.g., a computing device that executes instructions), and non-transitory memory 114 and a display 116 (e.g., touch display or non-touch display) in communication with the data processor 112. In some examples, the patient device 110 includes a keyboard 118, speakers 120, microphones, mouse, and a camera.

The service provider 130 may include a data processor 132 in communication with non-transitory memory 134. The service provider 130 provides the patient 10 with a process 200 (see FIG. 2) (e.g., a mobile application, a web-site application, or a downloadable program that includes a set of instructions) executable on a processor 112, 132, 142 of the dosing controller 160 and accessible through the network 20 via the patient device 110, intravenous infusion pumps 123a, hospital electronic medical record systems 140, or portable blood glucose measurement devices 124 (e.g., glucose meter or glucometer). Intravenous infusion pumps infuse fluids, medication or nutrients into a patient's circulatory system. Intravenous infusion pumps 123a may be used intravenously and, in some instances, subcutaneous, arterial and epidural infusions are used. Intravenous infusion pumps 123a typically administer fluids that are expensive or unreliable if administered manually (e.g., using a pen 123b) by a nurse or doctor 40. Intravenous infusion pumps 123a can administer a 0.1 ml per hour injection, injections every minute, injections with repeated boluses requested by the patient, up to a maximum number per hours, or fluids whose volumes vary by the time of day.

Figure 2A:
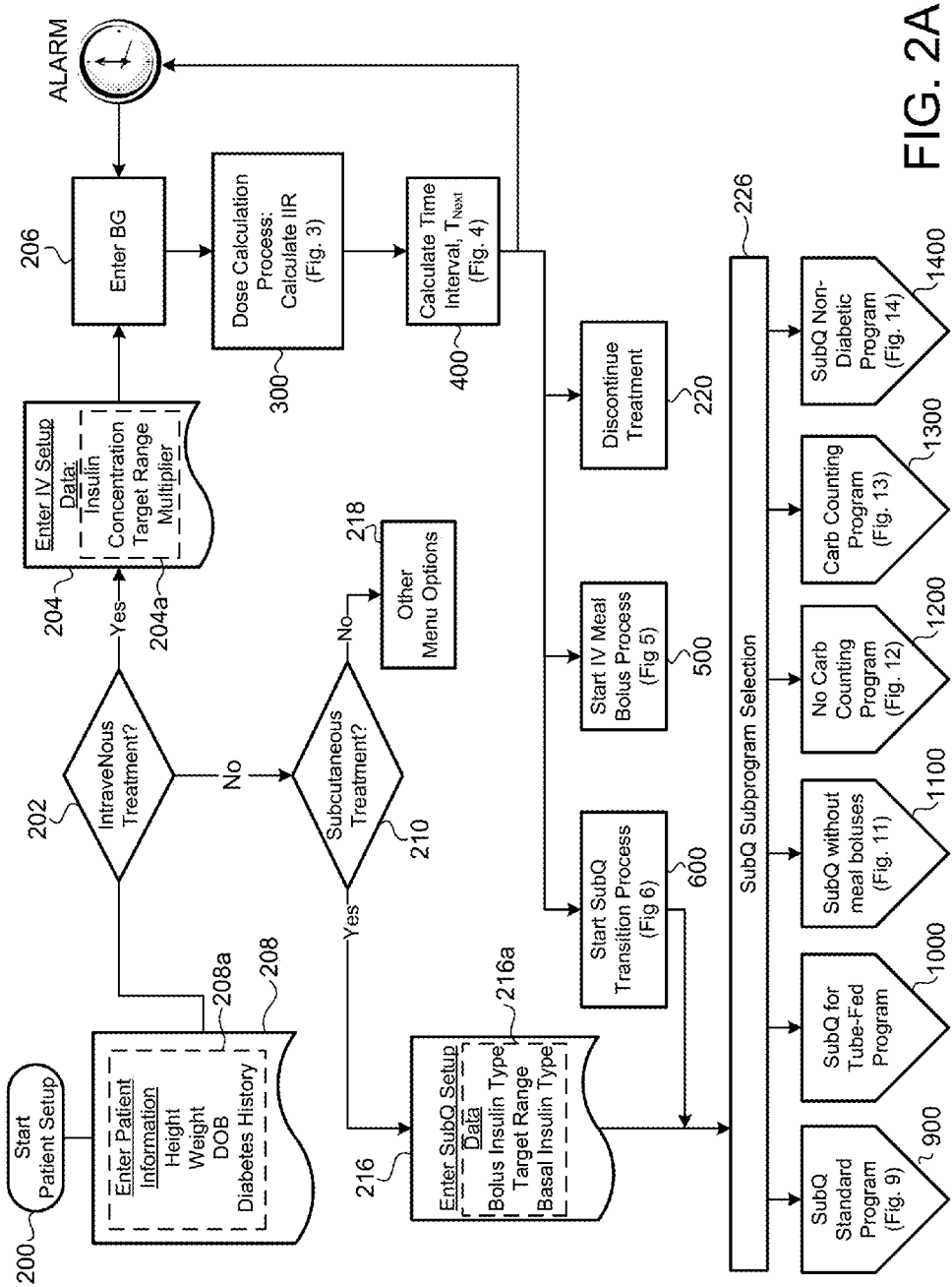
FIG. 2A is a schematic view of an exemplary process for monitoring the blood glucose level of a patient.

In some implementations, an electronic medical record system 140 is located at a hospital 42 (or a doctor's office) and includes a data processor 142, a non-transitory memory 144, and a display 146 (e.g., touch display or non-touch display). The transitory memory 144 and the display 146 are in communication with the data processor 142. In some examples, the hospital electronic medical system 140 includes a keyboard 148 in communication with the data processor 142 to allow a user 40 to input data, such as patient information 208a (FIGS. 2A and 2B). The non-transitory memory 144 maintains patient records capable of being retrieved, viewed, and, in some examples, modified and updated by authorized hospital personal on the display 146.

The dosing controller 160 is in communication with the glucometer 124 and includes a computing device 112, 132, 142 and non-transitory memory 114, 134, 144 in communication with the computing device 112, 132, 142. The dosing controller 160 executes the process 200. The dosing controller 160 stores patient related information retrieved from the glucometer 124 to determine an insulin dose rate IRR based on the received blood glucose measurement BG.

Referring to FIG. 1C, in some implementations, the insulin device 123 (e.g., administration device), in communication with the dosing controller 160, capable of executing instructions for administering insulin according to a subcutaneous insulin treatment program selected by the dosing controller 160. The administration device 123 may include the insulin pump 123a or the pen 123b. The administration device 123 is in communication with the glucometer 124 and includes a computing device 112a, 112b and non-transitory memory 114a, 114b in communication with the computing device 112a, 112b. The administration device 123 includes a doser 223a, 223b in communication with the administration computing device 112a, 112b for administering insulin to the patient. For instance, the doser 223a of the insulin pump 123a includes an infusion set including a tube in fluid communication with an insulin reservoir and a cannula inserted into the patient's 10 body and secured via an adhesive patch. The doser 223b of the pen 123b includes a needle for insertion into the patient's 10 body for administering insulin from an insulin cartridge. The administration device 123 may receive a subcutaneous insulin treatment program selected by and transmitted from the dosing controller 160, while the administration computing device 112a, 112b may execute the subcutaneous insulin treatment program. Executing the subcutaneous insulin treatment program by the administration computing device 112a, 112b causes the doser 223a, 223b to administer doses of insulin specified by the subcutaneous insulin treatment program. For instance, units for the doses of insulin may be automatically set or dialed in by the administration device 123a, 123b and administered via the doser 223a, 223b to the patient 10.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term cloud' services generally refers to a service performed not locally on a user's device, but rather delivered from one or more remote devices accessible via one or more networks 20.

Referring to FIGS. 1B and 2A-2C, the process 200 receives parameters (e.g., patient condition parameters) inputted via the client device 110, the service provider 130, and/or the hospital system 140, analyzes the inputted parameters, and determines a personalized dose of insulin to bring and maintain a patient's blood glucose level BG into a preferred target range $BG_{TR}$.

In some implementations, before the process 200 begins to receive the parameters, the process 200 may receive a username and a password (e.g., at a login screen displayed on the display 116, 146) to verify that a qualified and trained healthcare professional 40 is initiating the process 200 and entering the correct information that the process 200 needs to accurately administer insulin to the patient 10. The system 100 may customize the login screen to allow a user 40 to reset their password and/or username. Moreover, the system 100 may provide a logout button (not shown) that allows the user 40 to log out of the system 100. The logout button may be displayed on the display 116, 146 at any time during the execution of the process 200.

The clinical decision support system 100 may include an alarm system 120 that alerts a user 40 when the patient's blood glucose level BG is outside the target range $BG_{TR}$. The alarm system 120 may produce an audible sound via speaker 122 in the form of a beep or some like audio sounding mechanism. In some examples, the alarm system 120 displays a warning message or other type of indication on the display 116 of the patient device 110 to provide a warning message. The alarm system 120 may also send the audible and/or visual notification via the network 20 to the hospital system 140 (or any other remote station) for display on the display 146 of the hospital system 140 or played through speakers 152 of the hospital system 140.

The process 200 prompts a user 40 to input patient information 208a at block 208. The user 40 may input the patient information 208a, for example, via the user device 110 or via the hospital electronic medical record systems 140 located at a hospital 42 (or a doctor's office). The user 40 may input new patient information 208a as shown in FIG. 2B or retrieve previously stored patient information 208a as shown in FIG. 2C. In some implementations, the process 200 provides the user 40 with a patient list 209 (FIG. 2C) where the user 40 selects one of the patient names from the patient list 209, and the process 200 retrieves that patient's information 208a. The process 200 may allow the user 40 to filer the patient list 209, e.g., alphabetically (first name or last name), by location, patient identification. The process 200 may retrieve the patient information 208a from the non-transitory memory 144 of the hospital's electronic medical system 140 or the non-transitory memory 114 of the patient device 110 (e.g., where the patient information 208a was previously entered and stored). The patient information 208a may include, but is not limited to, a patient's name, a patient's identification number (ID), a patient's height, weight, date of birth, diabetes history, physician name, emergency contact, hospital unit, diagnosis, gender, room number, and any other relevant information. In some examples, the diagnosis may include, but is not limited to, burn patients, Coronary artery bypass patients, stoke patients, diabetic ketoacidosis (DKA) patients, and trauma patients. After the user 40 completes inputting the patient information 208a, the process 200 at block 202 determines whether the patient 10 is being treated with an intravenous treatment module by prompting the user 40 (e.g., on the display 116, 146) to input whether the patient 10 will be treated with an intravenous treatment module. If the patient 10 will not be treated with the intravenous treatment module, the process 200 determines at block 210 whether the patient 10 will be treated with a subcutaneous treatment module, by asking the user 40 (e.g., by prompting the user 40 on the display 116, 146). If the user 40 indicates that the patient 10 will be treated with the subcutaneous treatment, the process 200 flows to block 216, where the user 40 enters patient subcutaneous information 216a, such as bolus insulin type, target range, basal insulin type and frequency of distribution (e.g., 1 dose per day, 2 doses per day, 3 doses per day, etc.), patient diabetes status, subcutaneous type ordered for the patient (e.g., Basal/Bolus and correction that is intended for patients on a consistent carbohydrate diet, or Basal and correction that is intended for patients who are NPO or on continuous enteral feeds), frequency of patient blood glucose measurements, or any other relevant information. In some implementations, the patient subcutaneous information 216a is prepopulated with default parameters, which may be adjusted or modified. When the user 40 enters the patient subcutaneous information 216, the subcutaneous program begins at block 226. The process may determine whether the patient 10 is being treated with an intravenous treatment or a subcutaneous treatment by prompting the user 40 to select between two options (e.g., a button displayed on the display 116, 146), one being the intravenous treatment and the other begin the subcutaneous treatment. In some implementations, the subcutaneous program (at block 226) includes six sub programs: a subcutaneous standard program (FIGS. 9A-9B); a subcutaneous for tube-fed patients program (FIG. 10); a subcutaneous program without meal boluses (FIG. 11); a meal-by-meal subcutaneous program without carbohydrate counting (FIG. 12); a meal-by-meal subcutaneous program with carbohydrate counting (FIGS. 13A-13B); and a subcutaneous program for non-diabetic patients (FIG. 14).

In some implementations and referring back to block 202, if the process 200 determines that the patient 10 will be treated with the intravenous treatment module, the process 200 prompts the user 40 at block 204 for setup data 204a, such as patient parameters 204a relevant to the intravenous treatment mode. In some examples, the patient parameter 204a relating to the intravenous treatment may be prepopulated, for example, with default values that may be adjusted and modified by the user 40. These patient parameters 204a may include an insulin concentration (i.e., the strength of insulin being used for the intravenous dosing, which may be measured in units/milliliter), the type of insulin and rate being administered to the patient, the blood glucose target range $BG_{TR}$, the patient's diabetes history, a number of carbohydrates per meal, or any other relevant information. In some implementations, the type of insulin and the rate of insulin depend on the BG of the patient 10. For example, the rate and type of insulin administered to a patient 10 when the blood glucose value BG of the patient 10 is greater or equal to 250 mgl/dl may be different than the rate and type of insulin administered to the patient 10 when the blood glucose value BG of the patient is greater than 250 ml/dl. The blood glucose target range $BG_{TR}$ may be a configurable parameter, customized based on various patient factors. The blood glucose target range $BG_{TR}$ may be limited to 40 mg/dl (e.g., 100-140 mg/dl, 140-180 mg/dl, and 120-160 mg/dl).

After the user 40 inputs patient parameters 204a for the intravenous treatment at block 204, the process 200 prompts the user 40 to input the blood glucose value BG of the patient 10 at block 206. The blood glucose value BG may be manually inputted by the user 40, sent via the network 20 from a glucometer 124, sent electronically from the hospital information or laboratory system 140, or other wireless device. The process 200 determines a personalized insulin dose rate, referred to as an insulin infusion rate IIR, using the blood glucose value BG of the patient 10 and a dose calculation process 300.

In some implementations, the process 200 executes on the processor 112, 132, 142 the following instruction set. Other instructions are possible as well.

Figure 3:
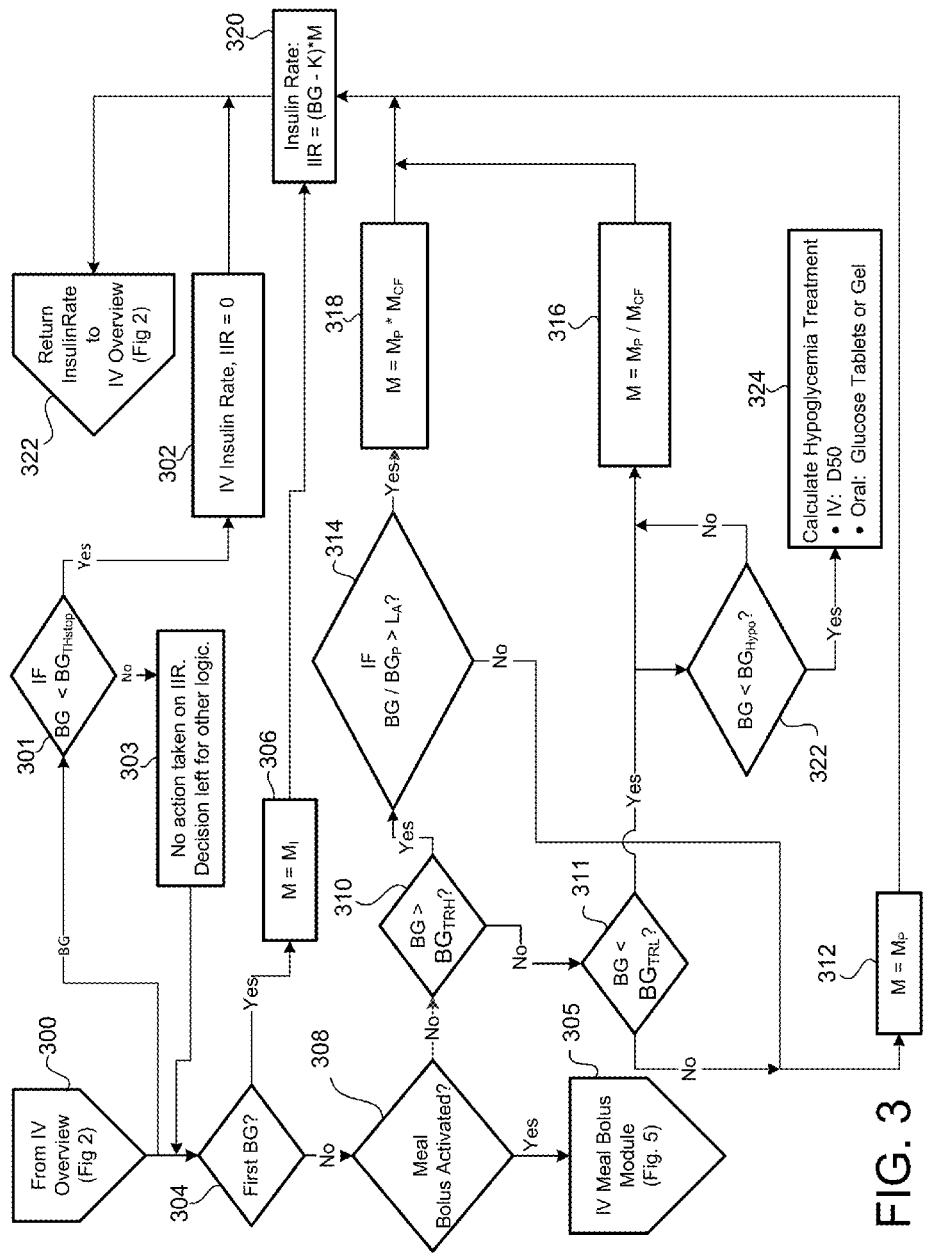
FIG. 3 is a schematic view of an exemplary dose calculation process of FIG. 2A.

FIG. 3 provides a dose calculation process 300 for calculating the insulin infusion rate IIR of the patient 10 for intravenous treatment after the process 200 receives the patient information 208a discussed above (including the patients' blood glucose value BG). At block 301 the dose calculation process 300 determines if the patient's blood glucose BG is less than a stop threshold value $BG_{THstop}$. If not, then at block 303 the dose calculation process 300 goes to block 304 without taking any action. If, however, the patient's blood glucose BG is less than a stop threshold value $BG_{THstop}$, then the calculation dose process sets the patient's regular insulin dose rate IRR to zero at block 302, which then goes to block 322. The dose calculation process 300 determines at decision block 304 if the inputted blood glucose value BG is the first inputted blood glucose value.

The patient's regular insulin dose rate IIR is calculated at block 320 in accordance with the following equation:

$$IIR=(BG-K)*M \quad (3A)$$

where K is a constant, known as the Offset Target, with the same unit of measure as blood glucose and M is a unit-less multiplier. In some examples, the Offset Target K is lower than the blood glucose target range of the patient 10. The Offset Target K allows the dose calculation process 300 to calculate a non-zero stable insulin dose rate even with a blood glucose result is in the blood glucose target range $BG_{TR}$.

The initial multiplier $M_I$, determined by the physician 40, approximates the sensitivity of a patient 10 to insulin. For example, the initial multiplier equals 0.02 for adults ages 18 and above. In some examples, the initial multiplier $M_I$ equals 0.01 for frail elderly patients 10 who may be at risk for complications arising when their blood glucose level BG falls faster than 80 mg/dl/hr. Moreover, the physician 40 may order a higher initial multiplier $M_I$ for patients 10 with special needs, such as CABG patients (i.e., patients who have undergone coronary artery bypass grafting) with BMI (Body Mass Index which is a measure for the human body shape based on the individual's mass and height) less than 30 might typically receive an initial multiplier of 0.05, whereas a patient 10 with BMI greater than 30 might receive an initial multiplier $M_I$ of 0.06. In addition, a patient's weight may be considered in determining the value of the initial multiplier $M_I$, for examples, in pediatric treatments, the system 100 calculates a patient's initial multiplier $M_I$ using the following equation:

$$M_I=0.0002\times\text{Weight of patient (in kilograms)} \quad (3B)$$

In some implementations, K is equal to 60 mg/dl. The dose calculation process 300 determines the target blood glucose target range $BG_{TR}$ using two limits inputted by the user 40, a lower limit of the target range $BG_{TRL}$ and an upper (high) limit of the target range $BG_{TRH}$. These limits are chosen by the user 40 so that they contain the desired blood glucose target as the midpoint. Additionally, the Offset Target K may be calculated dynamically in accordance with the following equation:

$$K = BG_{Target} - \text{Offset}, \quad (4)$$

where $BG_{Target}$ is the midpoint of the blood glucose target range $BG_{TR}$ and Offset is the preconfigured distance between the target center $BG_{Target}$ and the Offset Target, K.

In some implementations, the insulin dose rate IRR may be determined by the following process on a processor 112, 132, 142. Other processes may also be used.

function IIR($sf, $current_bg, $bg_default=60, $insulin_concentration, $ins_units_of_measure='units/hr') {

```
    settype($sf,'float');
    settype($bg_default,'float');
    settype($current_bg,'float');
    settype($insulin_concentration,'float');
    /*
        @param $sf = sensitivity factor from db
        @param $current_bg = the current bg value being
        submitted
        @param $db_default = the default "Stop Insulin When"
value....If it isn't passed, it defaults to 60
        @param $insulin_concentration = the default insulin
concentration from settings
    */
    if($current_bg > 60) {
        $iir = array( );
        $iir[0] = round(($current_bg - $bg_default) * $sf, 1);
        if ($ins_units_of_measure != 'units/hr') {
            $iir[1] = round(($current_bg - $bg_default) * $sf /
$insulin_concentration ,1);
        }
        return $iir;
    } else {
        return 0;
    }
}
```

Referring to decision block 304, when the dose calculation process 300 determines that the inputted blood glucose value BG is the first inputted blood glucose value, then the dose calculation process 300 defines the value of the current multiplier M equal to an initial multiplier ($M_I$) at block 306. The dose calculation process 300 then calculates, at block 320, the Insulin Infusion Rate in accordance with the IIR equation (EQ. 3A) and returns to the process 200 (see FIG. 2).

Figure 5A:
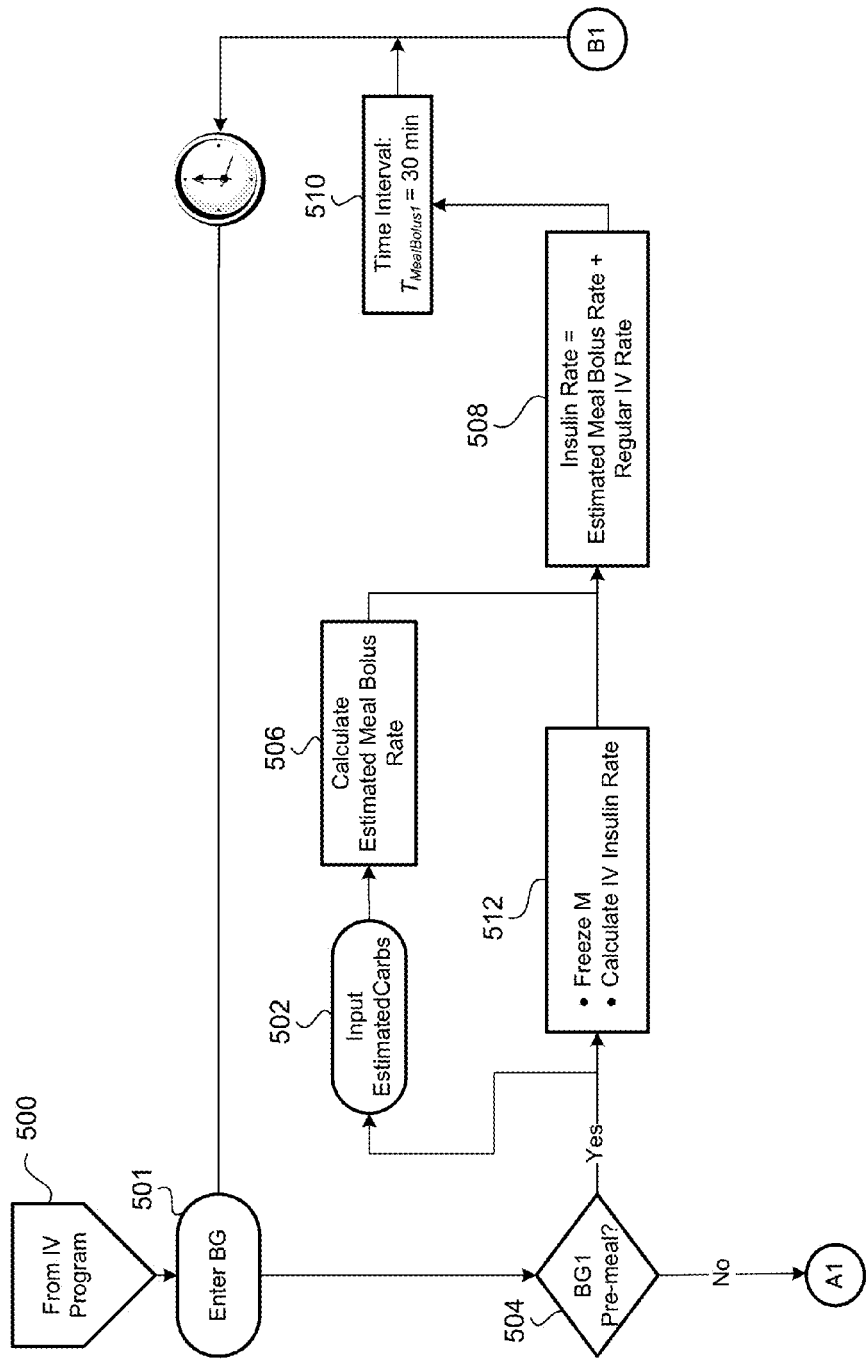
FIGS. 5A and 5B are schematic views of an exemplary meal bolus process of FIG. 2A.
Figure 5B:
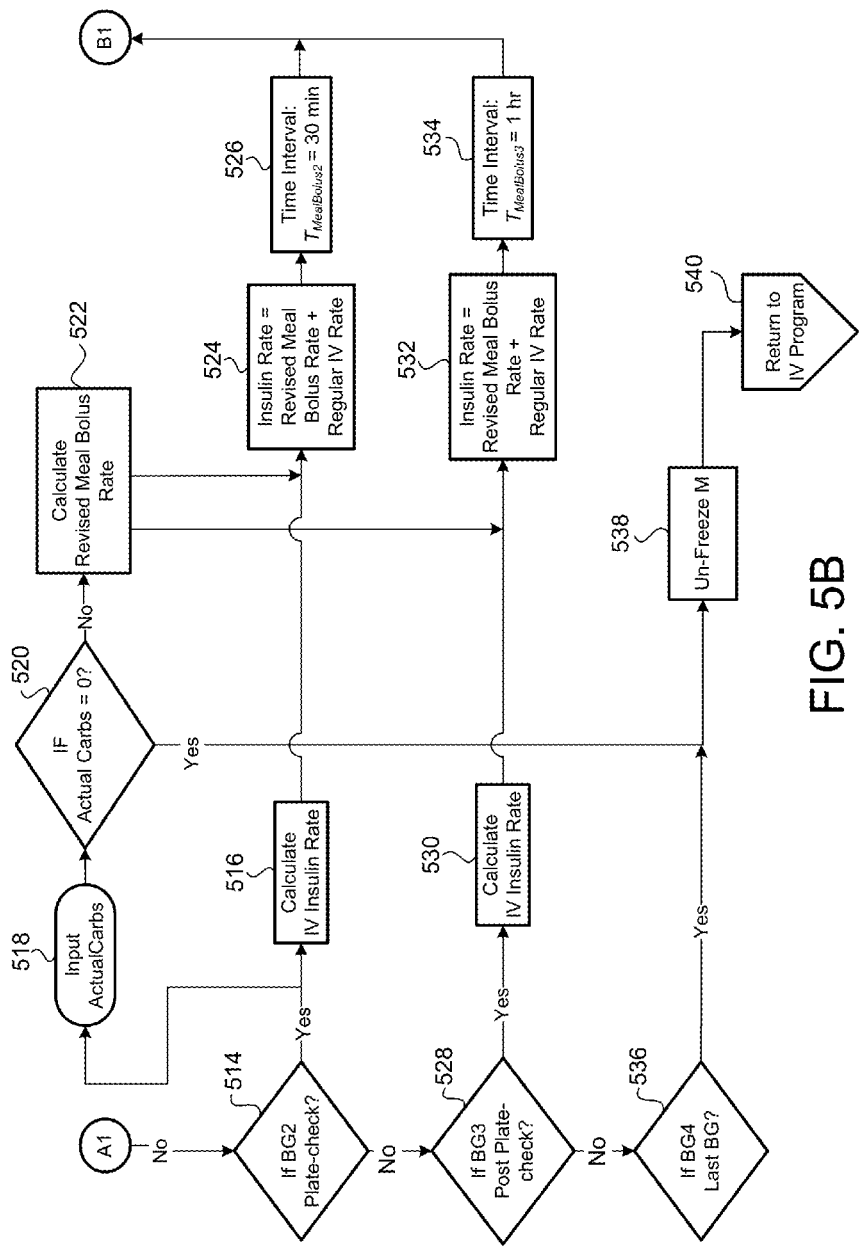

However, referring back to decision block 304, when the dose calculation process 300 determines that the inputted blood glucose value BG is not the first inputted blood glucose value, the dose calculation process 300 determines if the Meal Bolus Module has been activated at decision block 308. If the dose calculation process 300 determines that the Meal Bolus Module has been activated, then the dose calculation process 300 begins a Meal Bolus process 500 (see FIG. 5).

Referring back to decision block 308, if the Meal Bolus Module has not been activated, the dose calculation process 300 determines, at decision block 310, if the current blood glucose value BG is greater than the upper limit $BG_{TRH}$ of the blood glucose target range $BG_{TR}$. If the blood glucose value BG is greater than the upper limit $BG_{TRH}$ of the blood glucose target range $BG_{TR}$, the dose calculation process 300 determines, at block 314, a ratio of the current blood glucose value BG to the previous blood glucose value $BG_P$, where $BG_P$ was measured at an earlier time than the current BG.

The process 200 then determines if the ratio of the blood glucose to the previous blood glucose, $BG/BG_P$, is greater than a threshold value $L_A$, as shown in the following equation:

$$(BG/BG_P) > L_A \quad (5)$$

where BG is the patient's current blood glucose value; $BG_P$ is the patient's previous blood glucose value; and $L_A$ is the threshold ratio of $BG/BG_P$ for blood glucose values above the upper limit of the blood glucose target range $BG_{TRH}$. If the ratio $BG/BG_P$ exceeds the threshold ratio $L_A$, then the Multiplier M is increased. In some examples, the threshold ratio $L_A$ equals 0.85.

If the dose calculation process 300 determines that the ratio ($BG/BG_P$) of the blood glucose value BG to the previous blood glucose value $BG_P$ is not greater than the threshold ratio $L_A$ for a blood glucose value BG above the upper limit $BG_{TRH}$ of the blood glucose target range $BG_{TR}$, then the dose calculation process 300 sets the value of the current multiplier M to equal the value of the previous multiplier $M_P$, see block 312.

$$M = M_P \quad (6)$$

Referring back to block 314, if the dose calculation process 300 determines that the ratio ($BG/BG_P$) of the blood glucose value BG to the previous blood glucose $BG_P$ is greater than the threshold ratio $L_A$ for a blood glucose value above upper limit $BG_{TRH}$ of the blood glucose target range $BG_{TR}$, then dose calculation process 300 multiplies the value of the current multiplier M by a desired Multiplier Change Factor ($M_{CF}$) at block 318. The dose calculation process 300 then calculates the insulin infusion rate at block 320 using the IIR equation (EQ. 3A) and returns to the process 200 (see FIG. 2).

Referring back to block 310, when the dose calculation process 300 determines that the current blood glucose value BG is not greater than the upper limit $BG_{TRH}$ of the blood glucose target range $BG_{TR}$, the dose calculation process 300 then determines if the current blood glucose concentration BG is below the lower limit $BG_{TRL}$, of the blood glucose target range $BG_{TR}$ at decision block 311. If the current blood glucose value BG is below the lower limit $BG_{TRL}$, of the blood glucose target range $BG_{TR}$, the dose calculation process 300 at block 316 divides the value of the current multiplier M by the Multiplier Change Factor ($M_{CF}$), in accordance with the following equation:

$$M = M_P/M_{CF} \quad (7)$$

and calculates the current insulin infusion rate IIR using equation 3 at block 320 and returns to the process 200 (see FIG. 2).

At block 311, if the dose calculation process 300 determines that the blood glucose value BG is not below the lower limit of the blood glucose target range $BG_{TRL}$, the dose calculation process 300 sets the value of the current multiplier to be equal to the value of the previous multiplier $M_P$ at block 312 (see EQ. 6).

Referring again to FIG. 3, at block 311, if the current blood glucose value BG is below the lower limit of the target range $BG_{TRL}$, logic passes to decision block 322, where the process 300 determines if the current blood glucose concentration BG is below a hypoglycemia threshold $BG_{Hypo}$. If the current blood glucose BG is below the hypoglycemia threshold $BG_{Hypo}$, logic then passes to block 324, where the process 300 recommends hypoglycemia treatment, either by a calculation of an individualized dose of intravenous glucose or oral hypoglycemia treatment.

Referring back to FIG. 2A, after the dose calculation process 300 calculates the insulin infusion rate IIR, the process 200 proceeds to a time calculation process 400 (FIG. 4A) for calculating a time interval $T_{Next}$ until the next blood glucose measurement.

Figure 4A:
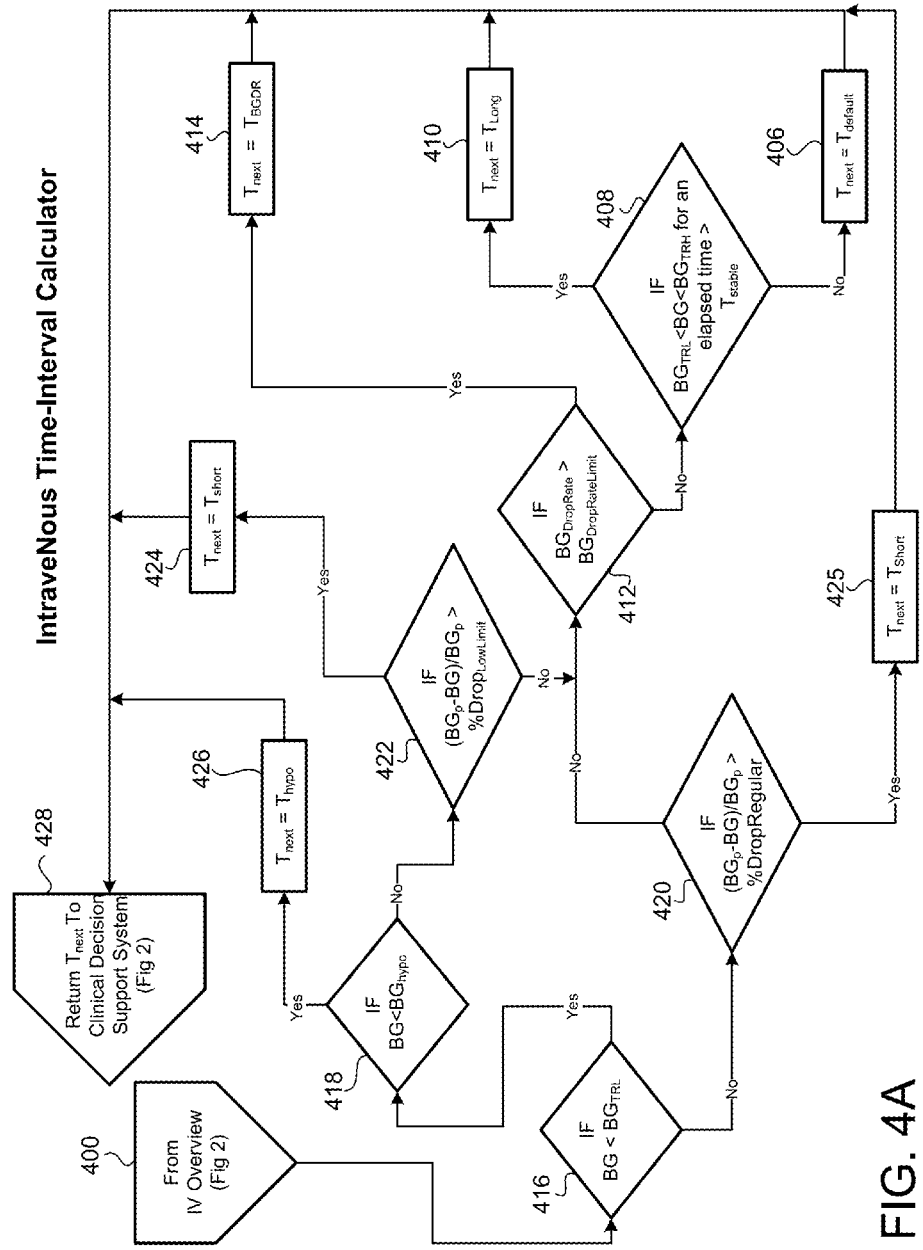
FIG. 4A is a schematic view of an exemplary calculation of the intravenous time interval of FIG. 2A.

FIG. 4A shows the process 400 for calculating a time interval $T_{Next}$ between the current blood glucose measurement BG and the next blood glucose measurement $BG_{next}$. The time-duration of blood glucose measurement intervals $T_{Next}$ may vary and the starting time interval can either be inputted by a user 40 at the beginning of the process 200, 300, 400, or defaulted to a predetermined time interval, $T_{Default}$ (e.g., one hour). The time interval $T_{Next}$ is shortened if the blood glucose concentration BG of the patient 10 is decreasing excessively, or it may be lengthened if the blood glucose concentration BG of the patient 10 becomes stable within the blood glucose target range $BG_{TR}$.

The process 400 determines a value for the time interval $T_{Next}$ based on several conditions. The process 400 checks for the applicability of several conditions, where each condition has a value for $T_{next}$ that is triggered by a logic-test (except $T_{default}$). The process 400 selects the lowest value of $T_{next}$ from the values triggered by logic tests (not counting $T_{default}$). If no logic test was triggered, the process selects $T_{default}$. This is accomplished in FIG. 4A by the logic structure that selects the lowest values of $T_{next}$ first. However, other logic structures are possible as well.

The time calculation process 400 determines at decision block 416 if the current blood glucose BG is below the lower limit $BG_{TRL}$ (target range low limit) of the blood glucose target range $BG_{TR}$. If the current blood glucose BG is below the lower limit $BG_{TRL}$ of the blood glucose target range $BG_{TR}$, then the time calculation process 400 determines, at decision block 418, if the current blood glucose BG is less than a hypoglycemia-threshold blood glucose level $BG_{Hypo}$.

If the current blood glucose BG is less than the hypoglycemia-threshold blood glucose level $BG_{Hypo}$ the time calculation process 400 sets the time interval $T_{Next}$ to a hypoglycemia time interval $T_{Hypo}$, e.g., 15 or 30 minutes, at block 426. Then the time calculation process 400 is complete and returns to the process 200 (FIG. 2) at block 428.

If the current blood glucose BG is not less than (i.e., is greater than) the hypoglycemia-threshold blood glucose level $BG_{Hypo}$ at block 418, the time calculation process 400 determines at block 422 if the most recent glucose percent drop $BG_{\%\ Drop}$, is greater than the threshold glucose percentage drop $\%\ Drop_{Low\ Limit}$ (for a low BG range) using the following equation:

$$BG_{\%\ drop} > \%\ Drop_{Low\ Limit} \quad (8A)$$

since $$BG_{\%\ drop} = \left(\frac{(BG_P - BG)}{BG_P}\right) \quad (8B)$$

then, $$\left(\frac{(BG_P - BG)}{BG_P}\right) > \%\ Drop_{Low\ Limit} \quad (8C)$$

where $BG_P$ is a previously measured blood glucose.

If the current glucose percent drop $BG_{\%\ Drop}$, is not greater than the limit for glucose percent drop (for the low BG range) $\%\ Drop_{Low\ Limit}$, the time calculation process 400 passes the logic to block 412. In some examples, the low limit $\%\ Drop_{Low\ Limit}$ equals 25%.

Referring back to block 422, if the current glucose percent drop $BG_{\%\ Drop}$ is greater than the limit for glucose percent drop (for the low BG range) $\%\ Drop_{Low\ Limit}$, the time calculation process 400 at block 424 sets the time interval to a shortened time interval $T_{Short}$, for example 20 minutes, to accommodate for the increased drop rate of the blood glucose BG. Then the time calculation process 400 is complete and returns to the process 200 (FIG. 2) at block 428.

Referring back to decision block 416, if the time calculation process 400 determines that the current blood glucose BG is not below the lower limit $BG_{TRL}$ for the blood glucose target range $BG_{TR}$, the time calculation process 400 determines at block 420 if the blood glucose BG has decreased by a percent of the previous blood glucose that exceeds a limit $\%\ Drop_{Regular}$ (for the regular range, i.e., blood glucose value $BG > BG_{TRL}$), using the formula:

$$\left(\frac{(BG_P - BG)}{BG_P}\right) > \%\ Drop_{Regular} \quad (9)$$

If the blood glucose BG has decreased by a percentage that exceeds the regular threshold glucose percent drop (for the regular BG range) $\%\ Drop_{Regular}$, the time calculation process 400, at block 425, sets the time interval to the shortened time interval $T_{short}$, for example 20 minutes. A reasonable value for $\%\ Drop_{Regular}$ for many implementations is 66%. Then the time calculation process 400 is complete and returns to the process 200 (FIG. 2) at block 428. If, however, the glucose has not decreased by a percent that exceeds the threshold glucose percent drop $\%\ Drop_{Regular}$, (for the regular BG range), the time calculation process 400 routes the logic to block 412. The process 400 determines, at block 412, a blood glucose rate of descent $BG_{DropRate}$ based on the following equation:

$$BG_{DropRate} = (BG_P - BG)/(T_{Current} - T_{Previous}) \quad (10)$$

where $BG_P$ is the previous blood glucose measurement, $T_{Current}$ is the current time and $T_{Previous}$ is the previous time. Moreover, the process 400 at block 412 determines if the blood glucose rate of descent $BG_{DropRate}$ is greater than a preconfigured drop rate limit $BG_{dropRateLimit}$.

If the time calculation process 400 at block 412 determines that the blood glucose rate of descent $BG_{DropRate}$, has exceeded the preconfigured drop rate limit $BG_{dropRateLimit}$, the time interval $T_{Next}$ until the next blood glucose measurement is shortened at block 414 to a glucose drop rate time interval $T_{BGDR}$, which is a relatively shorter time interval than the current time interval $T_{Current}$, as consideration for the fast drop. The preconfigured drop rate limit $BG_{dropRateLimit}$ may be about 100 mg/dl/hr. The glucose drop rate time interval $T_{BGDR}$ may be 30 minutes, or any other predetermined time. In some examples, a reasonable value for $T_{Default}$ is one hour. Then the time calculation process 400 is complete and returns to the process 200 (FIG. 2) at block 428.

If the time calculation process 400 determines at block 412 that the glucose drop rate $BG_{DropRate}$ does not exceed the preconfigured rate limit $BG_{dropRateLimit}$, the time calculation process 400 determines, at block 408, if the patient's blood glucose concentration BG has been within the desired target range $BG_{TR}$ (e.g., $BG_{TRL} < BG < BG_{TRH}$) for a period of time $T_{Stable}$. The criterion for stability in the blood glucose target range $BG_{TR}$ is a specified time in the target range $BG_{TR}$ or a specified number of consecutive blood glucose measurements in the target range BG$_{TR}$. For example, the stable period of time T$_{Stable}$ may be one hour, two hours, two and a half hours, or up to 4 hours. If the stability criterion is met then the time interval T$_{Next}$ until the next scheduled blood glucose measurement BG may be set at block 410 to a lengthened time interval T$_{long}$ (such as 2 hours) that is generally greater than the default time interval T$_{Default}$. Then the time calculation process 400 is complete and returns to the process 200 (FIG. 2) at block 428. If the time calculation process 400 determines that the patient 10 has not met the criteria for stability, the time calculation process 400 sets the time interval T$_{Next}$ to a default time interval T$_{Default}$ at block 406. Then the time calculation process 400 is complete and returns to the process 200 (FIG. 2) at block 428.

Referring to FIGS. 4B and 4C, once the time calculation process 400 calculates the recommended time interval T$_{Next}$, the process 200 provides a countdown timer 430 that alerts the user 40 when the next blood glucose measurement is due. The countdown timer 430 may be on the display 116 of the patient device 110 or displayed on the display 146 of the hospital system 140. When the timer 430 is complete, a "BG Due!" message might be displayed as shown in FIG. 4B. The countdown timer 430 may include an overdue time 432 indicating the time late if a blood glucose value is not entered as scheduled.

In some implementations, the countdown timer 430 connects to the alarm system 120 of the user device 110. The alarm system 120 may produce an audible sound via the speaker 122 in the form of a beep or some like audio sounding mechanism. The audible and/or visual notification may also be sent via the network to the hospital system 140 (or any other remote station) and displayed on the display 146 of the hospital system 140 or played through speakers 152 of the hospital system 140, or routed to the cell phone or pager of the user. In some examples, the audible alarm using the speakers 122 is turned off by a user selection 434 on the display 116 or it is silenced for a preconfigured time. The display 116, 146 may show information 230 that includes the patient's intravenous treatment information 230*a* or to the patient's subcutaneous treatment information 230*b*. In some examples, the user 40 selects the countdown timer 430 when the timer 430 indicates that the patient 10 is due for his or her blood glucose measurement. When the user 40 selects the timer 430, the display 116, 146 allows the user 40 to enter the current blood glucose value BG as shown in FIG. 4D. For intravenous patients 10, the process 200 may ask the user 40 (via the display 116, 146) if the blood glucose is pre-meal blood glucose measurement (as shown in FIG. 4D). When the user 40 enters the information 230 (FIG. 4D), the user 40 selects a continue button to confirm the entered information 230, which leads to the display 116, 146 displaying blood glucose information 230*c* and a timer 430 showing when the next blood glucose measurement BG is due (FIG. 4E). In addition, the user 40 may enter the patient's blood glucose measurement BG at any time before the timer 430 expires, if the user 40 selects the 'enter BG' button 436. Therefore, the user 40 may input blood glucose values BG at any time, or the user 40 may choose to start the Meal Bolus process 500 (see FIG. 5) by selecting the start meal button 438 (FIG. 4E), transition the patient to SubQ insulin therapy 600 (see FIG. 6), or discontinue treatment 220.

Referring to FIGS. 5A-5D, in some implementations, the process 200 includes a process where the patient's blood glucose level BG is measured prior to the consumption of caloric intake and calculates the recommended intravenous mealtime insulin requirement necessary to control the patient's expected rise in blood glucose levels during the prandial period. When a user 40 chooses to start the Meal Bolus process 500 (e.g., when the user 40 positively answers that this is a pre-meal blood glucose measurement in FIG. 4D, or when the user 40 selects the start meal button 438 in FIG. 4E), the Meal Bolus process 500, at decision block 504, requests the blood glucose BG of the patient 10. The user 40 enters the blood glucose value BG at 501 or the system 100 receives the blood glucose BG from a glucometer 124. This blood glucose measurement is referred to herein as the Pre-Meal BG or BG1. In some examples, where the user 40 enters the information, the user 40 selects a continue button to confirm the entered information 230*c*. In some examples, the meal bolus process 500 is administered to a patient 10 over a total period of time T$_{MealBolus}$. The total period of time T$_{MealBolus}$ is divided into multiple time intervals T$_{MealBolus1}$ to T$_{MealBolusN}$, where N is any integer greater than zero. In some examples, a first time interval T$_{MealBolus1}$ runs from a Pre-Meal blood glucose value BG1 at measured at time T$_1$, to a second blood glucose value BG2 at measured at time T$_2$. A second time interval T$_{MealBolus2}$ runs from the second blood glucose value BG2 measured at time T$_2$ to the third blood glucose value BG3 measured at time T$_3$. A third time interval T$_{MealBolus3}$ runs from the third blood glucose value BG3 measured at time T$_3$ to a fourth blood glucose value BG4 measured at time T$_4$. In some implementations where the time intervals T$_{MealBolusN}$ are smaller than T$_{Default}$, the user 40 should closely monitor and control over changes in the blood glucose of the patient 10. For example, a total period of time T$_{MealBolus}$ equals 2 hours, and may be comprised of: T$_{MealBolus1}$=30 minutes, T$_{MealBolus2}$=30 minutes, and T$_{MealBolus3}$=1 hour. This example ends on the fourth blood glucose measurement. When the Meal Bolus process 500 has been activated, an indication is displayed on the display 116, 146 informing the user 40 that the process 500 is in progress. The Meal Bolus process 500 prompts the user 40 if the entered blood glucose value BG is the first blood glucose value prior to the meal by displaying a question on the patient display 116. If the Meal Bolus process 500 determines that the entered blood glucose value BG is the first blood glucose value (BG1) prior to the meal, then the Meal Bolus process 500 freezes the current multiplier M from being adjusted and calculates a regular intravenous insulin rate IRR at block 512. The regular intravenous insulin rate IRR may be determined using EQ. 3A. Meanwhile, at block 502, the Meal Bolus process 500 loads preconfigured meal parameters, such as meal times, insulin type, default number of carbohydrates per meal, the total period of time of the meal bolus process T$_{MealBolus}$, interval lengths (e.g., T$_{MealBolus1}$, T$_{MealBolus1}$ ... T$_{MealBolusN}$), and the percent, "C", of the estimated meal bolus to be delivered in the first interval T$_{MealBolus1}$. In some examples, when the system 100 includes a hospital electronic medical record system 140, nutritional information and number of grams of carbohydrates are retrieved from the hospital electronic medical record systems 140 automatically. The Meal Bolus process 500 allows the user 40 to select whether to input a number of carbohydrates from a selection of standard meals (AcutalCarbs) or to use a custom input to input an estimated number of carbohydrates (EstimatedCarbs) that the patient 10 is likely to consume. The Meal Bolus process 500 then flows to block 506, where the estimated meal bolus rate for the meal is calculated. The calculation process in block 506 is explained in two steps. The first step is calculation of a meal bolus (in units of insulin) in accordance with the following equation:

$$\text{Estimated Meal Bolus} = \text{EstimatedCarbs} / \text{CIR} \qquad (11\text{A})$$

where CIR is the Carbohydrate-to-Insulin Ratio, previously discussed.

The Meal Bolus process 500 then determines the Estimated Meal Bolus Rate based on the following equation:

$$\text{Estimated Meal Bolus Rate} = \text{Estimated Meal Bolus} * C / T_{MealBolus1} \quad (11B)$$

Where, $T_{MealBolus1}$ is the time duration of the first time interval of the Meal Bolus total period of time $T_{MealBolus}$. C is a constant adjusted to infuse the optimum portion of the Estimated Meal Bolus during first time interval $T_{MealBolus1}$. For instance: if Estimated Meal Bolus=6 units, $T_{MealBolus1}$=0.5 hours, and C=25%, then applying Eq. 11A as an example:

$$\text{Estimated Meal Bolus Rate} = (6 \text{ units}) * 25\% / (0.5 \text{ hours}) = 3 \text{ units/hour} \quad (11C)$$

The Meal Bolus process 500 calculates the Total Insulin Rate at block 508 as follows:

$$\text{Total Insulin Infusion Rate} = \text{Estimated Meal Bolus Rate} + \text{Regular Intravenous Rate} \quad (12)$$

The Meal Bolus process 500 flows to block 510 where it sets the time interval for the first interval $T_{MealBolus1}$ to its configured value, (e.g., usually 30 minutes), which will end at the second meal bolus blood glucose (BG2).

After the first time interval $T_{MealBolus1}$ expires (e.g., after 30 minutes elapse), the Meal Bolus process 500 prompts the user 40 to enter the blood glucose value BG once again at block 501. When the Meal Bolus process 500 determines that the entered blood glucose value BG is not the first blood glucose value BG1 entered at block 504 (i.e., the pre-meal BG, BG1, as previously discussed), the process 500 flows to block 514. At block 514, the Meal Bolus process 500 determines if the blood glucose value BG is the second value BG2 entered by the user 40. If the user 40 confirms that the entered blood glucose value BG is the second blood glucose value BG2 entered, the Meal Bolus process 500 uses the just-entered blood glucose BG2 to calculate the intravenous insulin rate IRR at block 516 and flows to block 524. Simultaneously, if the blood glucose is the second blood glucose BG2, the Meal Bolus process 500 prompts the user 40 to enter the actual amount of carbohydrates that the patient 10 received at block 518. The Meal Bolus process 500 then determines at decision block 520 and based on the inputted amount of actual carbohydrates, if the patient did not eat, i.e., if the amount of carbohydrates is zero. If the Meal Bolus process 500 determines that the patient did not eat, the Meal Bolus process 500 then flows to block 540, where the meal bolus process 500 is discontinued, the multiplier is no longer frozen, and the time interval $T_{Next}$ is restored to the appropriate time interval $T_{Next}$, as determined by process 400. If however, the Meal Bolus process 500 determines that the patient 10 ate, i.e., the actual carbohydrates is not zero, then The Meal Bolus process 500 flows to block 522, where it calculates a Revised meal bolus rate according to the following equations, where the Revised Meal Bolus and then an amount of insulin (in units of insulin) are calculated:

$$\text{Revised Meal Bolus} = \text{ActualCarbs}/\text{CIR} \quad (13A)$$

The process at block 522 then determines the amount (in units of insulin) of estimated meal bolus that has been delivered to the patient 10 so far:

$$\text{Estimated Meal Bolus Delivered} = \text{Estimated Meal Bolus Rate} * (T_2 - T_1) \quad (13B)$$

where time T1 is the time of when the first blood glucose value BG1 is measured and time T2 is the time when the second blood glucose value BG2 is measured.

The process at block 522 then calculates the portion of the Revised Meal Bolus remaining to be delivered (i.e., the Meal Bolus that has not yet been delivered to the patient 10) as follows:

$$\text{Revised Meal Bolus Remaining} = \text{Revised Meal Bolus} - \text{Estimated Meal Bolus Delivered} \quad (13C)$$

The process at block 522 then calculates the Revised Meal Bolus Rate as follows:

$$\text{Revised Meal Bolus Rate} = \text{Revised Meal Bolus Remaining}/\text{Time Remaining} \quad (14A)$$

where Time Remaining=$T_{MealBolus} - T_{MealBolus1}$. Since the total time interval $T_{MealBolus}$ and the first time interval $T_{MealBolus1}$ are preconfigured values, the Time Remaining may be determined.

The Meal Bolus process 500 calculates the total insulin rate at block 524 by adding the Revised Meal Bolus Rate to the regular Intravenous Rate (IIR), based on the blood glucose value BG:

$$\text{Total Insulin Rate} = \text{Revised Meal Bolus Rate} + \text{IIR} \quad (14B)$$

The Meal Bolus process 500 flows to block 526 where it sets the time interval $T_{Next}$ to the second interval $T_{MealBolus2}$, which will end at the third meal bolus blood glucose BG3 e.g., usually 30 minutes.

After the second interval, $T_{MealBolus2}$ expires (e.g., 30 minutes), the Meal Bolus process 500 prompts the user 40 to enter the blood glucose value BG once again at block 501. The Meal Bolus process 500 determines that the entered blood glucose value BG is not the first blood glucose value entered at block 504 (previously discussed) and flows to block 514. The Meal Bolus process 500 determines that the entered blood glucose value BG is not the second blood glucose value entered at block 514 (previously discussed) and flows to block 528. At block 528, the Meal Bolus process 500 determines if the blood glucose value BG is the third value entered. If the entered blood glucose value BG is the third blood glucose value BG entered, the Meal Bolus process 500 calculates the intravenous insulin rate IRR at block 530 and flows to block 532.

At block 532 the process determines the Total Insulin Rate by adding the newly-determined Regular Intravenous Insulin Rate (IIR) to the Revised Meal Bolus Rate, which was determined at BG2 and remains effective throughout the whole meal bolus time, $T_{mealbolus}$.

The Meal Bolus process 500 flows to block 534 where it sets the time interval $T_{Next}$ to the third interval $T_{MealBolus3}$ for the fourth meal bolus blood glucose, e.g., usually 60 minutes. In some implementations, more than 3 intervals ($T_{MealBolus1}$, $T_{MealBolus2}$, $T_{MealBolus3}$) may be used. Additional intervals $T_{MealBolusN}$ may also be used and the process handles the additional intervals $T_{MealBolusN}$ similarly to how it handles the third time interval $T_{MealBolus3}$. As discussed in the current example, the third interval $T_{MealBolus3}$ is the last time interval, which ends with the measurement of the fourth blood glucose measurement BG4.

After the third time interval, $T_{MealBolus3}$, expires (e.g., 60 minutes), the Meal Bolus process 500 prompts the user 40 to enter the blood glucose value BG once again at block 501. The Meal Bolus process 500 determines that the entered blood glucose value BG is not the first blood glucose value entered at block 504 (previously discussed) and flows to block 514. The Meal Bolus process 500 determines that the entered blood glucose value BG is not the second blood glucose value entered at block 514 (previously discussed), nor the third blood glucose level entered at block 528 and flows to block 536. At block 536, the Meal Bolus process 500 determines that the inputted blood glucose is the fourth blood glucose value BG4. In this example, the fourth blood glucose value BG4 is the last one. The process 500 then flows to block 538 where the multiplier is no longer frozen, and the time interval $T_{Next}$ is restored to the appropriate time interval $T_{Next}$, as determined by the process 400 (FIG. 4A). At this time, the Meal Bolus process 500 ends and the user 40 is prompted with a message indicating that the Meal Bolus process 500 is no longer active.

As shown in FIG. 4E, the process 200 provides a countdown timer 430 that alerts the user 40 when the next blood glucose measurement is due. The countdown timer 430 may be on the display 116 of the patient device 110 or displayed on the display 146 of the hospital system 140. When the timer 430 is complete, a "BG Due!" message might be displayed as shown in FIG. 4B. Moreover, the timer 430 may be a countdown timer or a meal timer indicating a sequence of mealtime intervals (e.g., breakfast, lunch, dinner, bedtime, mid-sleep).

In some implementations, a Meal Bolus process 500 may be implemented by the following process on a processor 112, 132, 142. Other processes may also be used.

```
    function PreMealIIR($PatientID, $CurrentBG, $Multiplier,
$InsulinConcentration,
        $EstCarbs, $ActualCarbs, $TimeInterval,
$InsulinUnitsOfMeasure, $MealBolusCount) {
        $iir = array( );
        $CarbInsulinRatio = CIR($PatientID);
        $NormalInsulin = ($CurrentBG - 60) * $Multiplier;
        if($MealBolusCount == 0)
        {
            //first run - Premeal Bolus
            $MealBolus = ($EstCarbs /$CarbInsulinRatio);
            if($MealBolus <0)
            {$MealBolus = 0;}
            $iir[0] = $NormalInsulin + ( $MealBolus *.5 );
            $iir[2] = ( $MealBolus *.5 );
            /*
            print "Premeal: MX: " . $Multiplier . "<BR>";
            print ($CurrentBG - 60) * $Multiplier;
            print " + " ;
            print ( $MealBolus *.5 );
            */
        } else if($MealBolusCount == 1){
            //second run Post Meal Bolus
            //third run time interval coming in is actually the
            //difference between the premeal BG and the first Post
Meal BG (second run)
            $MealBolus = ($ActualCarbs / $CarbInsulinRatio);
            $OldMealBolus = ($EstCarbs / $CarbInsulinRatio);
            $CurrentMealBolus = ($MealBolus -
($OldMealBolus *.5 * $TimeInterval))/1.5;
            if($CurrentMealBolus <0)
            {$CurrentMealBolus =0;}
            $iir[0] = $NormalInsulin + $CurrentMealBolus ;
            $iir[2] = $CurrentMealBolus;
            /*
            print "PlateCheck: <BR>MX: " . $Multiplier . "<BR>";
            print "Est Carbs: " . $EstCarbs . "<BR>";
            print "ActualCarbs: " . $ActualCarbs . "<BR>";;
            print "CarbInsulinRatio: " . $CarbInsulinRatio . "<BR>";
            print "TimeInterval: " . $TimeInterval . "<BR>";
            print "Multiplier: " . $Multiplier;
            */
        }
        else
        {
            $MealBolus = ($ActualCarbs / $CarbInsulinRatio);
            $OldMealBolus = ($EstCarbs / $CarbInsulinRatio);
            /*
            print "Actual Carbs: " . $ActualCarbs . "<BR>";
            print "Est Carbs: " . $EstCarbs . "<BR>";
            print "CIR: " . $CarbInsulinRatio . "<BR>";
            print "Multiplier: " . $Multiplier . "<BR>";
```

```
            print "CurrentBG: " . $CurrentBG . "<BR>";
            print "IIR: " . (($CurrentBG - 60) * $Multiplier) . "<BR>";
            print "MealBolus: " . $MealBolus . "<BR>";
            print "OldMealBolus: " . $OldMealBolus . "<BR>";
            print "TimeInterval: " . $TimeInterval . "<BR>";
            */
            $CurrentMealBolus = ($MealBolus -
($OldMealBolus *.5 * $TimeInterval))/1.5;
            if($CurrentMealBolus <0)
            {$CurrentMealBolus =0;}
            $iir[0] = $NormalInsulin + $CurrentMealBolus;
            $iir[2] = $CurrentMealBolus;
            /*
            print "Post PlateCheck: <BR>MX: " . $Multiplier .
"<BR>";
            print "IIR: ";
            print ($CurrentBG - 60) * $Multiplier . "<BR>";
            print "Est Carbs: " . $EstCarbs . "<BR>";
            print "Acutal Carbs: " . $ActualCarbs . "<BR>";
            print "Old Meal bolus: " . $OldMealBolus . "<BR>";
            print "TimeInterval: " . $TimeInterval . "<BR>";
            print "Meal bolus: " . $MealBolus . "<BR>";
            print "Final Calc: " . $iir[0];
            */
        }
        if ($InsulinUnitsOfMeasure != "units/hr")
        {
            $iir[0] = $iir[0]/$InsulinConcentration;
        }
        return $iir;
    }
```

Figure 6A:
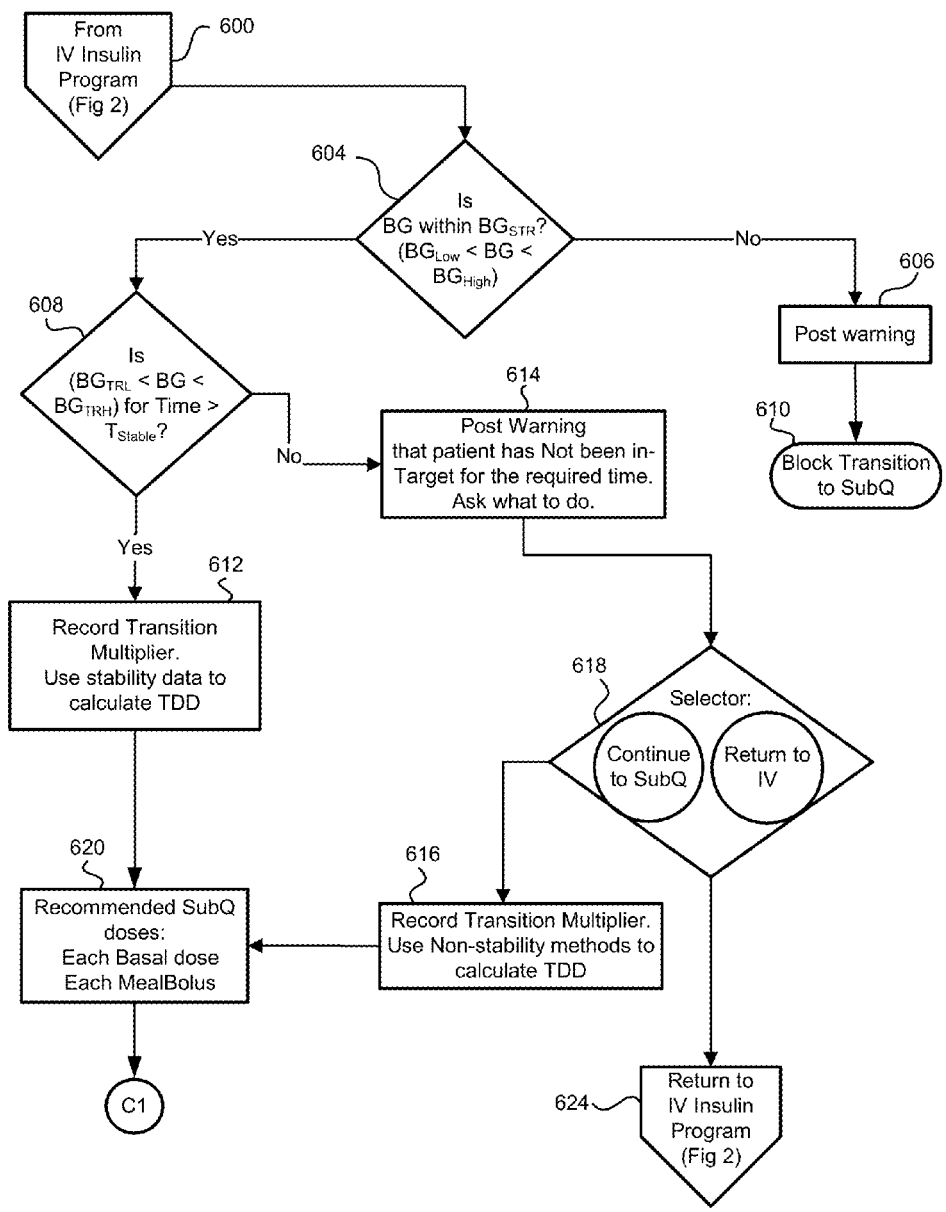
FIGS. 6A and 6B are schematic views of an exemplary subcutaneous transition process of FIG. 2A.
Figure 6B:
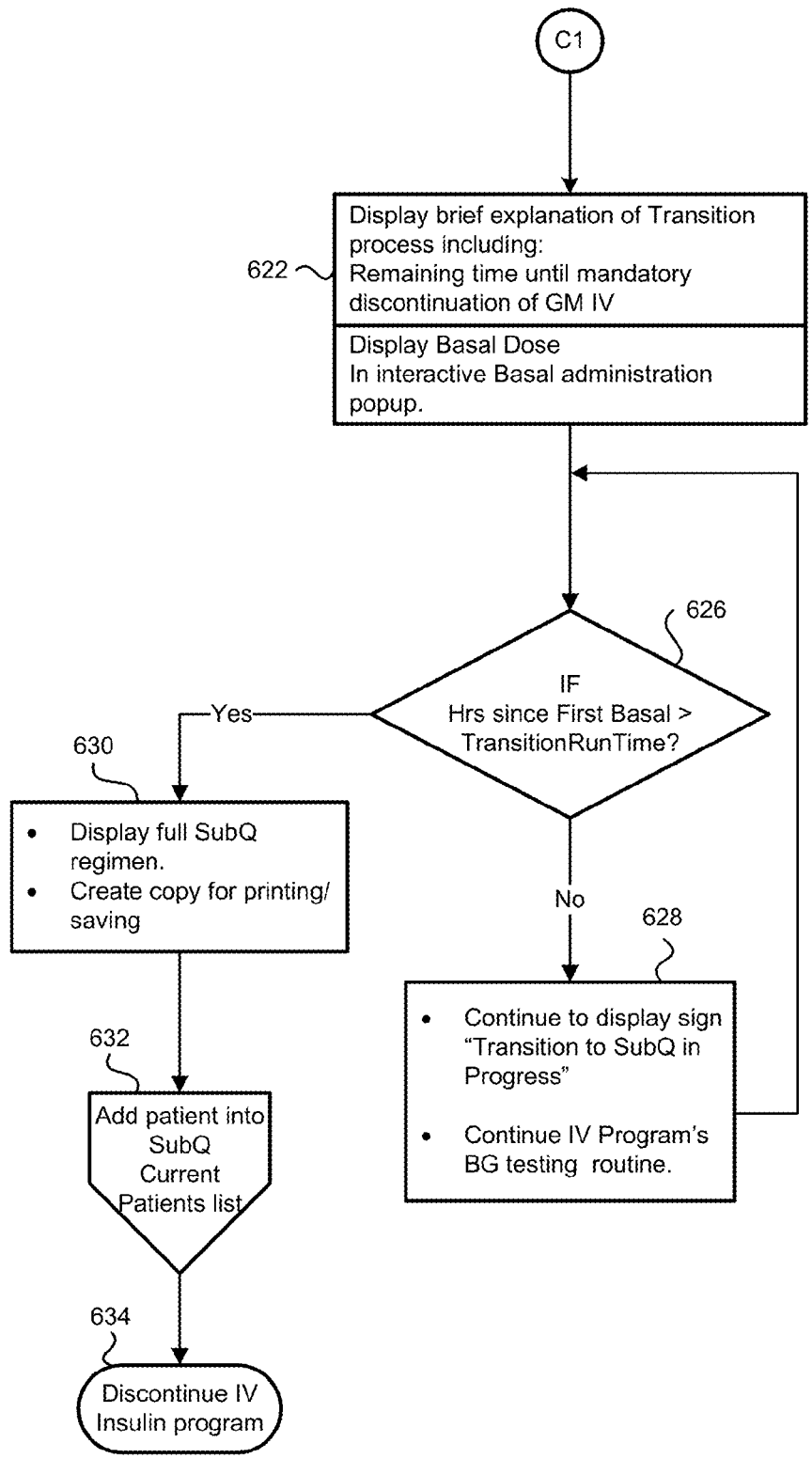

Referring to FIGS. 2A and 6A-6B, if the user elects to initiate the SubQ Transition process 600, the SubQ Transition process 600 determines at decision block 604 if the current blood glucose BG is within a preconfigured stability target range $BG_{STR}$, e.g., 70-180 mg/dl, which is usually wider than the prescribed Target Range, $BG_{TR}$. If the blood glucose BG is not within the preconfigured stability target range $BG_{STR}$ (e.g., $BG_{Low}<BG<BG_{High}$), the SubQ Transition process 600 at block 606 displays a warning notification on the patient display 116. Then, at lock 610, the SubQ Transition process 600 is automatically discontinued.

Referring back to block 604, if the blood glucose BG is within the preconfigured stability target range $BG_{STR}$ (e.g. 70-180 mg/dl), the SubQ Transition process 600 at decision block 608 determines if the patient's blood glucose measurement BG has been in the patient's personalized prescribed target range $BG_{TR}$ for the recommended stability period $T_{stable}$, e.g., 4 hours. If the SubQ Transition process 600 determines that the blood glucose value BG has not been in the prescribed target range $BG_{STR}$ for the recommended stability period $T_{Stable}$, the SubQ Transition process 600 moves to block 614 where the system 100 presents the user 40 with a warning notification on the patient display 116, explaining that the patient 10 has not been in the prescribed target range for the recommended stability period (see FIG. 6C). The SubQ Transition process 600 continues to decision block 618 where it determines whether the user 40 wants the patient 10 to continue the SubQ Transition process or to discontinue the SubQ Transition process. The SubQ Transition process 600 displays on the display 116 of the patient device 110 the question to the user 40 as shown in FIG. 6C. If the user 40 chooses to discontinue the SubQ Transition process, the SubQ Transition process 600 flows to block 624, where the SubQ Transition process is discontinued.

Referring back to block 618, if the user 40 chooses to override the warning and continue the SubQ Transition process, the process 600 prompts the user 40 to enter SubQ information 617 as shown in FIG. 6E. The SubQ Transition process 600 flows to block 616, where the patient's SubQ Transition dose is calculated as a patient's total daily dose TDD. In some implementations, TDD is calculated in accordance with equation:

$$TDD = QuickTransitionConstant * M_{Trans} \quad (15A)$$

where QuickTransitionConstant is usually 1000, and $M_{Trans}$ is the patient's multiplier at the time of initiation of the SubQ transition process.

Referring again to block 616, in some implementations TDD is calculated by a statistical correlation of TDD as a function of body weight. The following equation is the correlation used:

$$TDD = 0.5 * Weight \ (kg) \quad (15B)$$

The SubQ Transition process 600 continues to block 620, where the recommended SubQ dose is presented to the user 40 (on the display 116) in the form of a Basal recommendation and a Meal Bolus recommendation (see FIG. 6F).

Referring again to decision block 608, if the SubQ Transition process 600 determines that the patient 10 has been in the prescribed target range $BG_{TR}$ for the recommended stability period, $T_{stable}$, SubQ Transition process 600 continues to block 612, where the patient's total daily dose TDD is calculated in accordance with the following equation:

$$TDD = (BG_{Target} - K)*(M_{Trans})*24 \quad (16)$$

where $M_{Trans}$ is the patient's multiplier at the time of initiation of the SubQ transition process.

In some implementations, the patient's total daily dose TDD may be determined by the following process on a processor 112, 132, 142. Other processes may also be used.

```
function getIV_TDD($PatientID)
{
    //$weight = getOneField("weight", "patients", "patientID",
    $PatientID);
    //return $weight/2;
    $CI = get_instance( );
    $CI->load->model('options');
    $d = $CI->options->GetIVTDDData($PatientID);
    $TargetHigh = $d["TargetHigh"];
    $TargetLow = $d["TargetLow"];
    $Multiplier = $d["Multiplier"];
    $MidPoint = ($TargetHigh + $TargetLow) / 2;
    $Formula = ($MidPoint - 60) * $Multiplier * 24;
    return $Formula;
}
```

When the patient's total daily dose TDD is calculated, the SubQ Transition process 600 continues to block 620 where the recommended SubQ dose is presented to the user 40 as described above. The SubQ Transition process 600 continues to block 622, where the SubQ Transition process 600 provides information to the user 40 including a recommended dose of Basal insulin. The user 40 confirms that the Basal insulin has been given to the patient 10; this starts a transitions timer using the $TransitionRunTime_{Next}$, usually 4 hours. At this point, normal calculation rules governing the IIR are still in effect, including the intravenous IIR timer (process 400), which continues to prompt for blood glucose tests at time intervals $T_{Next}$ as described previously. The SubQ Transition process 600 passes to decision block 626, which determines whether the recommended time interval TransitionRunTime has elapsed, e.g., 4 hours, after which time the SubQ Transition process 600 continues to block 630, providing the user with subcutaneous insulin discharge orders and exiting the IV Insulin process in block 634.

Referring back to FIG. 2A, in some implementations, the subcutaneous program (at block 226) includes six sub programs: a subcutaneous standard program (FIGS. 9A-9B); a subcutaneous for tube-fed patients Program (FIG. 10); a subcutaneous program with no meal boluses (FIG. 11); a meal-by-meal subcutaneous program without carbohydrate counting (FIG. 12); a meal-by-meal subcutaneous program with carbohydrate counting (FIGS. 13A-13B); and a subcutaneous program for non-diabetic patients (FIG. 14). Some functions or processes are used within the six subcutaneous programs such as determining the general and pre-meal correction (FIG. 7), determining the adjustment factor AF (FIG. 8), and hypoglycemia treatment.

Figure 7:
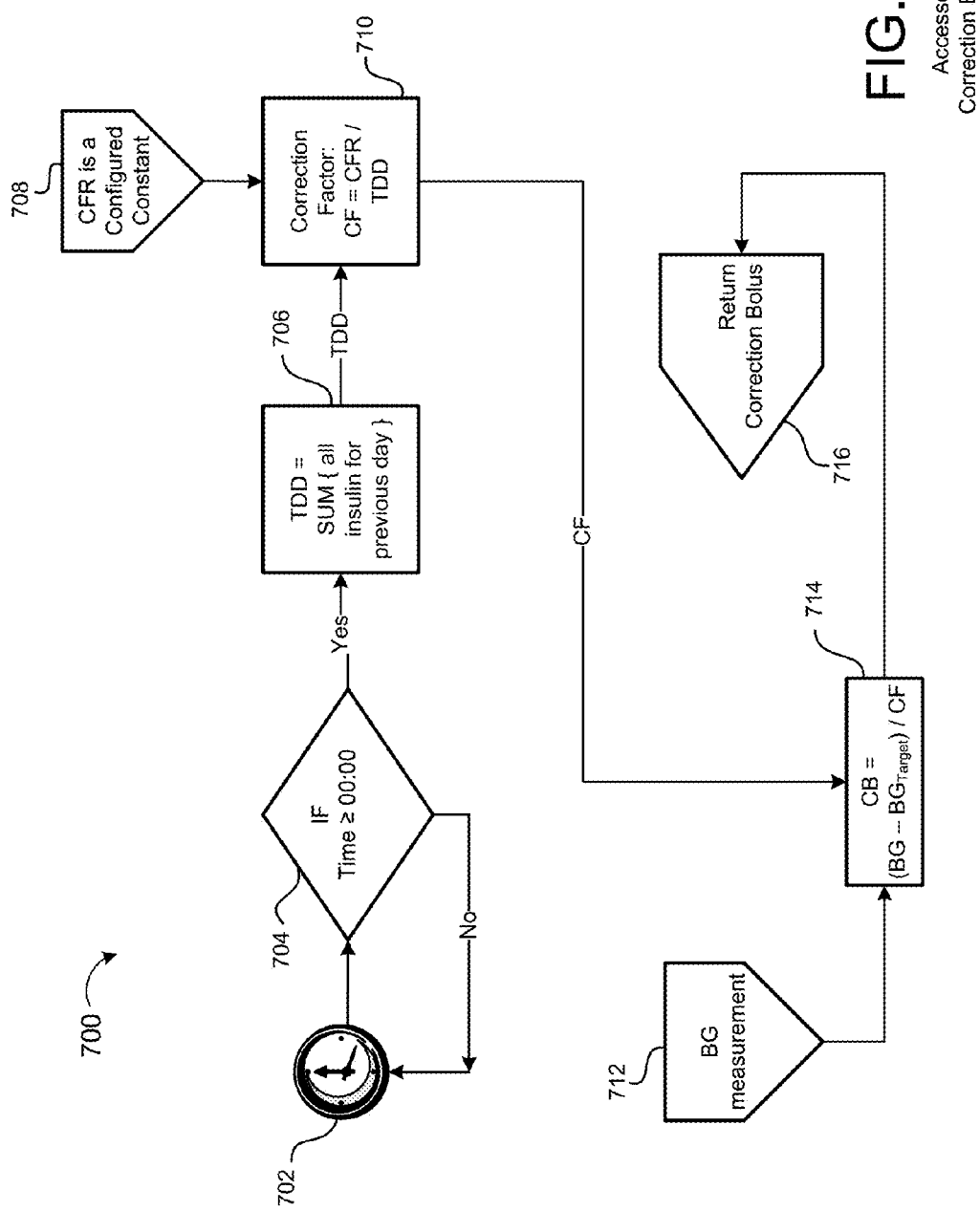
FIG. 7 is a schematic view of an exemplary correction boluses process.

Referring to FIG. 7, correction boluses CB are used in the six subprograms of SubQ program (block 226, FIG. 2); because of this, correction boluses CB may be incorporated into a function having variables such as the blood glucose measurement BG of a patient 10, a patient's personalized target blood glucose $BG_{Target}$, and a correction factor CF. Thus, correction boluses CB are described as a function of the blood glucose measurement BG, the target blood glucose $BG_{Target}$, and the correction factor CF (see EQ. 19 below). The process 700 calculates the correction bolus CB immediately after a blood glucose value BG of a patient 10 is measured. Once a calculation of the correction bolus CB is completed, a nurse 40 administers the correction bolus CB to the patient 10, right after the blood glucose value BG is measured and used to calculate the correction bolus CB.

In some examples, the process 700 may determine the total daily dose TDD of insulin once per day, for example, every night at midnight. Other times may also be available. In addition, the total daily dose TDD may be calculated more frequently during the day, in some examples, the total daily dose TDD is calculated more frequently and considers the total daily dose TDD within the past 24 hours. The process 700 provides a timer 702, such as a countdown timer 702, where the timer 702 determines the time the process 700 executes. The timer 702 may be a count up timer or any other kind of timer. When the timer 702 reaches its expiration or reaches a certain time (e.g., zero for a countdown timer 702), the timer 702 executes the process 700. The counter 702 is used to determine at what time the process 704 calculates the total daily dose TDD. If the counter is set to 24 hours for example, then decision block 704 checks if the time has reached 24 hours, and when it does, then the process 700 calculates the total daily dose TDD of insulin. The correction bolus process 700 determines a total daily dose of insulin TDD, based on the following equation:

$$TDD = \text{Sum over previous day (all basal+all meal boluses+all correction boluses)} \quad (17)$$

After the process 700 determines the total daily dose TDD of insulin at block 706, the process 700 determines a Correction Factor CF immediately thereafter at block 710, using the calculated total daily dose TDD from block 706 and Eq. 17. The correction factor CF is determined using the following equation:

$$CF = CFR/TDD \quad (18)$$

where CFR is a configurable constant stored in the non-transitory memory 24, 114, 144 of the system. At block 708, the process 700 retrieves the configurable constant CFR value from the non-transitory memory 24, 114, 144 to calculate the correction factor CF at block 710. The configurable constant CFR is determined from a published statistical correlation and is configurable by the hospital, nurses and doctors. The flexibility of modifying the correction constant CF, gives the system 100 flexibility when a new published configurable constant CFR is more accurate than the one being used. In some examples, the configurable constant CFR is a configurable constant set to 1700, other values may also be available. In some examples, the total daily dose TDD and CF are determined once per day (e.g., at or soon after midnight).

Once the correction factor CF is determined in EQ. 18, the process 700 determines the correction bolus insulin dose at block 714 using the following equation:

$$CB = (BG - BG_{Target})/CF \qquad (19)$$

where BG is the blood glucose measurement of a patient 10 retrieved at block 712, $BG_{Target}$ is the patient's personalized Target blood glucose, and CF is the correction factor. The process 700 returns the correction bolus CB at block 716. Rapid-acting analog insulin is currently used for Correction Boluses because it responds quickly to a high blood glucose BG. Also rapid acting analog insulin is currently used for meal boluses; it is usually taken just before or with a meal (injected or delivered via a pump). Rapid-acting analog insulin acts very quickly to minimize the rise of patient's blood sugar which follows eating.

A Correction Bolus CB is calculated for a blood glucose value BG at any time during the process 200. Pre-meal Correction Boluses CB, are calculated using EQ. 19. In the Pre-meal Correction Bolus equation (19) there is no need to account for Remaining Insulin $I_{Rem}$ because sufficient time has passed for almost all of the previous meal bolus to be depleted. However, post-prandial correction boluses (after-meal correction boluses) are employed much sooner after the recent meal bolus and use different calculations, that account for remaining insulin $I_{Rem}$ that remains in the patient's body after a recent meal bolus. Rapid-acting analog insulin is generally removed by a body's natural mechanisms at a rate proportional to the insulin remaining $I_{Rem}$ in the patient's body, causing the remaining insulin $I_{Rem}$ in the patient's body to exhibit a negative exponential time-curve. Manufacturers provide data as to the lifetime of their insulin formulations. The data usually includes a half-life or mean lifetime of the rapid-acting analog insulin. The half-life of the rapid-acting analog insulin may be converted to mean lifetime iLifeRapid for rapid-acting insulin by the conversion formula:

$$iLifeRapid = Half\text{-}life * \ln(2) \qquad (20)$$

where ln(2) is the natural logarithm {base e} of two.

The present invention uses the mean lifetime iLifeRapid in its formulas (EQ. 20). Since the manufacturers and brands of insulin are few, the system 100 maintains the Half-life or iLifeRapid value of each insulin manufacturer up-to-date.

The insulin remaining in the patient's body Remaining Insulin $I_{Rem}$ is determined by multiplying the most recent insulin bolus {Meal Bolus, Correction Bolus, or combined bolus} times a time-dependent exponentially-declining factor as follows:

$$I_{Rem} = (\text{Previous Bolus}) * e^{-\left(\frac{T_{Current} - T_{Previous}}{iLifeRapid}\right)} = \qquad (21)$$
$$(\text{Previous Bolus}) * \text{EXP}\left(-\left(\frac{T_{Current} - T_{Previous}}{iLifeRapid}\right)\right)$$

where $T_{current}$ is the current time, and $T_{PrevBolus}$ is the time at which the last bolus was given to the patient 10. The Post Meal Correction bolus $CB_{post}$ is calculated similar to an ordinary correction bolus CB (EQ. 19) with a deduction of the remaining insulin $I_{Rem}$ in the patient's body:

$$CB_{post} = \left(\frac{BG - BG_{Target}}{CF}\right) - (\text{Previous Bolus}) e^{-\left(\frac{T_{Current} - T_{Previous}}{iLifeRapid}\right)} \qquad (22)$$

In some examples, Post Meal Correction doses $CB_{Post}$ (EQ. 22) are taken into consideration only if they are positive (units of insulin), which means a negative value post meal correction bolus $CB_{Post}$ cannot be used to reduce the meal bolus portion of a new combined bolus.

Figure 8:
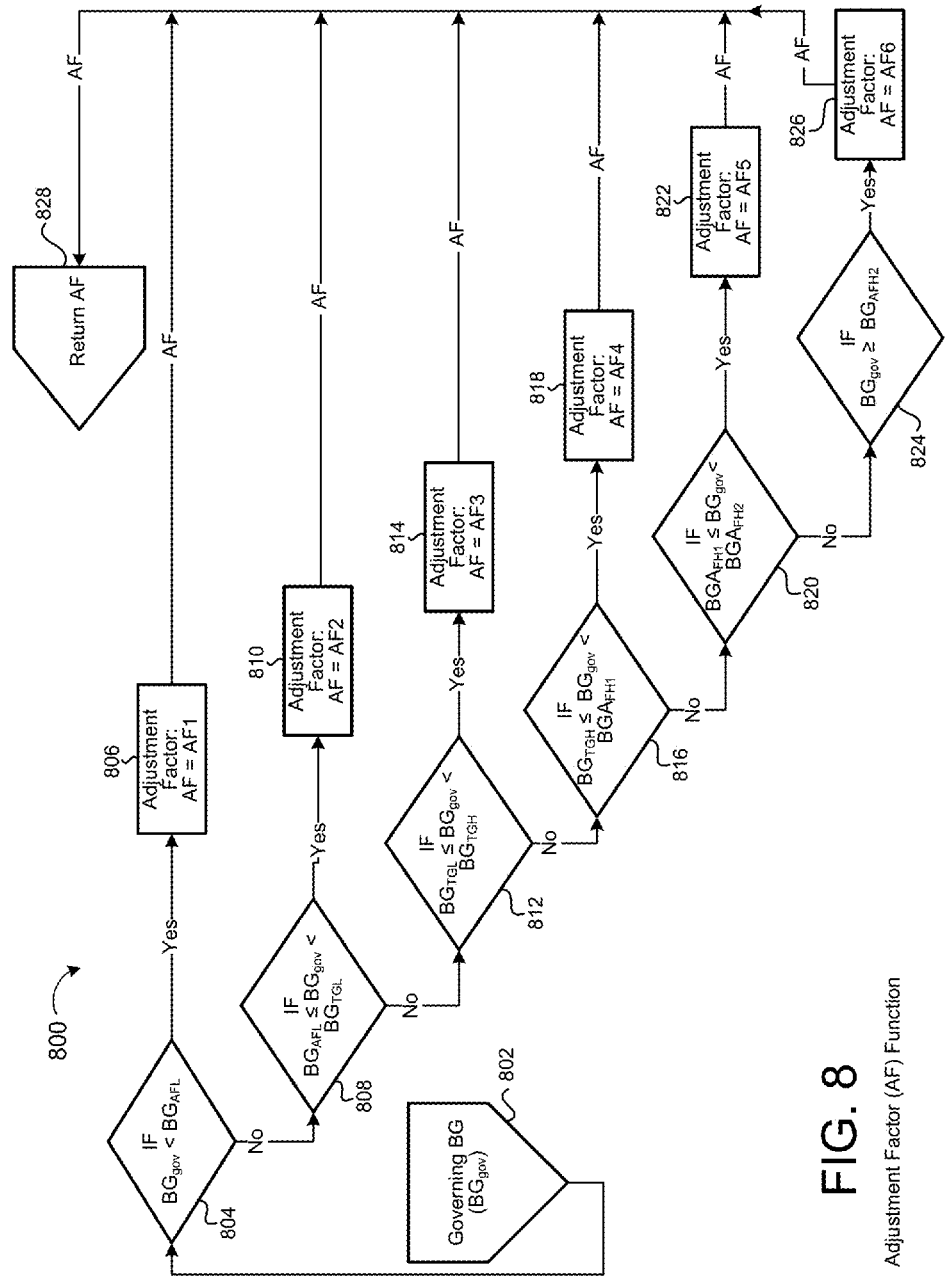
FIG. 8 is a schematic view of an exemplary adjustment factor process.

Referring to FIG. 8, the process 800 describes a function that determines an Adjustment Factor AF based on an input of a Governing Blood GlucoseBGgov. The Adjustment Factor AF is used by the six subcutaneous subprograms: a subcutaneous standard program (FIGS. 9A-9B); a subcutaneous for tube-fed patients Program (FIG. 10); a subcutaneous program without meal boluses (FIG. 11); a meal-by-meal subcutaneous program without carbohydrate counting (FIG. 12); a meal-by-meal subcutaneous program with carbohydrate counting (FIGS. 13A-13B); and a subcutaneous program for non-diabetic patients (FIG. 14). These six subprograms adjust the insulin dose administered to a patient 10. An adjustment factor process 800, applied to Basal doses and Meal Boluses, determines an adjusted Recommended Basal dose RecBasal, or a Recommended Meal Bolus RecMealBol, by applying a unit-less Adjustment Factor AF to the preceding recommendation of the same dose, $RecBasal_{prev}$, or $RecMealBol_{prev}$. All dose adjustments are governed by a Governing Blood Glucose value $BG_{gov}$. The Governing Blood Glucose values $BG_{gov}$ in the process are selected based on the criteria of preceding the previous occurrence of the dose to be adjusted by a sufficient amount of time for the effect (or lack of effect) of the insulin to be observable and measurable in the value of the $BG_{gov}$.

At block 802, the adjustment factor process 800 receives the Governing Glucose value $BG_{gov}$ from non-transitory memory 24, 114, 144, since the adjustment factor AF is determined using the Governing Glucose value $BG_{gov}$. To determine the adjustment factor AF, the adjustment factor process 800 considers the blood glucose target range $BG_{TR}$ (within which Basal doses and Meal Boluses, are not changed), which is defined by a lower limit, i.e., a low target $BG_{TRL}$ and an upper limit, i.e., a high target $BG_{TRH}$. As previously discussed, the target range $BG_{TR}$ is determined by a doctor 40 and entered manually (e.g., using the patient device 110 or the medical record system 140, via, for example, a drop down menu list displayed on the display 116, 146). Each target range $BG_{TR}$ is associated with a set of configurable constants including a first constant $BG_{AFL}$, a second constant $BG_{AFH1}$, and a third constant $BG_{AFH2}$ shown in the below table.

TABLE 1

Target Range Settings

| Input Ranges | $BG_{AFL}$ | $BG_{TRL}$ | $BG_{TRH}$ | $BG_{AFH1}$ | $BG_{AFH2}$ |
|---|---|---|---|---|---|
| 70-100 | 70 | 70 | 100 | 140 | 180 |
| 80-120 | 80 | 80 | 120 | 160 | 200 |
| 100-140 | 70 | 100 | 140 | 180 | 220 |
| 120-160 | 90 | 120 | 160 | 200 | 240 |
| 140-180 | 110 | 140 | 180 | 220 | 260 |

The adjustment factor process 800 determines, at block 804, if the Governing Glucose value $BG_{gov}$ is less than or equal to the first constant $BG_{AFL}$ ($BG_{gov} \leq BG_{AFL}$), if so then at block 806, the adjustment factor process 800 assigns the adjustment factor AF to a first pre-configured adjustment factor AF1 shown in Table 2.

If, at block 804, the Governing Glucose value $BG_{gov}$ is not less than the first constant $BG_{AFL}$, (i.e., $BG_{gov} \geq BG_{AFL}$), then at block 808, the adjustment factor process 800 determines if the Governing Glucose value $BG_{gov}$ is greater than or equal to the first constant $BG_{AFL}$ and less than the low target $BG_{TRL}$ of the target range $BG_{TR}$ ($BG_{AFL} \leq BG_{gov} < BG_{TRL}$). If so, then the adjustment factor process 800 assigns the adjustment factor AF to a second pre-configured adjustment factor AF2, at block 810. If not, then at block 812, the adjustment factor process 800 determines if the Governing Glucose value $BG_{gov}$ is greater than or equal to the low target $BG_{TRL}$ of the target range $BG_{TR}$ and less than the high target level $BG_{TRH}$ of the target range $BG_{TR}$ ($BG_{TRL} \leq BG_{gov} < BG_{TRH}$). If so, then the adjustment factor process 800 assigns the adjustment factor AF to a third pre-configured adjustment factor AF3, at block 814. If not, then at block 816, the adjustment factor process 800 determines if the Governing Glucose value $BG_{gov}$ is greater than or equal to the high target level $BG_{TRH}$ of the target range $BG_{TR}$ and less than the second constant $BG_{AFH1}$ ($BG_{TRH} \leq BG_{gov} < BG_{AFH1}$). If so, then the adjustment factor process 800 assigns the adjustment factor AF to a fourth pre-configured adjustment factor AF4, at block 818. If not, then at block 820, the adjustment factor process 800 determines if the Governing Glucose value $BG_{gov}$ is greater than or equal to the second constant $BG_{AFH1}$ and less than the third constant $BG_{AFH2}$ ($BG_{AFH1} \leq BG_{gov} < BG_{AFH2}$). If so, then the adjustment factor process 800 assigns the adjustment factor AF to a fifth pre-configured adjustment factor AF5, at block 822. If not, then at block 824, the adjustment factor process 800 determines that the Governing Glucose value $BG_{gov}$ is greater than or equal to the third constant $BG_{AFH2}$ ($BG_{gov} \geq BG_{AFH2}$); and the adjustment factor process 800 assigns the adjustment factor AF to a sixth pre-configured adjustment factor AF6, at block 826. After assigning a value to AF the adjustment factor process 800 returns the adjustment factor AF to the process requesting the adjustment factor AF at block 828 (e.g., the subcutaneous process (FIGS. 9A-9B)).

TABLE 2

| Configurable values for Adjustment Factor AF | |
|---|---|
| AF1 = | 0.8 |
| AF2 = | 0.9 |
| AF3 = | 1 |
| AF4 = | 1.1 |
| AF5 = | 1.2 |
| AF6 = | 1.3 |

Figure 9A:
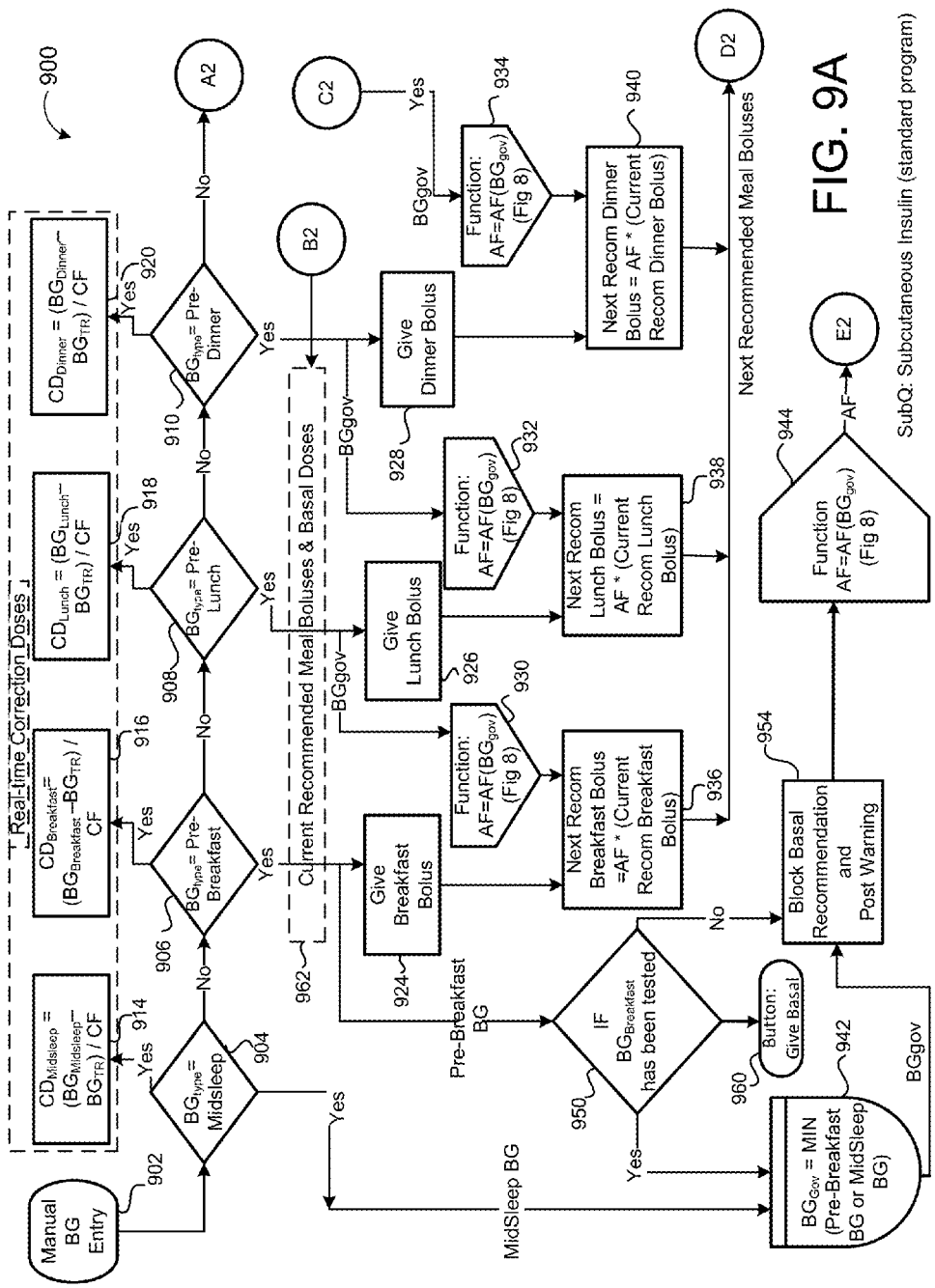
FIGS. 9A and 9B are a schematic view of an exemplary subcutaneous standard program.
Figure 9B:
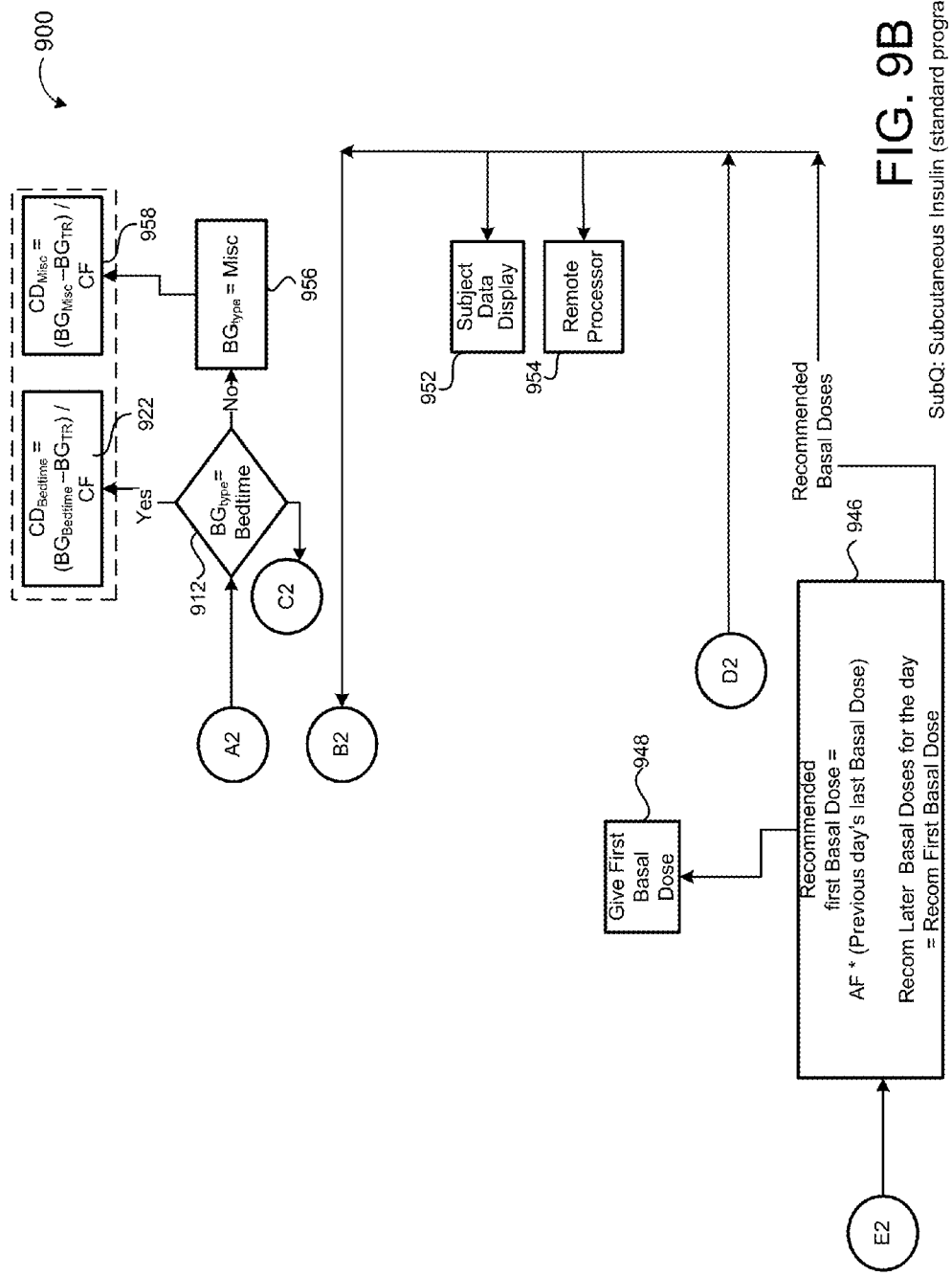

In some examples, a patient 10 may suffer from hypoglycemia during the execution of the process 200. Hypoglycemia treatment may be needed in the Intravenous process 300 (FIGS. 3A and 3B) and 400 (FIG. 4A) or in the SubQ standard process 900 (FIGS. 9A and 9B). The process 200 includes a sub-process that monitors the current blood glucose value BG of a patient 10 and determines if it is less than a hypoglycemia threshold $BG_{Hypo}$ (configurable by the hospital or doctor). If the current blood glucose value BG is less than the hypoglycemia threshold $BG_{Hypo}$, a warning message is displayed on the display 116, 146 warning the patient 10, the nurse and the doctor 40 of the patient's condition, the value of the low current blood glucose value BG, a reminder to turn off the insulin (if the hypoglycemia event occurs in the IV Process (FIG. 2)), and a selector that allows the nurse or doctor 40 to select the type of glucose administered to the patient 10. Some of the selections include: Intravenous D50 (50% glucose by weight) if the patient 10 has an intravenous connection; and Oral glucose (tablets or gel). Once the nurse or doctor 40 enters, using the patient device 110 or the medical record system 140, a type of glucose to be administered to the patient, the process 200 calculates a dose recommendation (or prescribed dose) and displays the calculated dose on the display 116, 146. Moreover, the process 200 prompts the nurse or doctor 40 to input via the patient device 110 or the hospital device 140, the dose $D_{hypo}$ administered to the patient 10 to treat the hypoglycemia by grams of glucose may be determined based on the following equation:

$$D_{hypo}(\text{in grams}) = F_{HypoTreatment} * (BG_{Target} - BG) \quad (23)$$

where $BG_{TR}$ is the blood glucose target range and $F_{HypoTreatment}$ is a hypoglycemia treatment factor that is a configurable constant. In some examples, the hypoglycemia treatment factor $F_{HypoTreatment}$ equals 0.2 (glucose gm/(mg/dl)).

If the nurse or doctor 40 selected a solution (e.g., D50 as opposed to oral glucose), the process 200 uses a different formula to calculate the recommended dose, where the calculated grams of glucose are divided by the concentration of glucose $C_{HypoFluidConc}$ in the fluid in (grams of glucose/ml) to obtain the recommended dose in units of solution volume (e.g., ml). The formula is:

$$D_{hypo}(\text{in ml}) = (BG_{TR} - BG) * F_{HypoTreatment} / C_{HypoFluidConc} \quad (24)$$

For D50, the hypoglycemic fluid concentration is 0.5 grams of glucose/ml.

Referring to FIGS. 2A and 9A-9B, if the user 40 initiates a subcutaneous insulin process 900 at block 210 or block 600, also referred to as a Standard SubQ Program, the subcutaneous insulin process 900 requests the user 40 to enter SubQ information 617 for the patient 10, such as patient diabetes status, subcutaneous type ordered for the patient 10 (e.g., Basal/bolus and correction that is intended for patients on a consistent carbohydrate diet, or Basal and correction that is intended for patients who are NPO or on continuous eternal feeds), total daily dosage (TDD) (e.g., calculated using any of EQs. 15A-15C), bolus insulin type (e.g., Novolog), basil insulin type (e.g., Lantus) and frequency of distribution (e.g., 1 dose per day, 2 doses per day, 3 doses per day, etc.), basil time, basal percentage of TDD, meal bolus percentage of TDD, daily meal bolus distribution (e.g., breakfast bolus, lunch bolus and dinner bolus), or any other relevant information. In some implementations, the patient SubQ information 617 is prepopulated with default parameters, which may be adjusted or modified. In some examples, portions of the patient SubQ information 617 is prepopulated with previously entered patient subcutaneous information 216a. The subcutaneous insulin process 900 may prompt the request to the user 40 to enter the SubQ information 617 on the display 116 of the patient device 110. In some implementations, the subcutaneous insulin process 900 prompts the request to the user 40 to enter the SubQ information 617 on the display 116 of the patient device 110 for new SubQ patients after transitioning from being treated with an intravenous treatment as shown in FIG. 9C. For instance, the user 40 may select whether or not to continue treating the patient with the subcutaneous insulin process 900. In other implementations, the subcutaneous insulin process 900 prompts the request on the display 116 for a custom start of new SubQ patients being treated with the subcutaneous insulin process 900 shown in FIG. 9D. In some examples, the subcutaneous insulin process 900 prompts the request on the display 116 for a weight-based start of SubQ patients being treated with the subcutaneous insulin process 900 as shown in FIG. 9E. For instance, the user 40 may input the weight (e.g., 108 kg) of the patient 10, and in some examples, the TDD may be calculated using EQ. 15B based on the patient's weight.

Basal insulin is for the fasting insulin-needs of a patient's body. Therefore, the best indicator of the effectiveness of the basal dose is the value of the blood glucose BG after the patient 10 has fasted for a period of time. Meal Boluses are for the short-term needs of a patient's body following a carbohydrate-containing meal. Therefore, the best indicator of the effectiveness of the Meal Bolus is a blood glucose measurement BG tested about one mean insulin-lifetime iLifeRapid after the Meal Bolus, where the lifetime is for the currently-used insulin type. For rapid-acting analog insulin the lifetime is conveniently similar to the time between meals. The SubQ process 900 begins with the manual entry of a blood glucose value BG at block 902. Then the SubQ process 900 determines the type of the blood glucose value BG, i.e., the time that the blood glucose BG is measured, e.g., midsleep, pre-breakfast, pre-lunch, pre-dinner, or bedtime. In some examples, the subcutaneous insulin process 900 includes a default setup of three meals per day, but a bedtime snack or other additional meals may be configurable.

At block 904, the subcutaneous insulin process 900 determines if the blood glucose type $BG_{type}$ is Midsleep (measured during a patient's midsleep). If so, then the subcutaneous insulin process 900 calculates a midsleep correction dose $CB_{Midsleep}$ of insulin at block 914, using the following equation (based on EQ. 2):

$$CB_{Midsleep} = (BG_{Midsleep} - BG_{Target})/CF; \quad (25)$$

or by the Correction Bolus Function, process 700, (FIG. 7), and sends the blood glucose value BG at midsleep $BG_{Midsleep}$ (received at block 902) to block 942.

If the entered blood glucose BG is not measured during midsleep, i.e., $BG_{type}$ is not equal MidSleep, then the subcutaneous insulin process 900 determines if the blood glucose type $BG_{type}$ is measured before breakfast ($BG_{type}$=pre-Breakfast) at block 906. If so, then the subcutaneous insulin process 900 calculates a breakfast correction dose $CB_{Breakfast}$ of insulin at block 916, using the following equation (based on EQ. 2):

$$CB_{Breakfast} = (BG_{Breakfast} - BG_{Target})/CF; \quad (26)$$

and the patient 10 is administered the breakfast correction dose $CB_{Breakfast}$ as soon as possible. Block 906 sends the pre-breakfast blood glucose value to block 924 and block 950. At block 924, the nurse 40 administers the patient 10 with the breakfast bolus $RecBreakBol_{(current)}$, and then passes the pre-breakfast blood glucose $BG_{Breakfast}$ to block 936 (where the next Recommendation for the Breakfast bolus is calculated after the pre-lunch BGtype is entered). Once the pre-lunch blood glucose is entered at block 902, and the adjustment factor parameter AF governed by the pre-lunch blood glucose is determined (FIG. 8), the adjustment factor AF is also sent to block 936. At block 936, the process 900 determines the next recommended Breakfast Bolus $RecBreakBol_{(Next)}$ based on the following equation:

$$RecBreakBol_{(Next)} = (RecBreakBol_{(current)} * AF \quad (27)$$

At block 950, the subcutaneous insulin process 900 determines if the pre-breakfast blood glucose $BG_{Breakfast}$ has been tested, if not then the subcutaneous insulin process 900 blocks basal recommendation, and blocks the Give Basal dose input sequence at button 960, and posts a warning, displayed on the display 116, 146, to the patient 10, nurse and doctor 40 at block 954 and is stored in the non-transitory memory 24, 114, 144 at block 954. However, if the pre-breakfast blood glucose $BG_{Breakfast}$ has been tested, then the subcutaneous insulin process 900 selects, at block 942, the Governing blood glucose $BG_{gov}$ as the lesser of the two blood glucose values, i.e., the midsleep blood glucose $BG_{MidSleep}$ or the pre-breakfast blood glucose $BG_{Breakfast}$, as shown in the following equation:

$$BG_{gov}(\text{for Basal adjustment}) = MIN(BG_{MidSleep} \text{ or } BG_{Breakfast}) \quad (28)$$

In some implementations, the governing blood glucose $BG_{gov}$ for Basal is the lesser of the MidSleep blood glucose $BG_{MidSleep}$ or the pre-breakfast blood glucose $BG_{Breakfast}$ unless the system 100 determines that the MidSleep blood glucose $BG_{MidSleep}$ caused a Correction bolus dose CB greater than a maximum value (MSCorrMAX), and the following equation applies:

$$(\text{Time of } BG_{Breakfast} - \text{Time of } BG_{MidSleep} \text{ Correction dose}) < DTmin \quad (29)$$

where $DT_{min}$ is a preset time window. In other words

```
{
IF {(TbreakfastBG - TMSCorr) > DTmin} AND
   {MidSleep Correction > MSCorrMAX} THEN
      {BGgov for Basal} = MAX{ pre-breakfastBG, MidSleepBG}
   ELSE {BGgov for Basal} = MIN{pre-breakfastBG, MidSleepBG}
}
```

After determining the governing blood glucose $BG_{gov}$, the subcutaneous insulin process 900 determines the adjustment factor AF at block 944 (see. FIG. 8). The adjustment factor process 800, returns the adjustment factor AF as a function of the governing blood glucose $BG_{gov}$. The subcutaneous insulin process 900 sends the adjustment factor AF to block 946, where the subcutaneous insulin process 900 determines the adjustment to the patient's insulin dose by the following equation:

$$RecomBasal = (\text{previous } RecomBasal_{PM}) * AF, \quad (30)$$

and the nurse 40 give the patient 10 the Recommended basal dose RecomsBasal at block 948.

In some implementations, where the patient 10 receives multiple Basal doses per day, the subcutaneous insulin process 900 provides the patient 10 with equal doses each time. Therefore, the recommended basal doses RecomBasal for a full day are equal to the first recommended basal dose of Eq. 30. This makes it possible to administer the morning Basal dose RecomBasal immediately after the pre-Breakfast BG has been tested.

For meal Bolus adjustments, the adjustment is applied to the meal bolus of the same meal of the previous day (known as the Governing Meal Bolus $MB_{gov}$). An equivalent statement is that the next day's meal bolus is the adjustment applied to the current meal bolus. The adjustment is based on the Governing Blood Glucose $BG_{gov}$, which is the next scheduled blood glucose BG, following the Governing Meal Bolus $MB_{gov}$. The adjustment value is determined by the Adjustment Factor process 800 (FIG. 8), whose input is the Governing Blood Glucose $BG_{gov}$ and whose output is the adjustment factor AF. The adjustment factor AF is multiplied by the Governing Meal Bolus $MB_{gov}$ to obtain the adjusted Recommended Meal Bolus RecMealBol.

If either the governing blood glucose $BG_{gov}$ or the governing meal bolus $MB_{gov}$ is missing, then the previous day's Recommended Meal Bolus $RecMealBol_{prev}$ is kept in place.

The SubQ process 900 is designed with three meals during the day, Breakfast, Lunch, Dinner. Considering the lunch as the meal, after the blood glucose BG is manually entered at block 902, the SubQ process 900, at block 908, determines that the blood glucose type, $BG_{type}$ is pre-lunch, i.e., $BG_{Lunch}$. the SubQ process 900, at block 918 determines the correction dose based on the following equation (based on EQ. 2):

$$CB_{Lunch}=(BG_{Lunch}-BG_{Target})/CF, \quad (31)$$

Once the SubQ process 900 determines the correction dose, the dose is displayed on the display 114, 146 so that the nurse 40 can administer the dose to the patient 10 as soon as possible.

The current Recommended Lunch Bolus is available at block 962; it has been available since the previous day's pre-Dinner BG. This current Recommended Lunch Bolus is displayed on the display, and the nurse gives the Lunch Bolus $RecLunchBol_{Current}$ at block 926. The SubQ process 900 does not determine a new recommended dose until the pre-Dinner blood glucose is tested at block 910. Then the pre-dinner blood glucose BG serves as the $BG_{gov}$ for the Lunch Bolus and the SubQ process sends the $BG_{gov}$ to block 932, which is the input/output box of the adjustment factor process 800. The adjustment factor process 800 returns the adjustment factor parameter AF, which is in turn sent to block 938. At block 938, the process determines the Next Recommended Lunch Bolus, $RecLunchBol_{Next}$ based on the following equation:

$$RecLunchBol_{Next}=RecLunchBol_{Current}*AF \quad (32)$$

The other meals, Breakfast and Dinner follow the same pattern as the example of Lunch set forth above.

Considering dinner as the meal, after the blood glucose BG is manually entered at block 902, the SubQ process 900, at block 910, determines that the blood glucose type, $BG_{type}$ is pre-dinner. The SubQ process 900, at block 920 determines the correction dose based on the following equation (based on EQ. 2):

$$CB_{Dinner}=(BG_{Dinner}-BG_{Target})/CF, \quad (33)$$

Once the SubQ process 900 determines the correction dose, the dose is displayed on the display 116, 146 so that the nurse 40 can administer the dose to the patient 10 as soon as possible.

The current Recommended Dinner Bolus $RecDinnerBolus_{Current}$ is available at block 962; it has been available since the previous day's Bedtime blood glucose$_{Bedtime}$. This current Recommended Dinner Bolus is displayed on the display, and the nurse gives the patient 10 the recommended Dinner Bolus $RecDinnerBolus_{current}$ at block 928. The SubQ process 900 does not determine a new recommended dose RecomBolus until the bedtime blood glucose is tested at block 912. Then the bedtime blood glucose BG serves as the BGgov for the dinner Bolus and the SubQ process sends the BGgov to block 934, which is the input/output box of the adjustment factor process 800. The adjustment factor process 800 returns the adjustment factor parameter AF, which is in turn sent to block 940. At block 940, the process 900 determines the Next recommended Dinner Bolus $RecDinnerBolus_{Next}$ based on the following equation:

$$RecDinnerBolus_{Next}=RecDinnerBolus_{current}*AF \quad (34)$$

When the SubQ process 900 determines that the blood glucose BG type $BG_{type}$ is bedtime $BG_{Bedtime}$ (i.e., the blood glucose BG is taken at bedtime) at block 912, the SubQ process 900 determines at block 922 the correction dose (based on EQ. 2):

$$CB_{Bedtime}=(BG_{Bedtime}-BG_{Target})/CF, \quad (35)$$

As previously mentioned, the SubQ process 900 is configurable to add additional blood glucose BG measurements having blood glucose type $BG_{type}$ of miscellaneous, as shown in block 956. The SubQ process 900 determines a correction dose at block 958.

$$RecMiscBolus_{Next}=(RecMiscBolus_{Current})*AF \quad (36)$$

Figure 10:
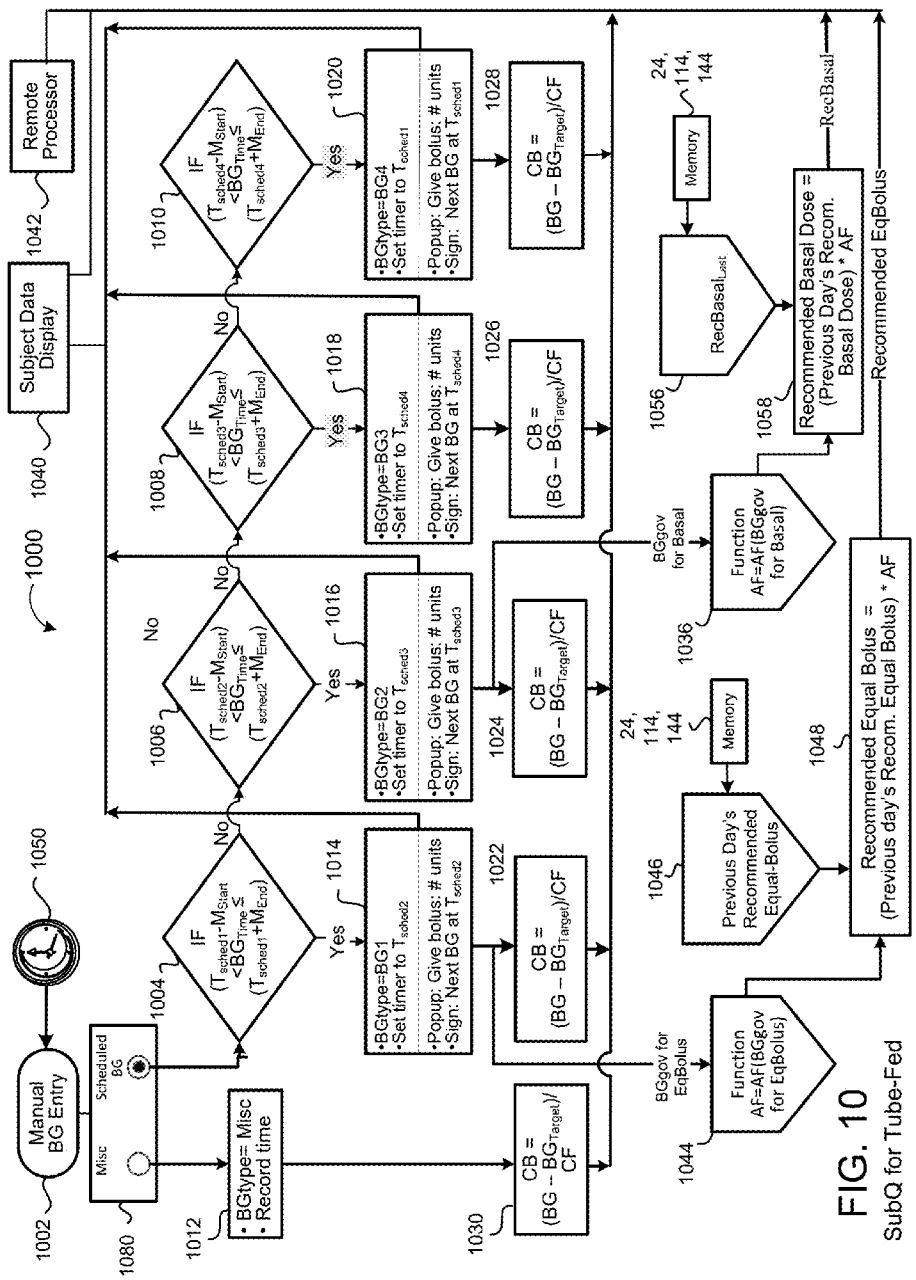
FIG. 10 is a schematic view of an exemplary subcutaneous for tube-fed patients process.

FIG. 10 shows the SubQ for Tube-Fed Patients process 1000 for critically ill patients who are ordered nil per os (NPO), which means that oral food and fluids are withheld from the patient 10. This process 1000 is designed specifically for patients 10 who are receiving a nutrition formula via a tube to the stomach or intravenous TPN (total parenteral nutrition). TPN is when the patient 10 is only receiving nutritional benefits intravenously. Neither TPN nor Tube-Fed patients require meal boluses because they are not eating meals. Instead, they are given equal boluses of Rapid-Acting insulin at equally-spaced scheduled times around the clock to meet the continuous insulin needs of their continuous tube-feeding or TPN nutrition; these boluses are called Equal-Boluses (EqBolus).

SubQ for Tube-Fed Patients process 1000 allows the nurse or doctor 40 to divide the day into equal intervals, via the display 110, 114. In addition, the nurse or doctor 40 can choose the number of scheduled blood glucose measurements BG per day, which equals the number of intervals per day. Each interval includes a scheduled blood glucose measurement BG and an Equal-Bolus EqBolus. The scheduled blood glucose times are: Tsched1; Tsched2; Tsched3 . . . etc., with associated blood glucoses BG1; BG2; BG3 . . . etc. The SubQ for Tube-Fed Patients process 1000 displays the time and BG number of the next-scheduled blood glucose, via the display 110, 114 at block 1040. Optionally, the SubQ for Tube-Fed Patients process 1000 may employ a countdown timer 1050 to obtain the blood glucose measurements BG at the proper times.

To prevent the BG schedule from "migrating around the clock-face", the following method is used: The SubQ for Tube-Fed Patients process 1000 determines if the time at which the blood glucose BG was measured $BG_{Time}$ falls within one of the intervals listed above. If so, then the countdown timer 1050 is set to time-out on the next scheduled blood glucose time Tsched1, Tsched2, Tsched3, . . . etc. Each interval is configured with a start time margin ($M_{Start}$) and an end time margin ($M_{End}$). The SubQ for Tube-Fed Patients process 1000 may be summarized as follows:

IF $[(T_{sched1}-M_{Start})<BG_{Time}<=(T_{sched1}+M_{End})]$; THEN Set countdown timer to time-out at $T_{sched2}$;

IF $[(T_{sched2}-M_{Start})<BG_{Time}<=(T_{sched2}+M_{End})]$; THEN Set countdown timer to time-out at $T_{sched3}$ . . . and so on.

In some examples, where there are four intervals configured, then the last interval's logic is as follows:

IF $[(T_{sched4}-M_{Start})<BG_{Time}<=(T_{sched4}\ M_{End})]$; THEN Set countdown timer to time-out at $T_{sched1}$.

In some implementations, the SubQ for Tube-Fed Patients process 1000 provides two blood glucose schedule plans: Six blood glucose BG tests per day; or four blood glucose BG tests per day. The nurse or doctor 40 can select which one to use for a specific patient 10. The first blood glucose plan for six blood glucose measurements per day includes the following details: each scheduled blood glucose measurement is four hours apart from the next, e.g., 00:00, 04:00, 08:00, 12:00, 16:00, and 20:00, with a start margin $M_{start}$ of 2 hours and an end margin $M_{end}$ of 2 hours. If a blood glucose measurement BG falls within the interval(i) from $\{T_{sched}(i)-2 \text{ hrs}\}$ to $\{T_{sched}(i)+2 \text{ hrs}\}$ the Countdown Timer is set to expire on the next scheduled time, $T_{sched}$ (i+1).

The second blood glucose plan for four blood glucose measurements per day is shown in FIG. 10. FIG. 10 further shows a miscellaneous blood glucose measurement that is not scheduled. The blood glucose measurements are each scheduled six hours apart from the next at 00:00, 06:00, 12:00, and 18:00, with a start margin $M_{Start}$ of 4 hours and an end margin $M_{end}$ of 2 hours. If a the blood glucose measurement falls within the interval (i) from $\{T_{sched}(i)-4 \text{ hrs}\}$ to $\{T_{shed}(i)+2 \text{ hrs}\}$ the Countdown Timer is set to expire on the next scheduled BG $T_{sched}(i+1)$. All four of the blood glucose BG tests.

TABLE 3

Blood Glucose Measurement every 6 hours

| | |
|---|---|
| Start Margin ($M_{Start}$) | 4 hours |
| End Margin ($M_{End}$) | 2 hours |
| $T_{sched}1$ | 00:00 |
| $T_{sched}2$ | 06:00 |
| $T_{sched}3$ | 12:00 |
| $T_{sched}4$ | 18:00 |

The SubQ for Tube-Fed Patients process 1000 starts with a manual blood glucose measurement BG entry accompanied by the blood glucose measurement time $BG_{Time}$ at block 1002. At block 1080, an interactive popup asks the user if the blood glucose is a "Scheduled BG" or a miscellaneous ('Misc") blood glucose test that is not scheduled. If the user chooses "Misc", then the SubQ for Tube-Fed Patients process 1000, at block 1012, assigns a value of "Misc" to the field BGype and records the date-time stamp ("Recorded time"). At block 1030, the SubQ for Tube-Feeding process 1000 determines a correction dose CB for the manual blood glucose measurement, using EQ. 2. The SubQ for Tube-Fed patients process 1000 displays the correction dose CB on the display 116, 146, to the patient 10, nurse and doctor 40 at block 1040 and stores the value in non-transitory memory 24, 114, 144 at block 1042.

Returning to block 1080, if the user chooses "Scheduled BG", the SubQ for Tube-Fed Patients process 1000 determines, at block 1004, if the blood glucose time $BG_{Time}$ is within the interval from $(T_{sched}1-M_{Start})$ to $(T_{sched}1+M_{End})$. If the blood glucose measurement time $BG_{Time}$ is within the interval, i.e., $(T_{sched}1-M_{Start}) < BG_{Time} (T_{sched}1+M_{End})$, then the SubQ for Tube-Fed Patients process 1000, at block 1014, assigns the value "BG1" to the field BGtype, resets the countdown timer to $T_{sched}2$ and displays a reminder of the next BG time on the display 116, 146 at block 1040. Then, the SubQ for Tube-Fed Patients process 1000, at block 1022, determines the correction dose CB based on the blood glucose value BG1, using EQ. 2:

$$CB=(BG-BG_{Target})/CF \qquad (2)$$

or using the Correction Dose Function, process 700. The SubQ for Tube-Fed patients process 1000 displays the correction dose CB on the display 116, 146, to the patient 10, nurse and doctor 40 at block 1040 and stores the value in non-transitory memory 24, 114, 144 at block 1042. Additionally, the SubQ for Tube-Fed Patients process 1000, at block 1044, uses the blood glucose value BG1 as the governing BG for adjusting the value of the four Equal-Boluses (EqBolus). Specifically, at block 1044, the SubQ for Tube-Fed Patients process 1000 uses the blood glucose value BG1 as the input value BGgov for the Adjustment Factor (AF) function for determining a value for the AF. The SubQ for Tube-Fed Patients process 1000, at block 1046, retrieves the Previous Day's Recommended Equal-Bolus from memory 24, 114, 144, and at block 1048, determines a new value for the Recommended Equal-Bolus (e.g., all four EqBolus) by multiplying the AF value from block 1044 by the Previous Day's Recommended Equal-Bolus from block 1046. The SubQ for Tube-Fed patients process 1000 displays the Recommended Equal-Bolus (EqBolus) on the display 116, 146, to the patient 10, nurse and doctor 40 at block 1040 and stores the value in non-transitory memory 24, 114, 144 at block 1042.

However, if at block 1004 the SubQ for Tube-Fed Patients process 1000 determines that the blood glucose measurement time $BG_{Time}$ is not within the interval from $(T_{sched}1-M_{Start})$ to $(T_{sched}1+M_{End})$, the SubQ for Tube-Fed Patients process 1000 determines if the blood glucose measurement time $BG_{Time}$ is within a second interval $(T_{sched}2-M_{Start})$ to $(T_{sched}2+M_{End})$ at block 1006, and if so, then the SubQ for Tube-Fed Patients process 1000 at block 1016 assigns the value "BG2" to the field BGtype, resets the countdown timer to $T_{sched}3$ and displays a reminder of the next BG time on the display 116, 146 at block 1040. Then, the SubQ for Tube-Fed Patients process 1000, at block 1024, determines the correction dose CB based on the blood glucose value BG2, using EQ. 2 or using the Correction Dose Function, process 700.

The SubQ for Tube-Fed patients process 1000 displays the correction dose CB on the display 116, 146, to the patient 10, nurse and doctor 40 at block 1040 and stores the value in non-transitory memory 24, 114, 144 at block 1042. Additionally, the SubQ for Tube-Fed Patients process 1000, at block 1036, uses the blood glucose value BG2 as the governing BG for adjusting the Basal dose. Specifically, at block 1036, the SubQ for Tube-Fed Patients process 1000 uses the blood glucose value BG2 as the input value BGgov for the Adjustment Factor (AF) function for determining a value for the AF.

The SubQ for Tube-Fed Patients process 1000, at block 1056, retrieves the last Basal dose of the previous day $RecBasal_{Last}$ from memory 24, 114, 144, and at block 1058, determines a current day's Recommended Basal Dose RecBasal by multiplying the AF value by the $RecBasal_{Last}$, as follows:

$$RecBasal=(RecBasal_{Last})*AF \qquad (37)$$

The SubQ for Tube-fed patients process 1000 displays the RecBasal on the display 116, 146, to the patient 10, nurse and doctor 40 at block 1040 and stores the value in non-transitory memory 24, 114, 144 at block 1042.

However, if at block 1006 the SubQ for Tube-Fed Patients process 1000 determines that the blood glucose measurement time $BG_{Time}$ is not within the interval from $(T_{sched}2-M_{Start})$ to $(T_{sched}2+M_{End})$, the SubQ for Tube-Fed Patients process 1000 determines if the blood glucose measurement time $BG_{Time}$ is within a third interval $(T_{sched}3-M_{Start})$ to $(T_{sched}3+M_{End})$ at block 1008, and if so, then the SubQ for Tube-Fed Patients process 1000 at block 1018 assigns the value "BG3" to the field BGtype, resets the countdown timer to $T_{sched}4$ and displays a reminder of the next BG time on the display 116, 146 at block 1040. Then, the SubQ for Tube-Fed Patients process 1000, at block 1026, determines the correction dose CB based on the blood glucose value BG3, using EQ. 2 or using the Correction Dose Function, process 700.

However, if at block 1008 the SubQ for Tube-Fed Patients process 1000 determines that the blood glucose measurement time $BG_{Time}$ is not within the interval from ($T_{sched}3-M_{Start}$) to ($T_{sched}3+M_{End}$), the SubQ for Tube-Fed Patients process 1000 determines if the blood glucose measurement time $BG_{Time}$ is within a fourth interval ($T_{sched}4-M_{Start}$) to ($T_{sched}4+M_{End}$) at block 1010, and if so, then the SubQ for Tube-Fed Patients process 1000 at block 1020 assigns the value "BG4" to the field BGtype, resets the countdown timer to $T_{sched}1$ and displays a reminder of the next BG time on the display 116, 146 at block 1040. Then, the SubQ for Tube-Fed Patients process 1000, at block 1028, determines the correction dose CB based on the blood glucose value BG4, using EQ. 2 or using the Correction Dose Function, process 700.

Figure 11:
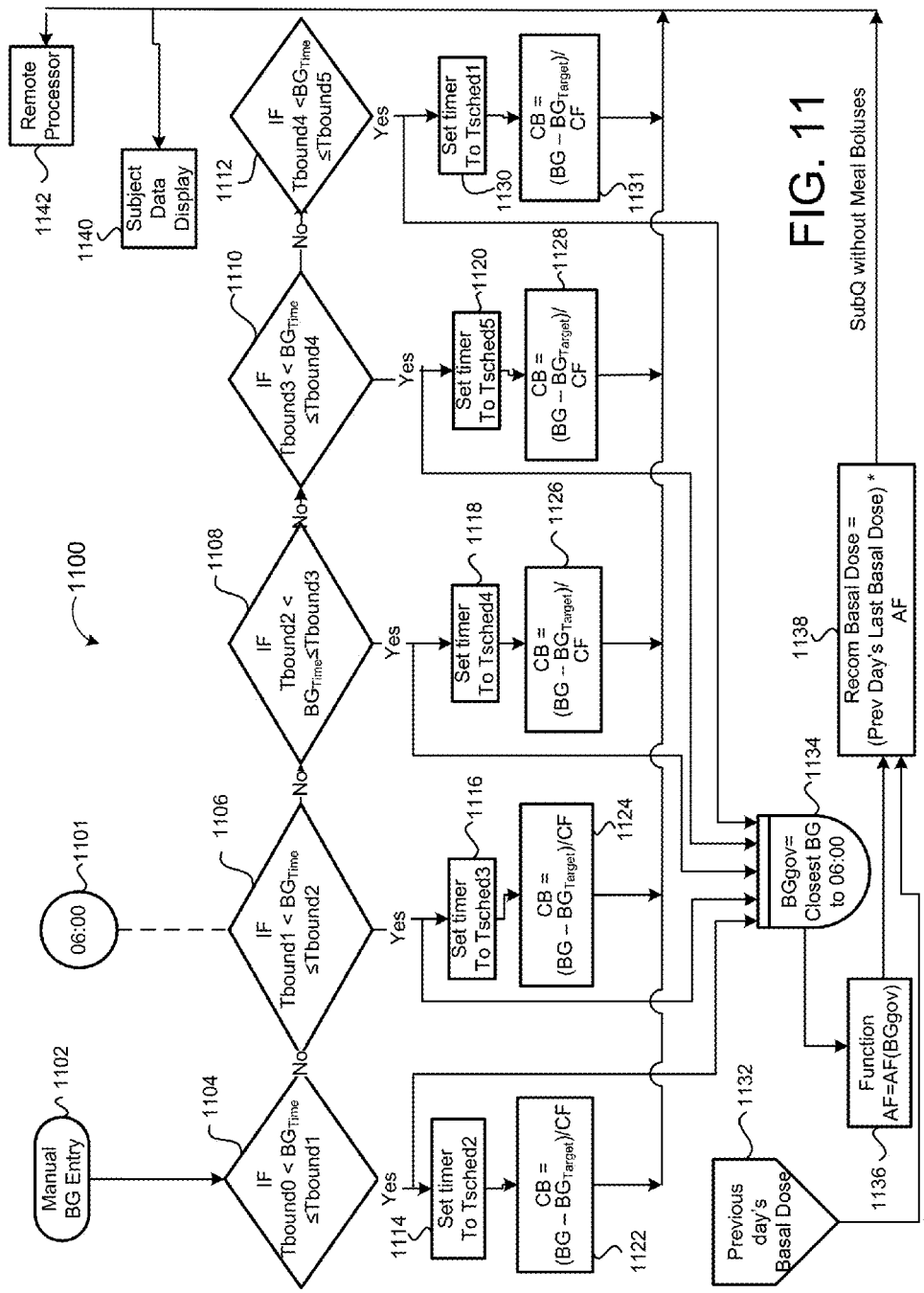
FIG. 11 is a schematic view of an exemplary subcutaneous process without meal boluses.

FIG. 11 describes a SubQ Without Meal Boluses process 1100, where the blood glucose measurements BG are deferred until after the meals, resulting in large after-meal correction boluses that incorporate insulin to cover the meals. The SubQ Without Meal Boluses process 1100 divides the day into intervals that may be of equal duration or unequal duration. Each interval includes a scheduled blood glucose measurement BG. In some examples, the SubQ Without Meal Boluses process 1100 includes five blood glucose measurements BG per day. The SubQ Without Meal Boluses process 1100 may be configured to include other numbers of time intervals. In addition, the SubQ Without Meal Boluses process 1100 includes configurable blood glucose BG measurement times. In some examples, the measurement schedule includes blood glucose measurements BG places about one to three hours after regular mealtimes, which is an appropriate timing for post-meal correction.

The scheduled Blood glucose measurement times BG times are named with a $T_{sched}0$, $T_{sched}1$, $T_{sched}2$ etc. The Time-intervals are marked by Time Boundaries, named "$T_{bound}$" with numbered subscripts. These time-values are configurable. An example of default times are shown in the following table:

TABLE 4

Default Times

| | |
|---|---|
| $T_{bound0}$ = 0:00 | $BG_{MidSleep}$: $T_{sched1}$ = 03:00 |
| $T_{bound1}$ = 05:00 | $BG_{Before-Breakfast}$: $T_{sched2}$ = 07:00 |
| $T_{bound2}$ = 08:00 | $BG_{After-Breakfast}$: $T_{sched3}$ = 10:00 |
| $T_{bound3}$ = 11:00 | $BG_{After-Lunch}$: $T_{sched4}$ = 15:00 |
| $T_{bound4}$ = 18:00 | $BG_{Bedtime}$: $T_{sched5}$ = 22:00 |

Similar to the SubQ for tube-fed patients process 1000 (FIG. 10), the SubQ Without Meal Boluses process 1100 (FIG. 11) includes a countdown timer 1101 used to obtain the blood glucose BG tests at the proper times.

To prevent the BG schedule from "migrating around the clock-face", the following method is used:

The SubQ Without Meal Boluses process 1100 determines if the time at which the blood glucose BG was measured $BG_{Time}$ falls within one of the intervals. If so, then the countdown timer is set to time-out on the next interval's scheduled blood glucose measurement $T_{sched1}$, $T_{sched2}$, $T_{sched3}$, . . . etc. This can be thought of as a "snap-to-the-schedule" feature. Each interval is configured with a start time margin ($M_{Start}$) and an end time margin ($M_{End}$). The SubQ Without Meal Boluses process 1100 may be summarized as follows:

IF [$T_{bound0}$<$BG_{Time}$≤$T_{bound1}$]; THEN Set countdown timer to time-out at $T_{sched2}$
IF [$T_{bound1}$<$BG_{Time}$≤$T_{bound2}$]; THEN Set countdown timer to time-out at $T_{sched3}$
IF [$T_{bound2}$<$BG_{Time}$≤$T_{bound3}$]; THEN Set countdown timer to time-out at $T_{sched4}$
IF [$T_{bound3}$<$BG_{Time}$≤$T_{bound4}$]; THEN Set countdown timer to time-out at $T_{sched5}$
IF [$T_{bound4}$<$BG_{Time}$≤$T_{bound0}$]; THEN Set countdown timer to time-out at $T_{sched1}$ The SubQ Without Meal Boluses process 1100 starts with a manual blood glucose measurement BG entry accompanied by the blood glucose measurement time $BG_{Time}$ at block 1102. Then at block 1104, the SubQ Without Meal Boluses process 1100 determines if the blood glucose measurement time $BG_{Time}$ is within the interval from $T_{bound0}$ to $T_{bound1}$. If the blood glucose measurement time $BG_{Time}$ is within the interval, i.e., $T_{bound0}$<$BG_{Time}$≤$T_{bound1}$, then the SubQ Without Meal Boluses process 1100, at block 1114, resets the countdown timer to $T_{sched2}$. Then the SubQ Without Meal Boluses process 1100, determines a correction dose CB at block 1122, using EQ. 2.

However, if at block 1104 the SubQ Without Meal Boluses process 1100 determines that the blood glucose measurement time $BG_{Time}$ is not within the interval from $T_{bound0}$ to $T_{bound1}$, the SubQ Without Meal Boluses process 1100 determines if the blood glucose measurement time $BG_{Time}$ is within a second interval $T_{bound1}$ to $T_{bound2}$, and if so then the SubQ Without Meal Boluses process 1100 at block 1116, resets the countdown timer to $T_{sched}3$ and at block 1124, determines a correction dose CB, using EQ. 2.

However, if at block 1106 the SubQ Without Meal Boluses process 1100 determines that the blood glucose measurement time $BG_{Time}$ is not within the interval from $T_{bound1}$ to $T_{bound2}$, the SubQ Without Meal Boluses process 1100 determines if the blood glucose measurement time $BG_{Time}$ is within a third interval $T_{bound2}$ to $T_{bound3}$ at block 1108, and if so then the SubQ Without Meal Boluses process 1100 at block 1118, resets the countdown timer to $T_{sched}4$ and at block 1126, determines a correction dose CB, using EQ. 2.

However, if at block 1108 the SubQ Without Meal Boluses process 1100 determines that the blood glucose measurement time $BG_{Time}$ is not within the third time interval from $T_{bound2}$ to $T_{bound3}$, the SubQ Without Meal Boluses process 1100 determines if the blood glucose measurement time $BG_{Time}$ is within a fourth interval $T_{bound3}$ to $T_{bound4}$, and if so then the SubQ Without Meal Boluses process 1100 at block 1120, resets the countdown timer to $T_{sched5}$ and at block 1128, determines a correction dose CB, using EQ. 2.

However, if at block 1110 the SubQ Without Meal Boluses process 1100 determines that the blood glucose measurement time $BG_{Time}$ is not within the fourth time interval from $T_{bound3}$ to $T_{bound4}$, the SubQ Without Meal Boluses process 1100 determines if the blood glucose measurement time $BG_{Time}$ is within a fifth interval $T_{bound4}$ to $T_{bound5}$, and if so then the SubQ Without Meal Boluses process 1100 at block 1130, resets the countdown timer to $T_{sched1}$ and at block 1131, determines a correction Dose CB, using EQ. 2.

As shown, the SubQ Without Meal Boluses process 1100 repeats itself five times since there are five scheduled blood glucose measurement BG; however, the SubQ Without Meal Boluses process 1100 may include more or less time intervals.

The SubQ Without Meal Boluses process 1100 adjusts the basal insulin dosage by first determining the Governing blood glucose $BG_{gov}$ at block 1134. The SubQ Without Meal Boluses process 1100 determines the Governing blood glucose $BG_{gov}$ as the blood glucose BG closest to 06:00 earlier on the same day as the basal dose whose recommendation is being calculated. To insure that the closest blood glucose BG is obtained, the basal dose is not allowed until an elapsed time after 06:00 equal to the elapsed time from the preceding BG until 0600. This is to insure that all opportunity for "another BG closer to 0600" has passed.

The SubQ Without Meal Boluses process 1100 passes the Governing blood glucose $BG_{gov}$ from block 1134 to block 1136, which determines the adjustment factor AF (see FIG. 8) and passes it to block 1138. At block 1138, the SubQ Without Meal Boluses process 1100 determines the current day's recommended first basal dose using the following equation:

$$RecBasal_{First} = (RecBasal_{Last(prev)}) * AF, \quad (38)$$

The basal dose may be one of several administered to the patient 10 during the day, but all the doses are kept at the same value.

The process 1000 displays the correction dose CB and the recommended basal dose on the display 116, 146, to the patient 10, nurse and doctor 40 at block 1140 and stores the values in non-transitory memory 24, 114, 144 at block 1142.

Figure 12A:
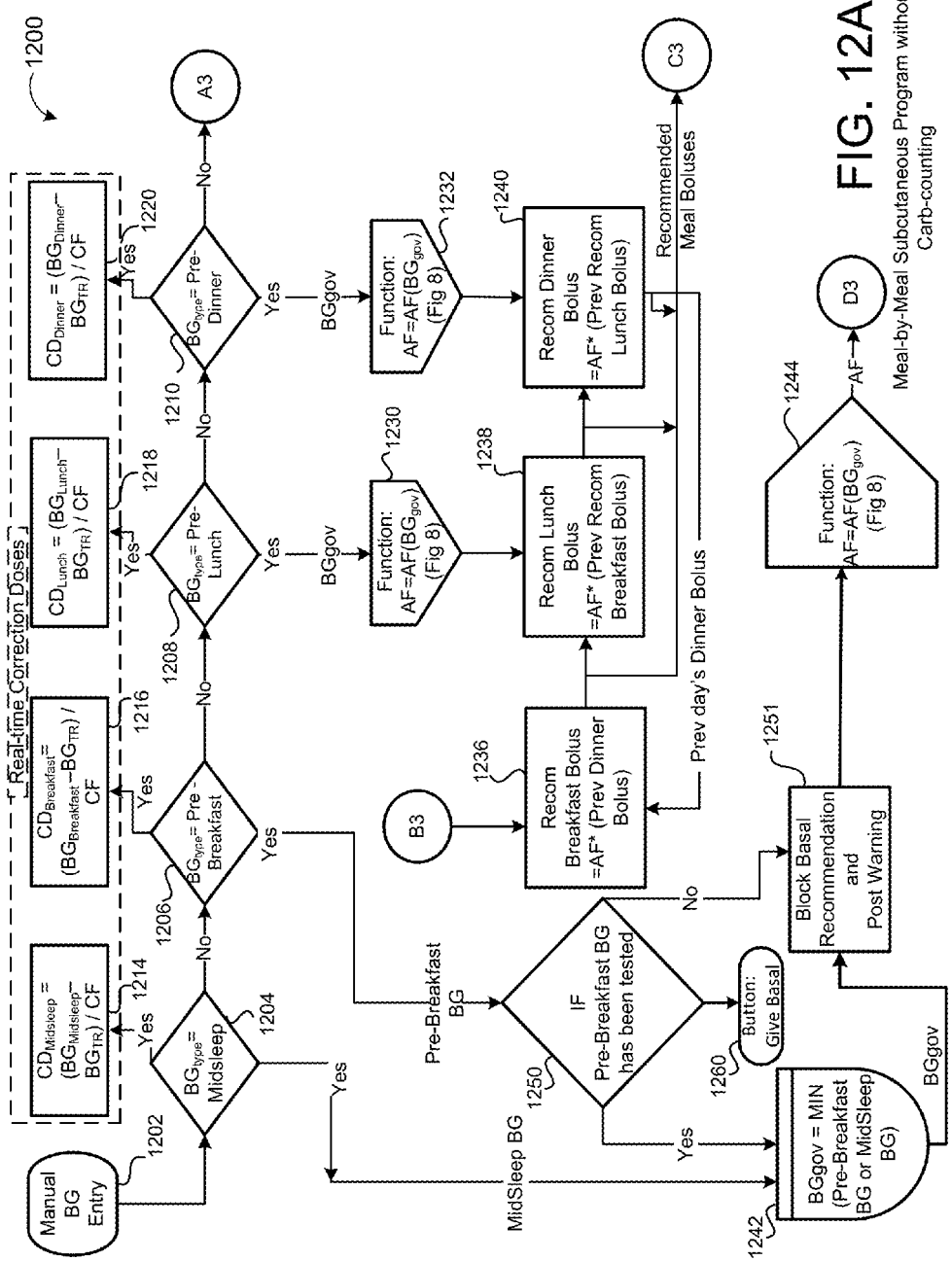
FIGS. 12A and 12B are a schematic view of an exemplary meal-by-meal subcutaneous process without carbohydrate counting.
Figure 12B:
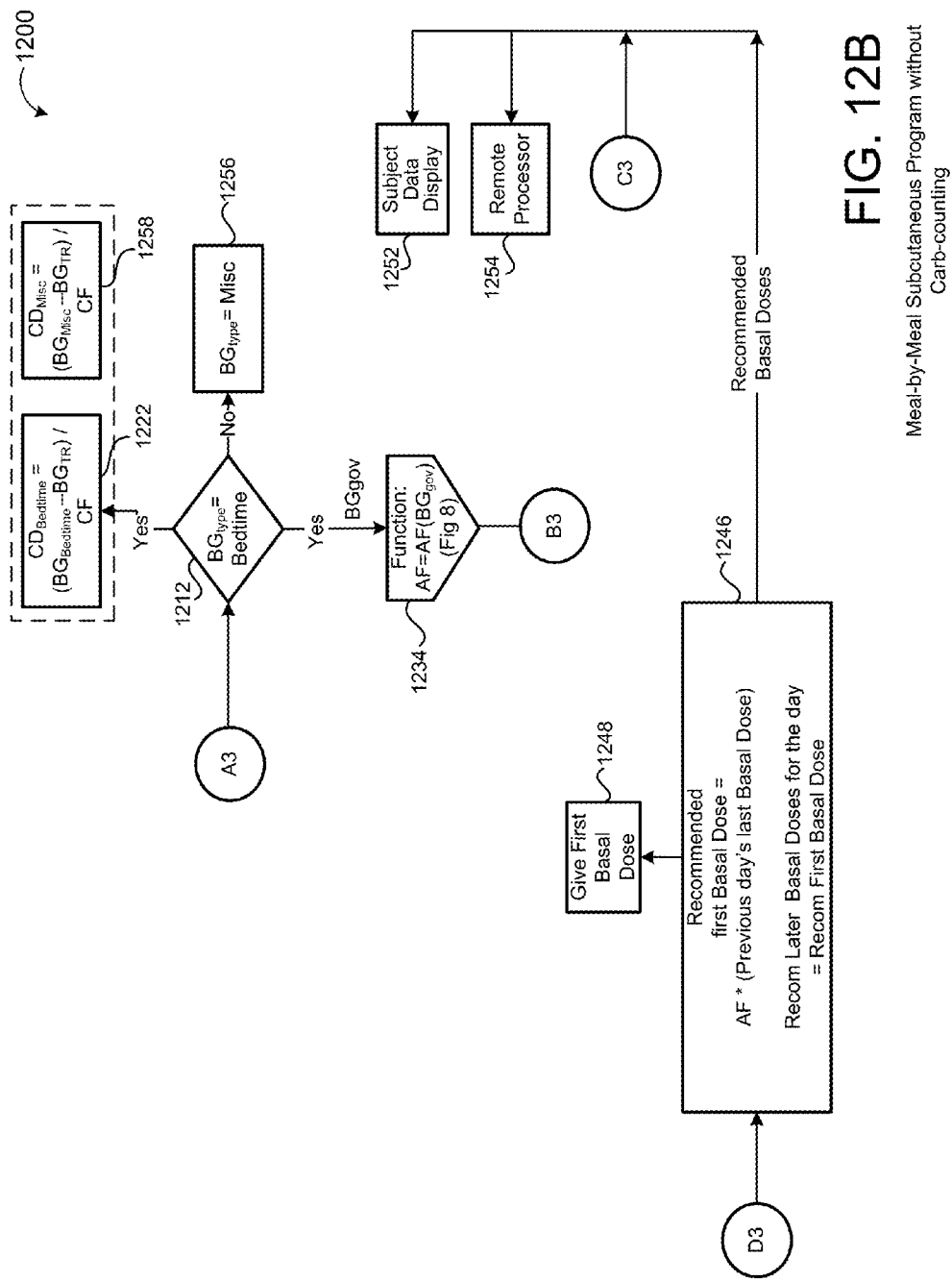

Referring to FIG. 12, the Meal-by-Meal SubQ Without Carbohydrate-counting process 1200 calculates the Recommended Meal Bolus by employing the preceding Meal Bolus (of any type or time-of-day) as the Governing Meal Bolus $MB_{gov}$ and employing the next blood glucose following the Governing Meal Bolus as the Governing Blood Glucose $BG_{gov}$. This means $BG_{gov}$ is often the current BG in real-time.

The Correction Boluses and Basal Dose adjustment are conducted similar to the Standard SubQ process 900 (FIGS. 9A and 9B). Therefore, a correction dose is determined at blocks 1214, 1216, 1218, 1220, 1222, 1258 based on the blood glucose type.

The Meal Bolus Adjustment portion of the Meal-by-Meal without Carbohydrate-counting SubQ process 1200 begins with a manual blood glucose measurement BG entry at block 1202. If the blood glucose measurement BG is determined by block 1204 to be a blood glucose type $BG_{type}$ of a Midsleep BG, then the process 900 sends the blood glucose measurement to block 1242. If the blood glucose measurement BG is not a blood glucose type $BG_{type}$ of a Midsleep BG, then Meal-by-Meal Without carbohydrate counting SubQ process 1200 determines at block 1206 whether the BG is a pre-Breakfast blood glucose $BG_{Breakfast}$. If the BG is determined at block 1206 to be a pre-Breakfast blood glucose $BG_{Breakfast}$, then at block 1250, the process 1200 determines if the pre-breakfast blood glucose $BG_{Breakfast}$ has been tested, if not then the process 1200 blocks basal recommendation, and blocks the initiation of the Give Basal popup at button 1260, and posts a warning, displayed on the display 116, 146, to the patient 10, nurse and doctor 40 at block 1254 and is stored in the non-transitory memory 24, 114, 144 at block 1251. However, if the pre-breakfast blood glucose $BG_{Breakfast}$ has been tested, then the process 1200 selects, at block 1242, the Governing blood glucose $BG_{gov}$ as the lesser of the two blood glucose values, i.e., the midsleep blood glucose $BG_{MidSleep}$ or the pre-breakfast blood glucose $BG_{Breakfast}$ as shown in EQ. 28 (above).

After determining the governing blood glucose $BG_{gov}$, the process 1200 determines the adjustment factor AF at block 1244 (see. FIG. 8). The adjustment factor process 800, returns the adjustment factor AF as a function of the governing blood glucose $BG_{gov}$. The process 1200 sends the adjustment factor AF to block 1246, where the process 1200 determines the adjustment to the patient's insulin dose by the following EQ. 30, then the nurse 40 give the patient 10 the Recommended basal dose RecomsBasal at block 1248.

If the Meal-by-Meal without carbohydrate counting SubQ process 1200, at block 1206, determines that the blood glucose measurement BG is not a pre-breakfast blood glucose measurement $BG_{Breakfast}$, then it is passed to block 1208 where a determination is made whether the blood glucose measurement BG is a pre-Lunch blood glucose $BG_{Lunch}$. If it is a pre-Lunch blood glucose $BG_{Lunch}$, then block 1208 routes the pre-Lunch BG to block 1230 where it is used as the input (BGgov) for the AF Function. The AF Function returns a value of the Adjustment Factor (AF), which is routed to block 1238 where the Recommended Lunch Bolus is calculated by the following equation:

$$RecLunchBol = AF * RecBreakfastBol_{Prev} \quad (39)$$

The process 1200 sends the Recommended Lunch Bolus RecLunchBolus to the remote processor at block 1254, to the display 114, 146, at block 1252, and to block 1240 for Dinner bolus calculation.

If the blood glucose BG is determined at block 1208 to not be a pre-Lunch blood glucose $BG_{Lunch}$, then it is routed to block 1210. If the BG is determined by block 1210 to be a pre-Dinner blood glucose $BG_{Dinner}$, then the blood glucose BG is routed to block 1232 where it is used as the input ($BG_{gov}$) for the adjustment factor process 00. The AF Function returns a value of the Adjustment Factor AF, which is routed to block 1240. The preceding Recommended Lunch Bolus is available at block 1240, which has all the necessary data to calculate the Recommended Dinner Bolus by the following equation:

$$RecDinnerBol = AF * (RecLunchBol_{Prev}) \quad (40)$$

The process 1200 sends the Recommended Dinner Bolus, RecDinnerBol to the remote processor at block 1254, to the display 114, 146, block 1252, and to block 1236 for the next day's Breakfast bolus calculation.

If the process 1200 determines the blood glucose BG at block 1210 to not be a pre-Dinner BG, then the process 1200 routes the blood glucose BG to block 1212. If the process 1200 determines the blood glucose BG at block 1212 to be a Bedtime BG, then the process 1200 routes the BG to block 1234 where it is used as the input ($BG_{gov}$) for the AF Function. The AF Function returns a value of the Adjustment Factor (AF), which is routed to block 1236. The preceding Recommended Dinner Bolus (from the previous day) is available at block 1236, which has all the necessary data to calculate the Recommended Breakfast Bolus by the following equation:

$$RecBreakfastBol = AF * (RecDinnerBol_{Prev}) \quad (41)$$

The process 1200 sends the Recommended Breakfast Bolus to the remote processor at block 1254, to the Subject Data Display, block 1252, and to block 1238 for Lunch bolus calculation.

The Meal-by-Meal SubQ With Carbohydrate-counting program calculates the Recommended Meal Bolus by dividing the carbohydrates in the upcoming meal by CIR (Carbohydrate-to-Insulin Ratio). The Carbohydrate-to-Insulin Ratio CIR is in the form of a single parameter that is re-calculated at each meal and passed to the next meal. The Governing CIR is defined as the CIR passed to the current meal from the preceding meal. The process employs the next blood glucose BG following the Governing CIR as the Governing BG ($BG_{gov}$). This means $BG_{gov}$ is often the current BG in real-time.

The Correction Boluses and Basal Dose adjustment are conducted similar to the Standard SubQ process 900 (FIGS. 9A and 9B). Therefore, a correction dose CB is determined at blocks 1314, 1316, 1318, 1320, 1322, 1258 based on the blood glucose type.

Figure 13A:
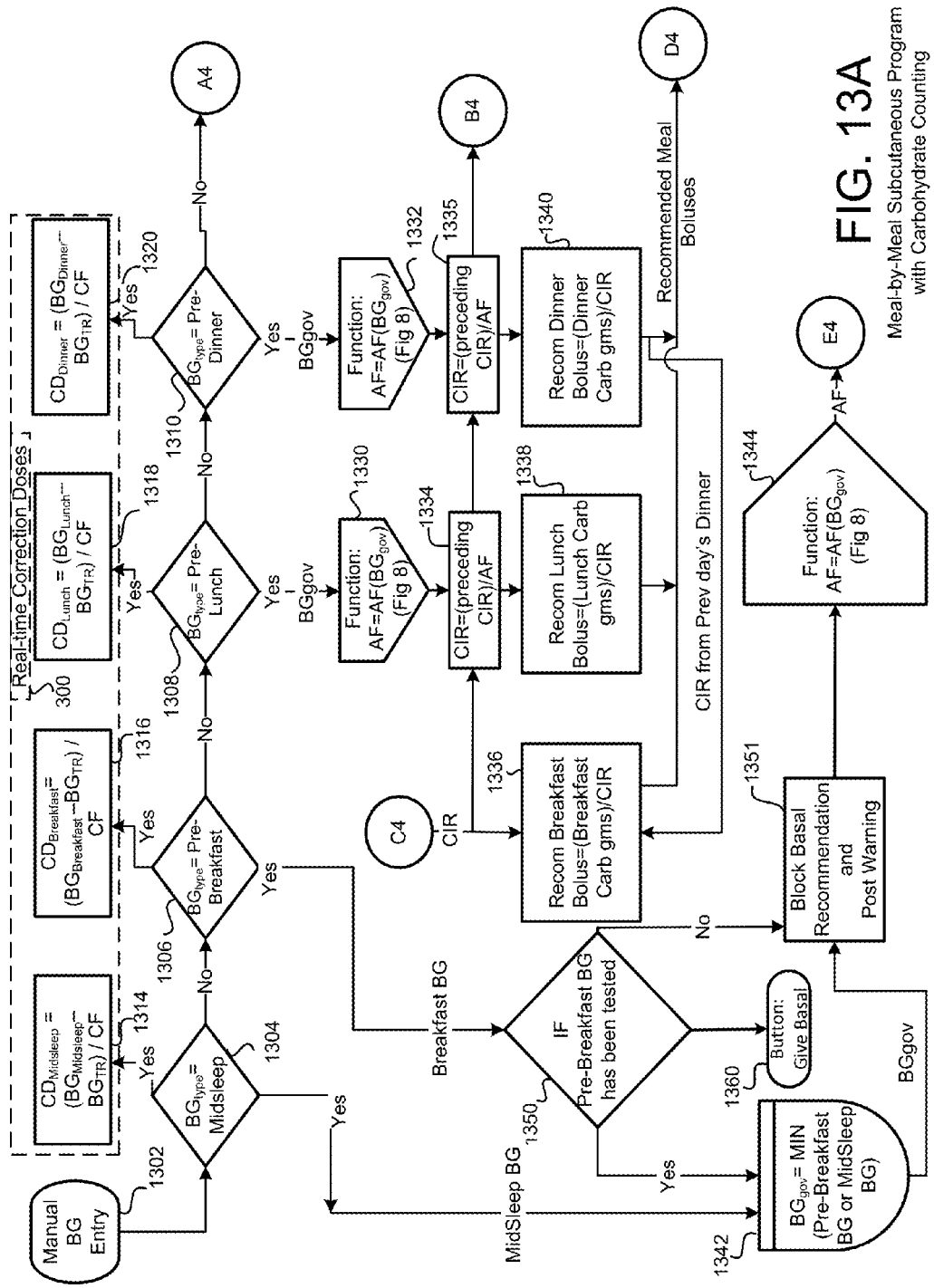
FIGS. 13A and 13B are a schematic view of an exemplary meal-by-meal subcutaneous process with carbohydrate counting.
Figure 13B:
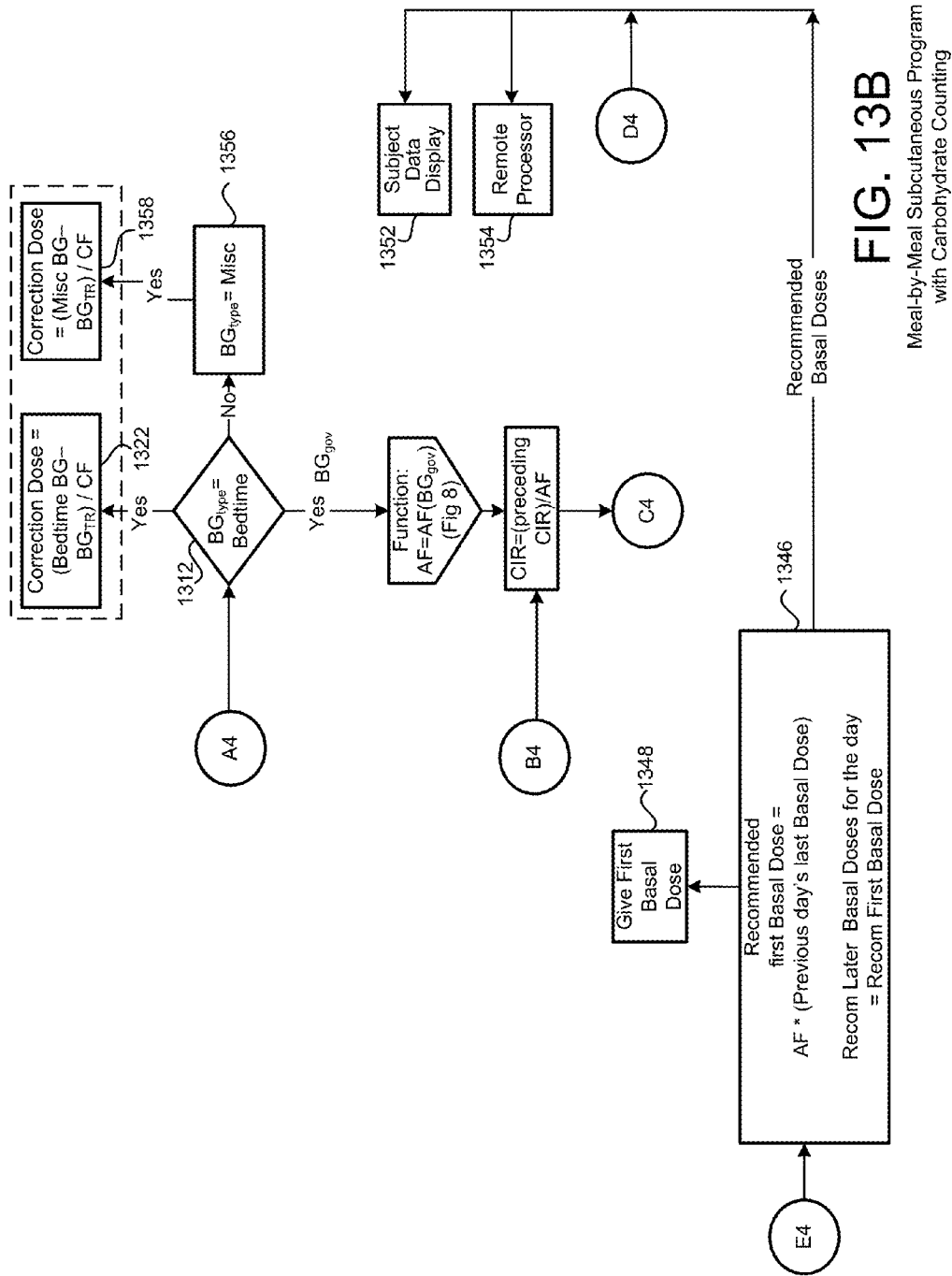
Figure 14A:
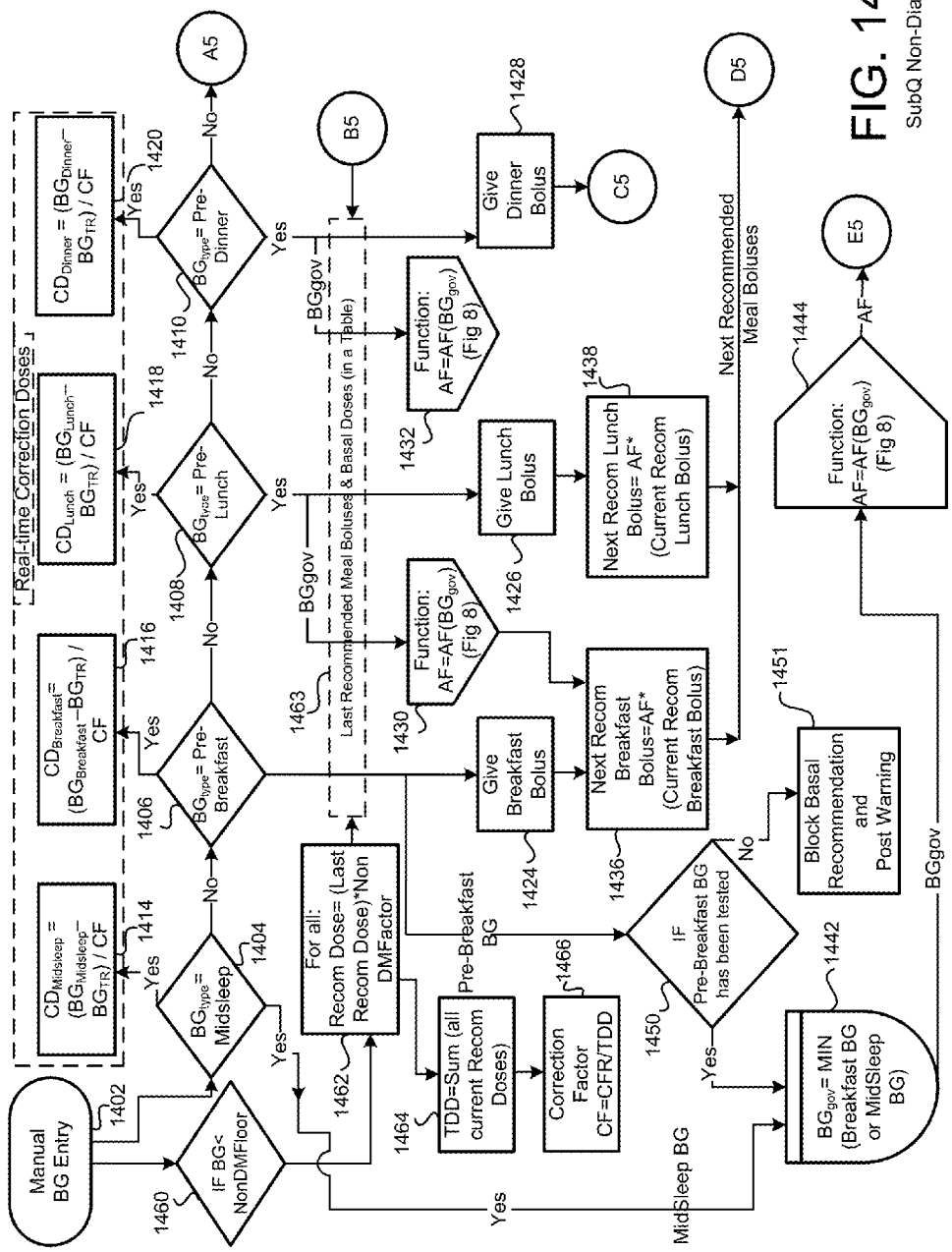
FIGS. 14A and 14B are a schematic view of an exemplary subcutaneous non-diabetic process.
Figure 14B:
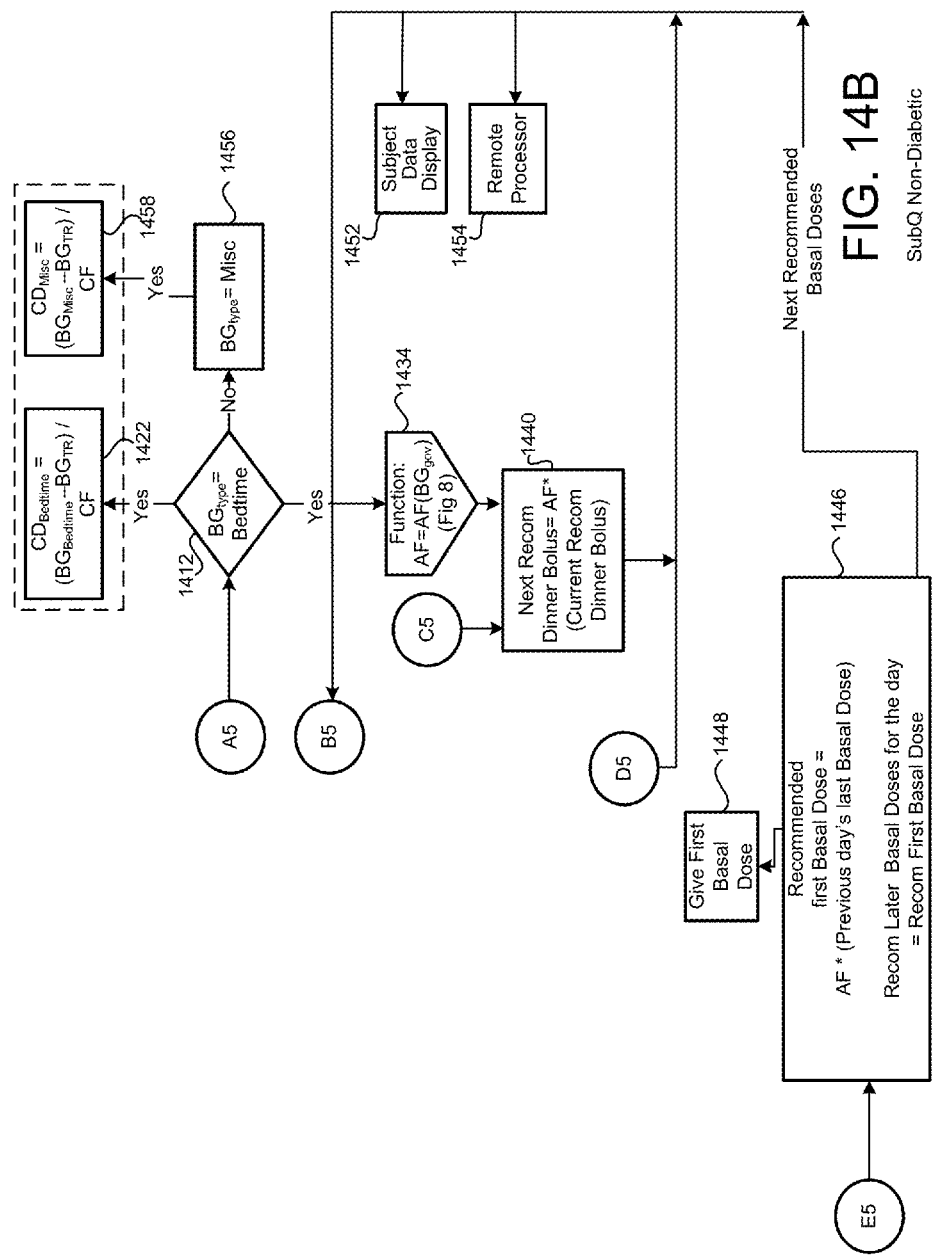

Referring to FIGS. 13A and 13B, the Meal Bolus Adjustment portion of the Meal-by-Meal Process 1300 begins with a manual BG entry at block 1302. If the process 1300 determines the blood glucose value BG at block 1304 to not be a Midsleep BG, then the process 1300 makes a determination at block 1306 whether the BG is a pre-Breakfast BG. If the process 1300 determines the blood glucose BG at block 1308 to be a pre-Breakfast blood glucose $BG_{breakfast}$, then at block 1350, the process 1300 determines if the pre-breakfast blood glucose $BG_{Breakfast}$ has been tested. If not, then the process 1300 blocks basal recommendation, and blocks the initiation of the Give Basal dialog at button 1360, and posts a warning, displayed on the display 116, 146, to the patient 10, nurse, and doctor 40 at block 1354. The process 1300 stores the warning in the non-transitory memory 24, 114, 144 at block 1351. If, however, the pre-breakfast blood glucose $BG_{Breakfast}$ has been tested, then the process 1300 selects, at block 1342, the Governing blood glucose $BG_{gov}$ as the lesser of the two blood glucose values, i.e., the midsleep blood glucose $BG_{MidSleep}$ or the pre-breakfast blood glucose $BG_{Breakfast}$, as shown in EQ. 28 (above).

After determining the governing blood glucose $BG_{gov}$, the process 1300 determines the adjustment factor AF at block 1344 (see. FIG. 8). The adjustment factor process 800 returns the adjustment factor AF as a function of the governing blood glucose $BG_{gov}$. The process 1300 sends the adjustment factor AF to block 1246, where the process 1300 determines the adjustment to the patient's insulin dose by the following EQ. 30, then the nurse 40 gives the patient 10 the Recommended basal dose RecomsBasal at block 1348.

If the process 1300 determines the blood glucose BG at block 1306 to not be a pre-Breakfast BG, then the process 1300 passes the blood glucose BG to block 1308, where the process 1300 determines whether the blood glucose BG is a pre-lunch blood glucose $BG_{Lunch}$. If the blood glucose BG is a pre-Lunch blood glucose $BG_{lunch}$, then the process 1300, at block 1308, routes the pre-lunch blood glucose $BG_{lunch}$ to block 1330, where it is used as the input ($BG_{gov}$) for the adjustment factor AF Function. The adjustment factor AF Function (FIG. 8) returns a value of the Adjustment Factor AF, which is routed to block 1334 where the Carbohydrate-to-Insulin Ratio (CIR) is calculated by the following formula:

$$CIR=(CIR \text{ from Breakfast})/AF \qquad (42)$$

The Meal-by-Meal with Carb-Counting process 1300 routes the Carbohydrate-to-Insulin Ratio CIR to block 1338 where the Recommended Lunch Bolus is calculated as follows:

$$RecLunchBolus=(Carbohydrate \text{ gms in Lunch})/CIR \qquad (43)$$

The Carbohydrate-to-Insulin Ratio CIR is also sent from block 1334 to block 1336 for use in the upcoming Dinner calculations.

If the process 1300 determines the blood glucose BG at block 1308 to not be a pre-lunch blood glucose $BG_{lunch}$, then the process 1300 routes the blood glucose BG to block 1310. If the process 1300 determines the blood glucose BG at block 1310 to be pre-dinner blood glucose $BG_{dinner}$, then the process 1300 routes the blood glucose BG to block 1332, where it is used as the input ($BG_{gov}$) for the adjustment factor AF Function. The adjustment factor AF Function returns a value of the Adjustment Factor (AF), which the process 1300 routes to block 1336, where the Carbohydrate-to-Insulin Ratio CIR is calculated by the following formula:

$$CIR=(CIR \text{ from Lunch})/AF \qquad (44)$$

The Meal-by-Meal with Carb-Counting process 1300 routes the CIR to block 1340 where the Recommended Dinner Bolus is calculated as follows:

$$RecDinnerBol=(Carbohydrate \text{ gms in Dinner})/CIR \qquad (45)$$

The Carbohydrate-to-Insulin Ratio CIR is also sent from block 1336 to block 1332 for use in the upcoming Breakfast calculations. The process 1300 sends the Recommended Dinner Bolus, RecomDinnerBol to the remote processor at block 1354, and to the display 114, 146, block 1352.

If the process 1300 determines the blood glucose BG at block 1310 to not be a pre-Dinner BG, then the process 1300 routes the blood glucose BG to block 1312. If the process 1300 determines the blood glucose BG at block 1312 to be a Bedtime BG, then the process 1300 routes the blood glucose BG to block 1330, where it is used as the input (BGgov) for the AF Function. The AF Function returns a value of the Adjustment Factor (AF), which is routed to block 1332, where the Carbohydrate-to-Insulin Ratio (CIR) is calculated by the following formula at block 1334:

$$CIR=(CIR \text{ from Dinner})/AF \qquad (46)$$

The Meal-by-Meal with Carb-Counting process 1300 routes the CIR to block 1336 where the Recommended Breakfast Bolus is calculated as follows:

$$RecBreakfastBol=(Carbohydrate \text{ gms in Breakfast})/CIR \qquad (47)$$

The CIR is also sent from block 1330 to block 1334 for use in the upcoming Lunch calculations. The process 1300 sends the Recommended Breakfast Bolus to the remote processor at block 1354, and to the Subject Data Display at block 1352.

FIG. 14 shows a subcutaneous process 1400 for non-diabetic patients 10 who have a temporary condition of diabetes-like symptoms. A typical example is stress-hyperglycemia, a condition that is encountered when the patient's body is under stress due to surgery, certain medications, or another disease other than diabetes. The stress causes the patient's body to react by raising the blood glucose. As the patient recovers, this hyperglycemic condition typically disappears, sometimes rapidly, leaving the patient without need of insulin. The principle of the process is to rapidly reduce the entire insulin dosing regimen of the patient by a factor NonDMfactor, whenever a blood glucose measurement BG falls below a threshold.

The Non-DM process 1400 begins at block 1402 with a blood glucose measurement BG. The process 1400 determines at block 1460 if the blood glucose BG is below a threshold for insulin reduction NonDMfloor. If the blood glucose BG is less than the values of the last recommended NonDMfloor, the process 1400 reduces, at block 1462, the value of all the last-recommended insulin doses in a table at block 1463, by multiplying each value by a dimensionless configurable constant whose value is between 0 and 1, threshold for insulin reduction NonDMfactor. The group at block 1463 includes the last-recommended-doses such as Breakfast Bolus $BG_{Breakfast}$, Lunch Bolus $BG_{Lunch}$, Dinner Bolus $BG_{Dinner}$, and Basal Dose, irrespective of whether the dose has been given or not. In other words, the latest recommendation (or prescribed dose) is changed whether a dose was given or not. In many implementations, the threshold for insulin reduction NonDMfactor is configured to a value of 0.5.

Corrective insulin may also be reduced. This is accomplished by raising the Correction Factor CF as follows: Returning to block 1462, the logic is passed to block 1464, where a value of Total Daily Dose of Insulin TDD is recalculated each time the dose is reduced. This is accomplished by summing all the newly-reduced values of the last recommended values of meal boluses and basal doses. The process 1400 passes the TDD to block 1466, where a live Correction Factor is calculated as follows:

$$CF=CFR/TDD \tag{46}$$

Returning to block 1402, the process 1400 routes the blood glucose BG to block 1404 where the process 1400 determines if the blood glucose type $BG_{type}$ is MidSleep $BG_{Midsleep}$. If so, then the process 1400 routes the MidSleep blood glucose $BG_{Midsleep}$ to block 1442. If it is determined at block 1404 that the blood glucose type $BG_{type}$ is not MidSleep, the logic is passed to block 1406, where it is determined if the blood glucose type $BG_{type}$ is pre-Breakfast $BG_{Breakfast}$. If the blood glucose type $BG_{type}$ is pre-Breakfast $BG_{Breakfast}$, the process 1400 calculates a Correction dose CB at block 1416 and is administered as soon as possible. Also, if blood glucose type $BG_{type}$ is pre-Breakfast $BG_{Breakfast}$, the logic is passed to box 1424, where the previously-recommended Breakfast meal bolus is administered. The value of this previously-recommended pre-Breakfast meal bolus is passed to block 1436, where it is one of the two required parameters for calculation of the Next Recommended Breakfast Bolus. Returning to block 1406, the process 1400 routes the pre-Breakfast BG to box 1450.

The condition at block 1450 is that the administration of basal is blocked by not-posting the recommended Basal dose until the arrival of the breakfast blood glucose $BG_{Breakfast}$ from block 1406, where the pre-breakfast blood glucose $BG_{Breakfast}$ is sent to block 1442. At block 1442, the process 1400 determines the governing blood glucose $BG_{gov}$ for Basal adjustment as the lesser of the two blood glucose values, midsleep blood glucose $BG_{Midsleep}$ and pre-breakfast blood glucose $BG_{Breakfast}$. At block 1444, the process 1400 inputs the governing blood glucose $BG_{gov}$ for Basal into the Adjustment Factor AF Function (FIG. 7), which returns an Adjustment Factor AF for basal adjustment. The process 1400 sends the adjustment factor AF to block 1446, where it is used to calculate the Recommended First Basal Dose of the day by the formula:

Recommended first Basal Dose=AF*(Previous day's last Basal Dose) (48)

Basal dosing is adjusted only once per day, because a fasting blood glucose BG is needed as the governing blood glucose $BG_{gov}$, and the midsleep blood glucose $BG_{Midsleep}$ and pre-breakfast blood glucose $BG_{Breakfast}$ BG are the only reliable fasting blood glucose measurements BG during the day. If more than one basal dose is used, then the values are set to be equal to the first basal dose of the day. The last basal dose of the day is used as the Governing Basal Dose because it is the most recent dose at the time of the midsleep blood glucose $BG_{Midsleep}$ and pre-breakfast blood glucose $BG_{Breakfast}$.

If the process 1400 determines at block 1406 that the Blood Glucose type $BG_{type}$ is not Breakfast, the logic passes to block 1408, where the process 1400 determines if the $BG_{type}$ is Lunch. If the $BG_{type}$ is Lunch, the process 1400 calculates a Correction dose CB at block 1418, which is administered as soon as possible. Also, the logic passes to box 1426, where the previously-recommended Lunch meal bolus is administered. The process 1400 passes the value of this previously-recommended Lunch meal bolus to block 1438, where it is one of the two required parameters for calculation of the Next Recommended Lunch Bolus. Returning to block 1408, the process 1400 also routes the lunch blood glucose $BG_{Lunch}$ to block 1430, providing the second of the two required parameters for calculation of the Next Recommended Breakfast Bolus as follows:

Next Recom. Breakfast Bolus=AF*(Current Recom Breakfast Bolus) (49)

If it is determined at block 1408 that $BG_{type}$ is not pre-Lunch, the logic passes to block 1410, where the process 1400 determines if the $BG_{type}$ is pre-Dinner. If the $BG_{type}$ is pre-Dinner, the process 1400 calculates a Correction dose at block 1420, which is administered as soon as possible. Also, the logic is passes to box 1428, where the previously-recommended Dinner meal bolus is administered. The value of this previously-recommended Dinner meal bolus is passed to box 1440, where is one of the two required parameters for calculation of the Next Recommended Dinner Bolus. Returning to block 1410, the process 1400 also routes the pre-Dinner blood glucose $BG_{Dinner}$ to block 1432, providing the second of the two required parameters for calculation of the Next Recommended Lunch Bolus as follows:

Next Recom. Lunch Bolus=AF*(Current Recom Lunch Bolus) (50)

If it is determined at block 1410 that BGtype is not pre-Dinner, the logic passes to block 1412, where the process 1400 determines if the $BG_{type}$ is Bedtime. If the blood glucose type $BG_{type}$ is Bedtime, the process 1400 calculates a Correction dose CB at block 1422, which is administered as soon as possible. Also, the logic passes to box 1434, providing the second of the two required parameters for calculation of the Next Recommended Dinner Bolus as follows:

Next Recom. Dinner Bolus=AF*(Current Recom Dinner Bolus) (51)

If it is determined at block 1412 that the blood glucose $BG_{type}$ is not Bedtime, the logic passes to block 1456, where the process 1400 determines if the $BG_{type}$ is Bedtime. If the $BG_{type}$ is Bedtime, the process 1400 calculates a Correction dose at block 1458, which is administered as soon as possible. The process 1400 sends the next recommended meal bolus to the remote processor at block 1454, and to the display 114, 146, at block 1452.

Figure 15:
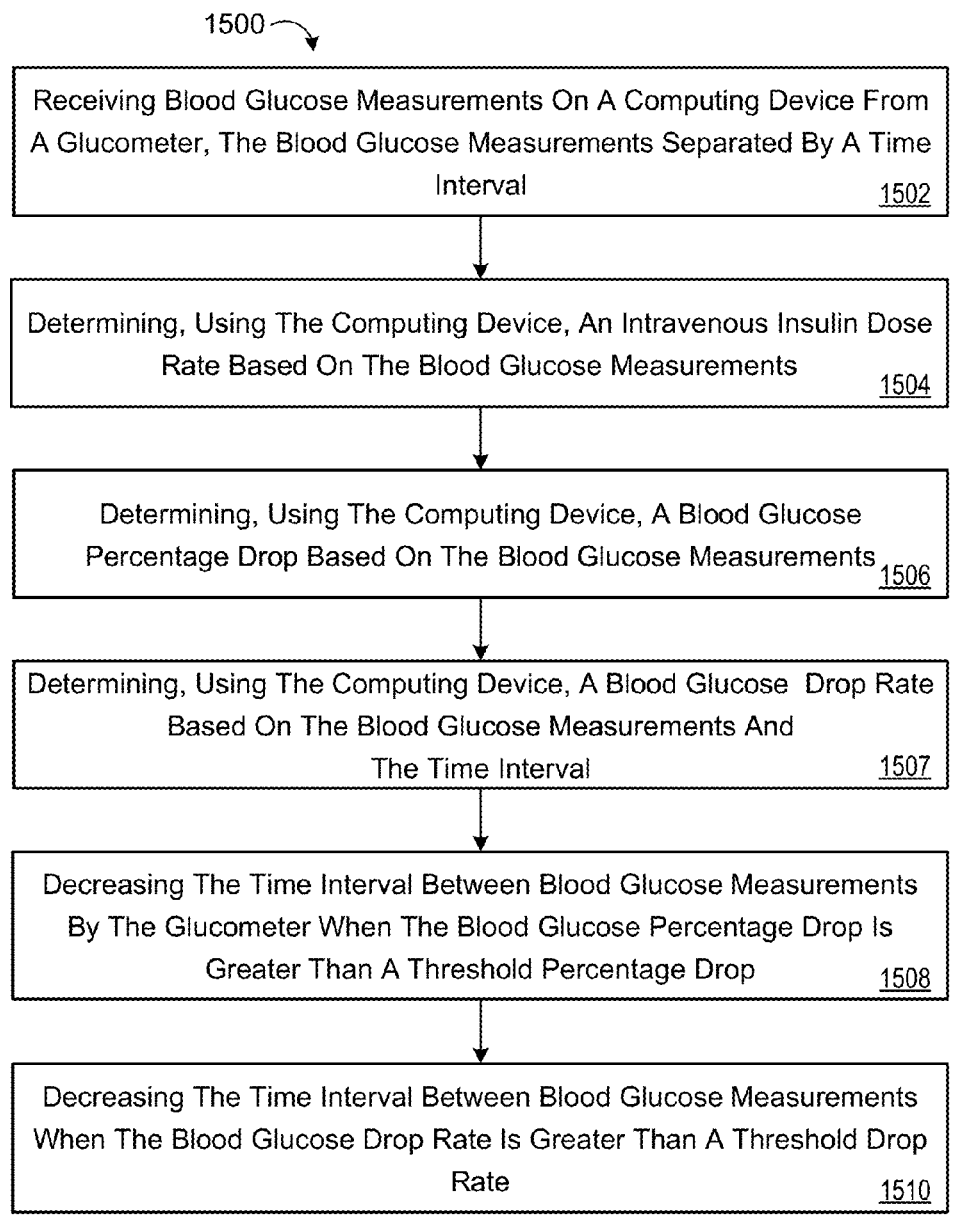
FIG. 15 is a schematic view of an exemplary arrangement of operations for administering insulin.

FIG. 15 provides an arrangement of operations for a method 1500 of administering intravenous insulin to a patient 10. The method includes receiving 1502 blood glucose measurements BG on a computing device (e.g., a processor 112 of a patient device 110, a processor 152 of a hospital electronic medical record system 150, or a data processor 132 of a service provider 130) of a dosing controller 160 from a blood glucose measurement device 124

(e.g., glucose meter or glucometer). The blood glucose measurements BG are separated by a time interval $T_{Next}$. The method 1500 includes determining 1504, using the computing device 112, 132, 142, an insulin dose rate IIR based on the blood glucose measurements BG. In some implementations, the method 1500 determines the insulin dose rate IRR based on the current blood glucose measurement BG, a constant K, and a multiplier M (see EQ. 3A above). The constant K may equal 60 mg/dl. The method 1500 includes leaving the multiplier M unchanged between time intervals $T_{Next}$ when the current blood glucose measurement BG is greater than an upper limit $BG_{TRH}$ of the blood glucose target range $BG_{TR}$ and the blood glucose percent drop $BG_{\%\ Drop}$ from the previous blood glucose value $BG_P$ is greater than or equal to a desired percent drop BG % dropM (see EQ. 5). The method also includes multiplying the multiplier M by a change factor $M_{CF}$ when the current blood glucose measurement BG is greater than an upper limit $BG_{TRH}$ of the blood glucose target range $BG_{TR}$ and the blood glucose percent drop $BG_{\%\ Drop}$ (or blood glucose percent drop) is less than the desired percent drop BG % dropM. Additionally or alternatively, the method 1500 includes leaving the multiplier M unchanged between time intervals $T_{Next}$ when the current blood glucose measurement BG is in the target range $BG_{TR}$ i.e. when BG is less than an upper limit $BG_{TRH}$ of the blood glucose target range and greater than the lower limit $BG_{TRL}$ of the target range, $BG_{TR}$. The method also includes dividing the multiplier M by a change factor $M_{CF}$ when the current blood glucose measurement BG is less than the lower limit $BG_{TRL}$ of the blood glucose target range $BG_{TR}$.

The method 1500 may include setting the time interval $T_{Next}$ to a hypoglycemia time interval $T_{Hypo}$ of between about 15 minutes and about 30 minutes, when the current blood glucose measurement BG is below a hypo-threshold blood glucose level $BG_{Hypo}$.

The method 1500 includes determining 1506 a blood glucose drop rate $BG_{DropRate}$ based on the blood glucose measurements BG and the time interval $T_{Next}$. The method 1500 includes determining 1507 a blood glucose percent drop $BG_{\%\ Drop}$, using the computing device 112, 132, 142 from a previous blood glucose measurement $BG_P$. When the blood glucose drop rate $BG_{DropRate}$ is greater than a threshold drop rate $BG_{DropRateLimit}$, the method 1500 includes decreasing at 1508 the time interval $T_{Next}$ between blood glucose measurements measure by the glucometer.

The method 1500 also includes decreasing 1510 the time interval $T_{Next}$ between blood glucose measurements BG when the percent drop $BG_{\%\ Drop}$ of the blood glucose BG is greater than the threshold of the percent drop % $Drop_{Regular}$, where the threshold of the percent drop % $Drop_{Regular}$ depends on whether the current blood glucose measurement BG is below a lower limit $BG_{TRL}$ of a blood glucose target range $BG_{TR}$. In some implementations, the method 1500 includes decreasing the time interval $T_{Next}$ when the current blood glucose measurement BG is greater than or equal to the lower limit $BG_{TRL}$ of the blood glucose target range $BG_{TR}$ and the blood glucose percent drop $BG_{\%\ Drop}$ exceeds a threshold percent drop % $Drop_{Regular}$. In some implementations, the method 1500 includes decreasing the time interval $T_{Next}$ when the current blood glucose measurement BG is below the lower limit $BG_{TRL}$ of the blood glucose target range $BG_{TR}$ and above the hypo-threshold blood glucose level $BG_{Hypo}$, and the blood glucose percent drop $BG_{\%\ Drop}$ is greater than or equal to a threshold percent drop % $Drop_{LowLimit}$.

In some examples, the method 1500 includes leaving the multiplier M unchanged for at least two subsequent time intervals, $T_{Next}$, when the current blood glucose measurement BG is a pre-meal measurement. In some examples, the method 1500 includes receiving, on the computing device 112, 132, 142, a number of carbohydrates for a meal as well as a blood glucose measurement, and determining, using the computing device 112, 132, 142, an intravenous insulin rate IIR based on the blood glucose (this IIR may be calculated using EQ. 3A). In addition, the method 1500 includes determining, using the computing device 112, 132, 142, a meal bolus insulin rate IIR based on the number of carbohydrates. The method 1500 then calculates a Total insulin rate as the sum of the meal bolus rate and the regular intravenous rate as shown in EQ. 12. The method 1500 may further include setting the time interval $T_{Next}$ to about 30 minutes. If the blood glucose measurement BG is a second consecutive measurement after (but not including) an initial pre-meal blood glucose measurement BG, the method 1500 includes setting the time interval $T_{Next}$ to about 30 minutes.

In some implementations, the method 1500 includes electronically displaying on a display 116, 146 a warning and blocking transition to a subcutaneous administration of insulin when the current blood glucose measurement BG is outside a stability target range $BG_{STR}$. In addition, the method 1500 includes electronically displaying on the display 116, 146 a warning when the current blood glucose measurement BG is within the patient's personalized target range $BG_{TR}$ for less than a threshold stability period of time $T_{Stable}$. In some examples, the method 1500 includes determining a total daily dose of insulin TDD based on the multiplier M when the current blood glucose measurement BG is within a stability target range $BG_{STR}$ for a threshold stability period of time $T_{Stable}$.

Figure 16:
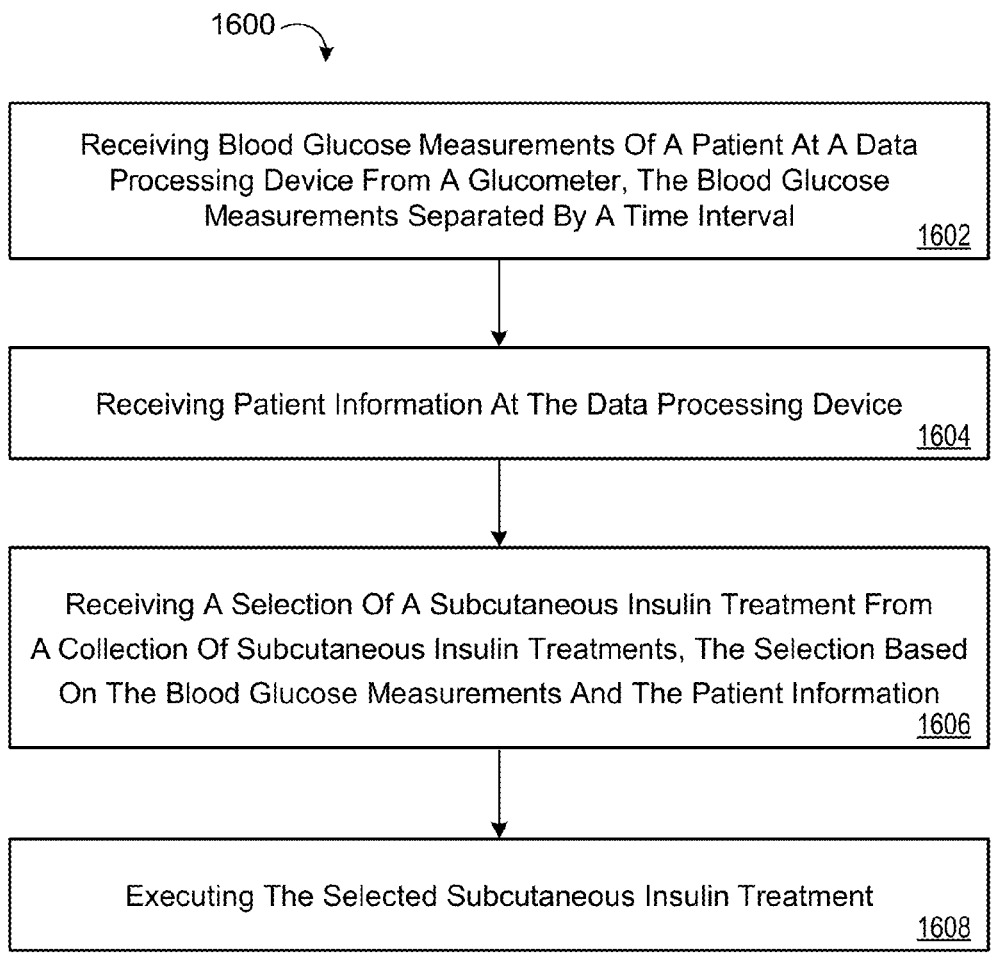
FIG. 16 is a schematic view of an exemplary arrangement of operations for administering insulin.

Referring to FIG. 16, a method 1600 of administering insulin includes receiving 1602 blood glucose measurements BG of a patient 10 at a data processing device 112 from a glucometer 124. The blood glucose measurements BG are separated by a time interval $T_{Next}$. The method 1600 also includes receiving 1604 patient information at the data processing device 112, and in some examples, storing the received patient information on non-transitory memory 24, 114, 144 associated with the processor 112. The method 1600 includes receiving 1606 a selection 226, at the data processing device 112, of a subcutaneous insulin treatment 900, 1000, 1100, 1200, 1300, 1400 from a collection of subcutaneous insulin treatments 900, 1000, 1100, 1200, 1300, 1400. The selection 226 is based on the blood glucose measurements BG and the patient information 208a. The method 1600 also includes executing 1608, using the data processing device 112, the selected subcutaneous insulin treatment 900, 1000, 1100, 1200, 1300, 1400.

In some implementations, the method 1600 includes: receiving a configurable constant CFR; storing the configurable constant CFR in non-transitory memory associated with the data processing device; and determining a correction factor. The configurable constant CFR may be determined from a published statistical correlation. The method 1600 may also include determining a pre-meal correction bolus CB, and/or a post-prandial correction bolus CB. The method 1600 may include receiving a half-life value of the rapid-acting insulin; and determining the mean lifetime iLifeRapid of the rapid-acting insulin.

In some implementations, the method 1600 includes receiving a governing blood glucose value $BG_{gov}$, and determining an adjustment factor AF based on the received governing blood glucose value $BG_{gov}$. Determining the adjustment factor AF may include determining when the governing blood glucose value $BG_{gov}$ is within a threshold range of values, and setting the adjustment factor to a preconfigured adjustment factor based on the threshold range of values. In some implementations, the method 1600 includes determining a Carbohydrate-to-Insulin Ratio CIR based on the adjustment factor AF by calculating one of EQs. 42, 44, and 46.

The selection of subcutaneous insulin treatments 900, 1000, 1100, 1200, 1300, 1400 includes one or more of a subcutaneous standard program 900, a subcutaneous for tube-fed patients program 1000, a subcutaneous program without meal boluses 1100, a meal-by-meal subcutaneous program without carbohydrate counting 1200, a meal-by-meal subcutaneous program with carbohydrate counting 1300, and a subcutaneous program for non-diabetic patients 1400. In some examples, the subcutaneous for tube-fed patients process 1000 includes: receiving a blood glucose time $BG_{Time}$ associated with a time of measuring of the blood glucose measurement BG; determining if the blood glucose time $BG_{Time}$ is within a threshold time interval; setting a timer 1001, 1101 for a next blood glucose measurement BG based on the threshold time interval; and determining a correction insulin dose CB based on the blood glucose type $BG_{Type}$.

In some examples, the standard program 900 includes determining a blood glucose type $BG_{Type}$ of the received blood glucose measurement BG; and determining a correction insulin dose CB based on the blood glucose type $BG_{Type}$. In some examples, the method 1600 includes receiving a governing blood glucose value $BG_{gov}$, and determining an adjustment factor AF based on the received governing blood glucose value and the blood glucose measurement. The method 1600 may also include determining a next recommended meal bolus based on the determined adjustment factor AF and a current recommended meal bolus.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method comprising:
   receiving, at data processing hardware, a blood glucose measurement of a patient from a glucometer;
   determining, by the data processing hardware, a blood glucose type of the received blood glucose measurement; and
   when the determined blood glucose type comprises one of a pre-lunch blood glucose measurement or a pre-dinner blood glucose measurement:
      obtaining, by the data processing hardware, a previous Carbohydrate-to-Insulin Ratio for an immediately previous meal consumed by the patient, the immediately previous meal consumed by the patient comprising one of breakfast when the determined blood glucose type comprises the pre-lunch blood glucose measurement or lunch when the determined blood glucose type comprises the pre-dinner blood glucose type;
      determining, by the data processing hardware, an adjustment factor based on the received blood glucose measurement;
      adjusting, by the data processing hardware, the previous Carbohydrate-to-Insulin Ratio for the immediately previous meal consumed by the patient by dividing the previous Carbohydrate-to-Insulin Ratio by the adjustment factor;
      determining, by the data processing hardware, a recommended meal bolus for the determined blood glucose type based on the adjusted previous Carbohydrate-to-Insulin Ratio; and
      transmitting the recommended meal bolus to an administration device in communication with the data processing hardware, the administration device comprising:
         a doser; and
         an administration computing device in communication with the doser, the administration computing device configured to cause the doser to administer a number of units of insulin to the patient using the recommended meal bolus.

2. The method of claim 1, further comprising determining, by the data processing hardware, a pre-meal correction bolus by calculating:

$$CB = (BG - BG_{Target})/CF,$$

wherein CB is the pre-meal correction bolus, BG is the received blood glucose measurement, $BG_{Target}$ is a target blood glucose value of a patient, and CF is a correction factor.

3. The method of claim 1, wherein determining the adjustment factor comprises:
  determining whether the blood glucose value is within one of a plurality of target ranges of values; and
  when the blood glucose measurement is within one of the plurality of target ranges of values, setting the adjustment factor to a target adjustment factor associated with the corresponding target range of values that includes the blood glucose measurement.

4. The method of claim 3, wherein the plurality of target ranges of values comprises:
  a first target range of values including blood glucose values less than a first configurable constant;
  a second target range of values including blood glucose values greater than or equal to the first configurable constant and less than a low target blood glucose value of a target blood glucose range for the patient;
  a third target range of values including blood glucose values greater than or equal to the low target blood glucose value and less than a high target blood glucose value of the target blood glucose range;
  a fourth target range of values including blood glucose values greater than or equal to the high target blood glucose value and less than a second configurable constant;
  a fifth target range of values including blood glucose values greater than or equal to the second configurable constant and less than a third configurable constant; and
  a sixth target range of values including blood glucose values greater than or equal to the third configurable constant.

5. The method of claim 1, wherein the blood glucose type is associated with a blood glucose time associated with a time of measuring the blood glucose measurement, the blood glucose type including one of a midsleep blood glucose measurement, a pre-breakfast blood glucose measurement, the pre-lunch blood glucose measurement, the pre-dinner blood glucose measurement, and a bedtime blood glucose measurement, wherein the midsleep, pre-breakfast, pre-lunch, pre-dinner, and bedtime blood glucose measurements are scheduled in a daily repetitive rotational order.

6. The method of claim 1, wherein determining the recommended meal bolus comprises:
  receiving a number of carbohydrates to be consumed by the patient for a meal associated with the determined blood glucose type; and
  dividing the received number of carbohydrates by the adjusted previous Carbohydrate-to-Insulin Ratio.

7. The method of claim 1, wherein adjusting the previous Carbohydrate-to-Insulin Ratio comprises, when the determined blood glucose type comprises the pre-lunch blood glucose measurement:
  obtaining the previous Carbohydrate-to-Insulin Ratio for breakfast; and
  determining a recommended Carbohydrate-to-Insulin Ratio for lunch by dividing the previous Carbohydrate-to-Insulin Ratio for breakfast by the adjustment factor.

8. The method of claim 1, wherein adjusting the previous Carbohydrate-to-Insulin Ratio comprises, when the determined blood glucose type comprises the pre-dinner blood glucose measurement:
  obtaining the previous Carbohydrate-to-Insulin Ratio for lunch; and
  determining a recommended Carbohydrate-to-Insulin Ratio for dinner by dividing the previous Carbohydrate-to-Insulin Ratio for lunch by the adjustment factor.

9. The method of claim 1, further comprising, when the determined blood glucose type comprises a pre-breakfast blood glucose measurement:
  obtaining, by the data processing hardware, a previous Carbohydrate-to-Insulin Ratio for dinner;
  obtaining, by the data processing hardware, a previous bedtime blood glucose measurement;
  determining, by the data processing hardware, a bedtime adjustment factor based on the previous bedtime blood glucose measurement; and
  determining, by the data processing hardware, a recommended Carbohydrate-to-Insulin Ratio for breakfast by dividing the previous Carbohydrate-to-Insulin Ratio for dinner by the bedtime adjustment factor.

10. The method of claim 9, further comprising:
  receiving, at the data processing hardware, a number of carbohydrates to be consumed by the patient for breakfast; and
  determining, by the data processing hardware, a recommended breakfast bolus by dividing the received number of carbohydrates by the recommended Carbohydrate-to-Insulin Ratio for breakfast.

11. The method of claim 10, further comprising transmitting the recommended breakfast bolus from the data processing device to the administration device, the doser configured to administer a number of units of insulin to the patient using the recommended breakfast bolus.

12. The method of claim 1, further comprising, when the determined blood glucose type comprises a pre-breakfast blood glucose measurement:
  selecting, by the data processing hardware, a governing blood glucose as a lesser one of a previous midsleep blood glucose measurement or the pre-breakfast blood glucose measurement;
  determining, by the data processing hardware, a basal adjustment factor for adjusting a current day's recommended basal dose based on the selected governing blood glucose measurement;
  obtaining, by the data processing hardware, a previous day's bed time recommended basal dose; and
  determining, by the data processing hardware, the current day's recommended basal dose by multiplying the adjustment factor times the previous day's bed time recommended basal dose, the current day's recommended basal dose corresponding to an insulin dose of long-acting insulin to be administered to the patient at a configurable frequency of one, two, or three times per day.

13. A system comprising:
  a glucometer measuring blood glucose measurements separated by a time interval; and
  a dosing controller in communication with the glucometer, the dosing controller including data processing hardware and memory hardware in communication with the data processing hardware, the dosing controller configured to perform operations comprising:

receiving a blood glucose measurement of a patient from the glucometer;

determining a blood glucose type of the received blood glucose measurement; and when the determined blood glucose type comprises one of a pre-lunch blood glucose measurement or a pre-dinner blood glucose measurement:

obtaining a previous Carbohydrate-to-Insulin Ratio for an immediately previous meal consumed by the patient, the immediately previous meal consumed by the patient comprising one of breakfast when the determined blood glucose type comprises the pre-lunch blood glucose measurement or lunch when the determined blood glucose type comprises the pre-dinner blood glucose type;

determining an adjustment factor based on the received blood glucose measurement;

adjusting the previous Carbohydrate-to-Insulin Ratio for the immediately previous meal consumed by the patient by dividing the previous Carbohydrate-to-Insulin Ratio by the adjustment factor;

determining a recommended meal bolus for the determined blood glucose type based on the adjusted previous Carbohydrate-to-Insulin Ratio; and transmitting the recommended meal bolus to an administration device in communication with the dosing controller, the administration device comprising:

a doser; and an administration computing device in communication with the doser, the administration computing device configured to cause the doser to administer a number of units of insulin to the patient using the recommended meal bolus.

14. The system of claim 13, wherein the operations further comprise determining a pre-meal correction bolus by calculating:

$$CB = (BG - BG_{Target})/CF,$$

wherein CB is the pre-meal correction bolus, BG is the received blood glucose measurement, $BG_{Target}$ is a target blood glucose value of a patient, and CF is a correction factor.

15. The system of claim 13, wherein determining the adjustment factor comprises:

determining whether the blood glucose value is within one of a plurality of target ranges of values; and when the blood glucose measurement is within one of the plurality of target ranges of values, setting the adjustment factor to a target adjustment factor associated with the corresponding target range of values that includes the blood glucose measurement.

16. The system of claim 15, wherein the plurality of target ranges of values comprises:

a first target range of values including blood glucose values less than a first configurable constant;

a second target range of values including blood glucose values greater than or equal to the first configurable constant and less than a low target blood glucose value of a target blood glucose range for the patient;

a third target range of values including blood glucose values greater than or equal to the low target blood glucose value and less than a high target blood glucose value of the target blood glucose range;

a fourth target range of values including blood glucose values greater than or equal to the high target blood glucose value and less than a second configurable constant;

a fifth target range of values including blood glucose values greater than or equal to the second configurable constant and less than a third configurable constant; and a sixth target range of values including blood glucose values greater than or equal to the third configurable constant.

17. The system of claim 13, wherein the blood glucose type is associated with a blood glucose time associated with a time of measuring the blood glucose measurement, the blood glucose type including one of a midsleep blood glucose measurement, a pre-breakfast blood glucose measurement, the pre-lunch blood glucose measurement, the pre-dinner blood glucose measurement, and a bedtime blood glucose measurement, wherein the midsleep, pre-breakfast, pre-lunch, pre-dinner, and bedtime blood glucose measurements are scheduled in a daily repetitive rotational order.

18. The system of claim 13, wherein determining the recommended meal bolus comprises:

receiving a number of carbohydrates to be consumed by the patient for a meal associated with the determined blood glucose type; and dividing the received number of carbohydrates by the adjusted previous Carbohydrate-to-Insulin Ratio.

19. The system of claim 13, wherein adjusting the previous Carbohydrate-to-Insulin Ratio comprises, when the determined blood glucose type comprises the pre-lunch blood glucose measurement:

obtaining the previous Carbohydrate-to-Insulin Ratio for breakfast; and determining a recommended Carbohydrate-to-Insulin Ratio for lunch by dividing the previous Carbohydrate-to-Insulin Ratio for breakfast by the adjustment factor.

20. The system of claim 13, wherein adjusting the previous Carbohydrate-to-Insulin Ratio comprises, when the determined blood glucose type comprises the pre-dinner blood glucose measurement:

obtaining the previous Carbohydrate-to-Insulin Ratio for lunch; and determining a recommended Carbohydrate-to-Insulin Ratio for dinner by dividing the previous Carbohydrate-to-Insulin Ratio for lunch by the adjustment factor.

21. The system of claim 13, wherein the operations further comprise, when the determined blood glucose type comprises a pre-breakfast blood glucose measurement:

obtaining a previous Carbohydrate-to-Insulin Ratio for dinner;

obtaining a previous bedtime blood glucose measurement;

determining a bedtime adjustment factor based on the previous bedtime blood glucose measurement; and determining a recommended Carbohydrate-to-Insulin Ratio for breakfast by dividing the previous Carbohydrate-to-Insulin Ratio for dinner by the bedtime adjustment factor.

22. The system of claim 21, wherein the operations further comprise:

receiving a number of carbohydrates to be consumed by the patient for breakfast; and determining a recommended breakfast bolus by dividing the received number of carbohydrates by the recommended Carbohydrate-to-Insulin Ratio for breakfast.

23. The system of claim 22, wherein the operations further comprise transmitting the recommended breakfast bolus to the administration device, the doser configured to administer a number of units of insulin to the patient using the recommended breakfast bolus.

24. The system of claim 13, wherein the operations further comprise, when the determined blood glucose type comprises a pre-breakfast blood glucose measurement:
- selecting a governing blood glucose as a lesser one of a previous midsleep blood glucose measurement or the pre-breakfast blood glucose measurement;
- determining basal adjustment factor for adjusting a current day's recommended basal dose based on the selected governing blood glucose measurement;
- obtaining a previous day's bed time recommended basal dose; and
- determining the current day's recommended basal dose by multiplying the basal adjustment factor times the previous day's bed time recommended basal dose, the current day's recommended basal dose corresponding to an insulin dose of long-acting insulin to be administered to the patient at a configurable frequency of one, two, or three times per day.

* * * * *